US012161975B2

United States Patent
Tehrani

(10) Patent No.: US 12,161,975 B2
(45) Date of Patent: Dec. 10, 2024

(54) FLUID PURIFICATION FILTERS AND THE METHOD OF FLUID PURIFICATION USING THE SAME

(71) Applicant: Temple University-Of The Commonwealth System of Higher Education, Philadelphia, PA (US)

(72) Inventor: Rouzbeh Afsarmamesh Tehrani, Radnor, PA (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 563 days.

(21) Appl. No.: 17/428,145

(22) PCT Filed: Feb. 4, 2020

(86) PCT No.: PCT/US2020/016473
§ 371 (c)(1),
(2) Date: Aug. 3, 2021

(87) PCT Pub. No.: WO2020/163252
PCT Pub. Date: Aug. 13, 2020

(65) Prior Publication Data
US 2022/0054983 A1    Feb. 24, 2022

Related U.S. Application Data

(60) Provisional application No. 62/800,697, filed on Feb. 4, 2019.

(51) Int. Cl.
*B01D 63/06* (2006.01)
*A61M 1/16* (2006.01)
(Continued)

(52) U.S. Cl.
CPC .......... *B01D 63/06* (2013.01); *A61M 1/1627* (2014.02); *A61M 1/1696* (2013.01); *B01D 61/30* (2013.01);
(Continued)

(58) Field of Classification Search
CPC .......... B01D 63/06; B01D 2311/2626; B01D 2315/10; C02F 1/281; C02F 1/44
See application file for complete search history.

(56) References Cited

U.S. PATENT DOCUMENTS 4,963,264 A   10/1990  Davis
6,858,147 B2   2/2005  Dukhin
(Continued)

FOREIGN PATENT DOCUMENTS

CN         105540915 B  *  4/2018

OTHER PUBLICATIONS

Wu et al.—CN-105540915-B machine translation—Apr. 27, 2018 (Year: 2018).*
(Continued)

*Primary Examiner* — Bradley R Spies
(74) *Attorney, Agent, or Firm* — Riverside Law LLP

(57) ABSTRACT

The present invention relates in part to a filter comprising a tubular housing having a proximal end, a distal end and a housing lumen therethrough; a tubular membrane having a proximal end, a distal end and a membrane lumen therethrough, wherein the tubular membrane is positioned within the housing lumen; a contaminated fluid sample inlet fluidly connected to the proximal end of the membrane, and a contaminated fluid sample outlet fluidly connected to the distal end of the membrane, thereby creating a sample flow-path from the sample inlet through the membrane lumen to the sample outlet; and a purification material inlet fluidly connected to a distal region of the housing lumen, (Continued)

and a purification material outlet fluidly connected to a proximal region of the housing lumen, thereby creating a purification material flow-path from the purification material inlet through the housing lumen to the purification material outlet; wherein the direction of the sample flow-path is in the opposite direction of the purification material flow-path. The invention also relates a method of purifying a contaminated fluid using said filter.

13 Claims, 36 Drawing Sheets

(51) Int. Cl.
  *B01D 61/30* (2006.01)
  *C02F 1/28* (2023.01)
  *C02F 1/44* (2023.01)
  *C02F 101/10* (2006.01)
  *C02F 101/20* (2006.01)

(52) U.S. Cl.
  CPC .......... *C02F 1/281* (2013.01); *C02F 1/44* (2013.01); *B01D 2311/2626* (2013.01); *B01D 2315/10* (2013.01); *C02F 2101/103* (2013.01); *C02F 2101/20* (2013.01); *C02F 2305/04* (2013.01); *C02F 2305/08* (2013.01)

(56) References Cited

U.S. PATENT DOCUMENTS

| | | |
|---|---|---|
| 2004/0173531 A1 | 9/2004 | Hammond |
| 2008/0035541 A1 | 2/2008 | Franzreb |
| 2008/0199355 A1 | 8/2008 | Berentsveig |
| 2011/0311822 A1 | 12/2011 | Hao |
| 2015/0053085 A1 | 2/2015 | Mahley, III |

OTHER PUBLICATIONS

Adeleye, Conway, Garner, Huang, Su, and Keller 2016, Chem. Eng. J., 286:640-662.
Ding, W. et al. Int. J. Heat Mass Transf. 47, 4849-4855 (2004).
Feng, et al. Journal of Hazardous Materials, vol. 217-218, 439-446, 2012.
Qu, Alvarez, and Li 2013, Water Res., 47:3931-3946.
Zhao, et al. Clays and Clay Minerals, vol. 57, 513-520, 2009.

\* cited by examiner

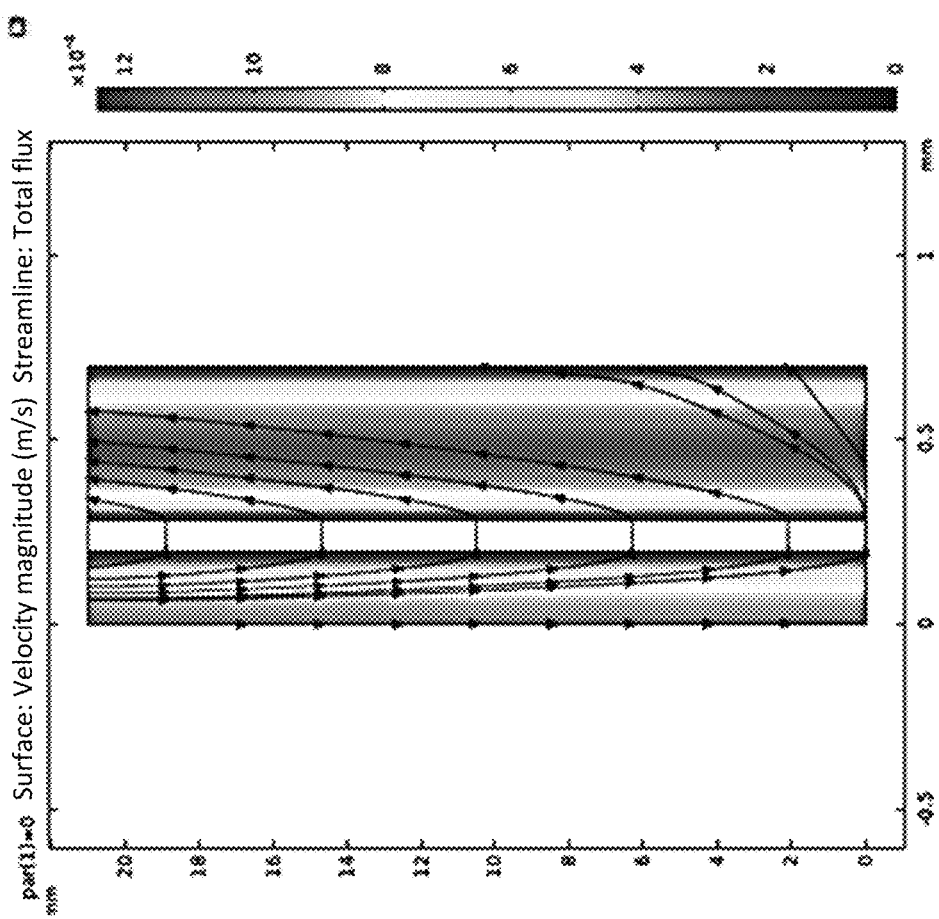
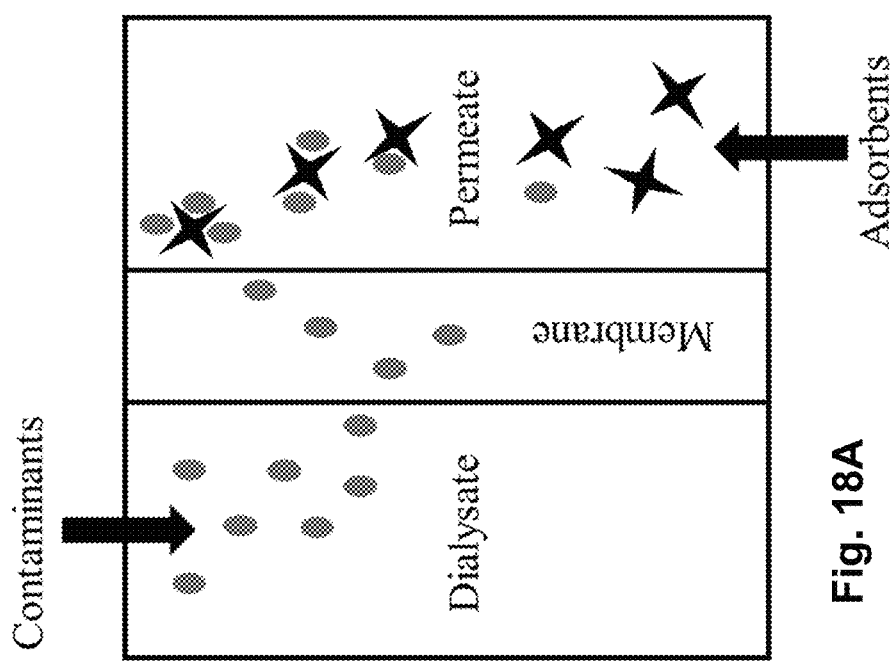
Fig. 18A
Fig. 18B

FLUID PURIFICATION FILTERS AND THE METHOD OF FLUID PURIFICATION USING THE SAME

CROSS-REFERENCE TO RELATED APPLICATIONS

This application is a National Stage Application claiming priority to International Patent Application No. PCT/US2020/016473 filed on Feb. 4, 2020, which is entitled to priority under 35 U.S.C. § 119(e) to U.S. provisional application No. 62/800,697, filed Feb. 4, 2019, the disclosures of which are incorporated herein by reference in their entirety.

BACKGROUND OF THE INVENTION

Nanomaterials have been extensively explored in the past few decades. They are possibly the most promising alternative materials in developing the next generation of water treatment technologies (Zhang et al. 2016, NanoImpact, 3-4:22-39). Recent advances in nanoscience have introduced new adsorbent with high surface area, specificity, and reactivity (Mondal et al. 2013, Chemosphere, 92: 157-170). Thus, nanomaterials are an emerging class of adsorbents due to their high specific surface areas and high specificity. However, the nanoparticles tend to aggregate in aqueous solution. The aggregation results in a drastic decrease in surface area. Therefore, their capacity, selectivity, lifetime, and potential for real-life application decrease considerably (Qu, Alvarez and Li 2013, Water Res., 47:3931-3946; Zhang et al. 2016, NanoImpact, 3-4:22-39). In addition, compatibility between the use of nanoadsorbent with the current water treatment infrastructure is an application constraint (Adeleye, Conway, Gamer, Huang, Su, and Keller 2016, Chem. Eng. J., 286:640-662). Many researchers have suggested the use of nanoadsorbents in slurry reactors (Qu, Alvarez, and Li 2013, Water Res., 47:3931-3946). This approach requires an addition of a separation unit in the water treatment process that may simply make the use of nanoscale adsorbent infeasible. Use of nanoadsorbents in fixed or fluidized bed reactors, in the form of beads, pellets, or porous granules, are also tested. The problem with fixed-bed reactors is limitation of mass transfer and expected head loss, but such methods do not require a separation unit. Unfortunately, many studies are conducted in lab scale, for a short period, and with nonrealistic conditions.

ADSORBSIA™ and ArsenX$^{np}$ are two examples of the use of commercially available nanoscale particles for arsenic removal. ADSORBSIA™ is a nanocrystalline titanium dioxide medium in the form of beads and ArsenX$^{np}$ is a hybrid ion exchange medium containing iron oxide nanoparticles. Both ADSORBSIA™ and ArsenX$^n$ have been used in small to medium drinking water treatments systems. There is no commercially available nanoscale water treatment technology that has been employed in large scale water treatment systems. There is no literature available for a financially feasible nanoscale water treatment technology that is practical and reliable in industrially scaled water treatment plants.

There is a need in the art for a feasible and sustainable system to use purification materials, such as nanomaterials, for the efficient purification of fluids. The present invention satisfies this unmet need.

SUMMARY OF THE INVENTION

In one aspect, the current invention relates to a filter comprising a tubular housing having a proximal end, a distal end and a housing lumen therethrough; a tubular membrane having a proximal end, a distal end and a membrane lumen therethrough, wherein the tubular membrane is positioned within the housing lumen; a contaminated fluid sample inlet fluidly connected to the proximal end of the membrane, and a contaminated fluid sample outlet fluidly connected to the distal end of the membrane, thereby creating a sample flow-path from the sample inlet through the membrane lumen to the sample outlet; and a purification material inlet fluidly connected to a distal region of the housing lumen, and a purification material outlet fluidly connected to a proximal region of the housing lumen, thereby creating a purification material flow-path from the purification material inlet through the housing lumen to the purification material outlet; wherein the direction of the sample flow-path is in the opposite direction of the purification material flow-path.

In one embodiment, the tubular membrane is permeable to at least one fluid and at least one contaminant, and wherein the tubular membrane is non-permeable to at least one purification material. In one embodiment, the tubular membrane is non-permeable to a material with a molecular weight of at least 50 kDa. In one embodiment, the tubular membrane comprises a membrane selected from the group consisting of cation exchange membrane (CEM), anion exchange membrane (AEM), alkali anion exchange membrane (AAEM), proton exchange membrane (PEM), charge mosaic membrane (CMM), and bipolar membrane (BPM). In one embodiment, the tubular membrane comprises a material selected from the group consisting of an organic polymer, an inorganic polymer, and any combination thereof. In one embodiment, the tubular membrane comprises a material selected from the group consisting of a nylon, cellulose, cellulose ester, fluorinated polymer, and any combination thereof.

In one embodiment, the tubular housing is non-permeable to at least one fluid, at least one contaminant, and at least one purification material. In one embodiment, the tubular housing comprises a material selected from the group consisting of a glass, quartz, ceramic, silica, alloy, metal alloy, stainless steel, stainless steel alloy, aluminum, aluminum alloy, aluminum oxide, copper, copper alloy, titanium, titanium alloy, brass, plastic, and any combination thereof.

In one embodiment, the filter further comprises a regeneration unit fluidly connected to the purification material inlet and the purification material outlet, wherein the regeneration unit regenerates the purification material.

The present invention also relates to a method of purifying a contaminated fluid, the method comprising providing a filter described herein; passing a contaminated fluid comprising at least one contaminant through the contaminated fluid sample inlet; passing a purification material through the purification material inlet; permeating the at least one contaminant through the tubular membrane to the housing lumen; and collecting a purified fluid.

In one embodiment, the method further comprises the step of adsorbing a contaminant onto the purification material. In one embodiment, the method comprises the step of regenerating the purification material.

In one embodiment, the purification material comprises a material selected from the group consisting of a nanomaterial, a nanoadsorbent, an adsorbent, a microorganism, a bacterium, a bacterial community, a bacterial slurry, or any combination thereof. In one embodiment, the nanomaterial is selected from the group consisting of charcoal, powdered activated carbon (PAC), graphite, graphene, graphene oxide, manganese oxides ($MnO_x$), iron oxides ($Fe_yO_z$), manganese sulfides ($MnS_x$), molybdenum oxides ($MoO_x$), molybdenum sulfides (MoS$_x$), silicon oxides (SiO$_x$), silicon sulfides (SiS$_x$), aluminum oxides (Al$_y$O$_z$), aluminum sulfides (Al$_y$S$_z$), boron oxides (B$_y$O$_z$), zeolites, tungsten diselenide (WSe$_2$), niobium diselenide (NbSe$_2$), boron nitride (BN), tungsten sulfide (WS$_2$), phosphorene (PR$_3$), tin (Sn), transition metal di-chalcogenides, and any combination thereof. In one embodiment, the nanomaterial is manganese oxide (MnO$_x$).

In one embodiment, the tubular membrane further comprises a surfactant. In one embodiment, the surfactant is selected from the group consisting of lecithin, saponin, monolaurin, glycerol monostearate, glyceryl hydroxystearate, gum arabic, Polysorbate 20, Polysorbate 65, Polysorbate 80, capric acid, caprylic acid, lauric acid, myristic acid, oleic acid, palmitic acid, agar, alginic acid, beta glucan, carrageenan, *cassia* gum, chicle gum, dammar gum, gellan gum, glucomannan, guar gum, gum ghatti, gum karaya, konjac, locust bean gum, psyllium, sodium alginate, tara spinose, tragacanth, xanthan gum, quillaja, baker's yeast glycan, mastic, stearic acid, monoglycerides of fatty acids, butyric acid, potassium caprate, potassium caprylate, potassium laurate, potassium myristate, potassium oleate, potassium palmitate, sodium myristate, sodium palmitate, sodium stearate, ethyl methyl cellulose, DATEM, ethoxylated glycerides, sorbitan monostearate, Polysorbate 60, docusate, lactylated fatty acid ester of glycerol, lactylated fatty acid ester of propylene glycol, polyethylene glycol oleate, sodium dodecyl sulfate, sodium stearoyl lactylate, sucrose acetate isobutyrate, glycerol, sorbitan monooleate, polyethylene glycol, and cyclodextrin.

In one embodiment, the contaminated fluid is selected from the group consisting of water, drinking fluids, blood, blood serum, oils, milk, alcohols, solvents, organic solvents, and any combination thereof. In one embodiment, the contaminant is selected from a group consisting of aluminum, ammonia, arsenic, barium, cadmium, chloramine, chromium, copper, fluoride, lead, nitrates, nitrites, mercury, perchlorates, radium, selenium, sulfur, silver, uranium, iron, iron oxides (Fe$_y$O$_z$), asbestos, perfluoroalkyl substances, polyfluoroalkyl substances (PFAS), perfluorooctanesulfonic acid (PFOS), perfluorooctanoic acid (PFOA), bacteria, viruses, potassium bicarbonate, sodium bicarbonate, phosphates, and any combination thereof.

The present invention further relates to a fluid purification system comprising a filter described herein.

BRIEF DESCRIPTION OF THE DRAWINGS

The following detailed description of various embodiments of the invention will be better understood when read in conjunction with the appended drawings. For the purpose of illustrating the invention, there are shown in the drawings illustrative embodiments. It should be understood, however, that the invention is not limited to the precise arrangements and instrumentalities of the embodiments shown in the drawings.

FIG. 3, comprising FIG. 3A depicts a lateral view of a purification membrane filter. FIG. 3B depicts a cross-section view of a purification membrane filter.

FIG. 8, comprising FIG. 8A depicts a design of the small-scale purification membrane filter. FIG. 8B depicts an empty small-scale purification membrane filter. FIG. 8C depicts a small-scale purification membrane filter filled with contaminated water.

FIG. 9, comprising FIG. 9A depicts the flow of contaminated water and the opposite flow of nanomaterials. FIG. 9B depicts a process of a purification method of contaminated water using a purification membrane filter comprising of 2D birnessite nanomaterials.

FIG. 10, comprising FIG. 10A depicts a concentration of lead (Pb) in an inside and outside tubular membrane of the purification membrane filter, which was not filled with a nanomaterial. FIG. 10B depicts a concentration of lead (Pb) in an inside and outside tubular membrane of the purification membrane filter filled with a nanomaterial (0.15 g adsorbent).

FIG. 13, comprising FIG. 13A depicts a concentration of lead (Pb) in an inside and outside tubular membrane of the horizontal purification membrane filter setup. FIG. 13B depicts a concentration of lead (Pb) in an inside and outside tubular membrane of the vertical purification membrane filter setup

FIGS. 15B, 15C, 15D, and 15E, is a series of micrographs of birnessite with and without Pb$^{2+}$ contaminants. FIG. 15B is a TEM image of unloaded birnessite. FIG. 15C is a TEM image of Pb$^{2+}$-loaded birnessite. FIG. 15D is an SEM image of birnessite. FIG. 15E is a SEM image of Pb$^{2+}$-loaded birnessite.

FIG. 18, comprising FIGS. 18A and 18B, shows results from computational simulations. FIG. 18A is a schematic of the proposed process. FIG. 18B is a diagram showing velocity magnitudes of dialysate and permeate, arrows show theoretical flow path of contaminants (not scaled).

FIG. 19, comprising FIG. 19A is a plot of stationary contaminant concentration profile (red presents the highest concentration of contaminant). FIG. 19B is a plot showing stationary concentration profile of open-sites for adsorption (red presents the highest concentration of free-sites of adsorbents, blue presents the highest concentration of exploited sites).

Figure 21:
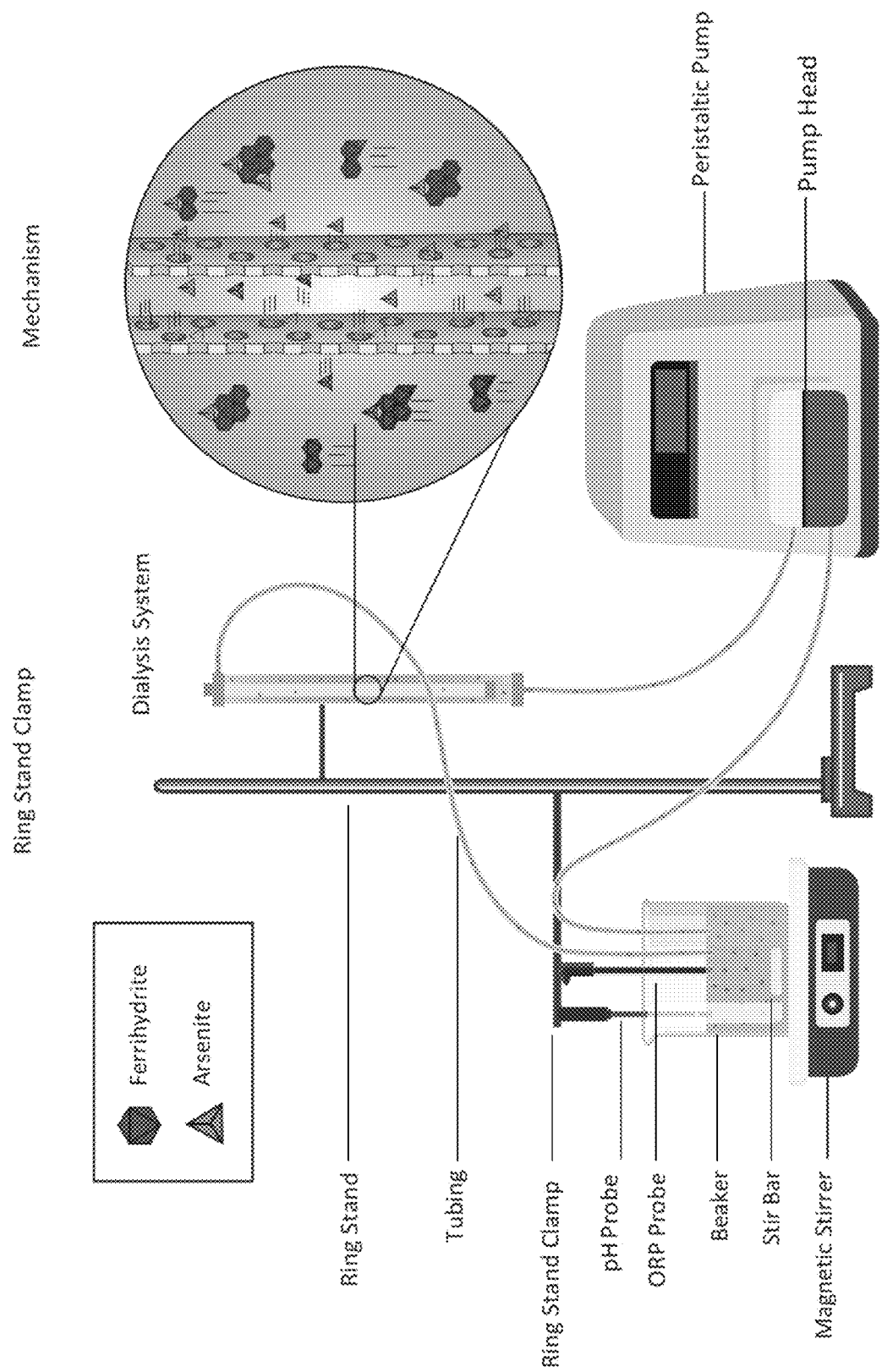

FIG. 21 is a schematic showing a proposed system for the application of nanomaterials in fluid purification.

Figure 22:
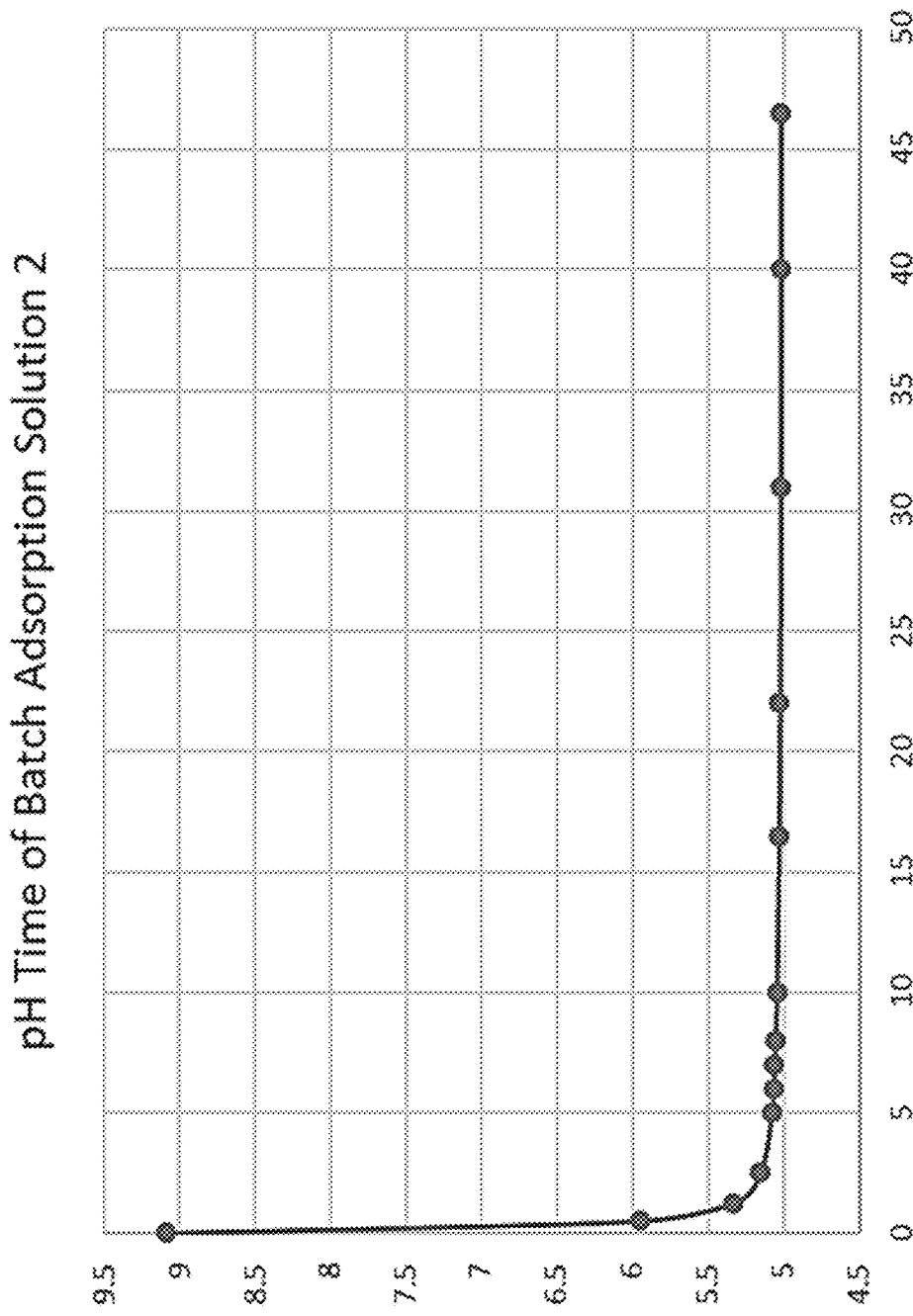

FIG. 22 is a plot showing the change in pH to a 0.22 M sodium nitrate solution loaded with 1.25 g/L TLFH.

Figure 23:
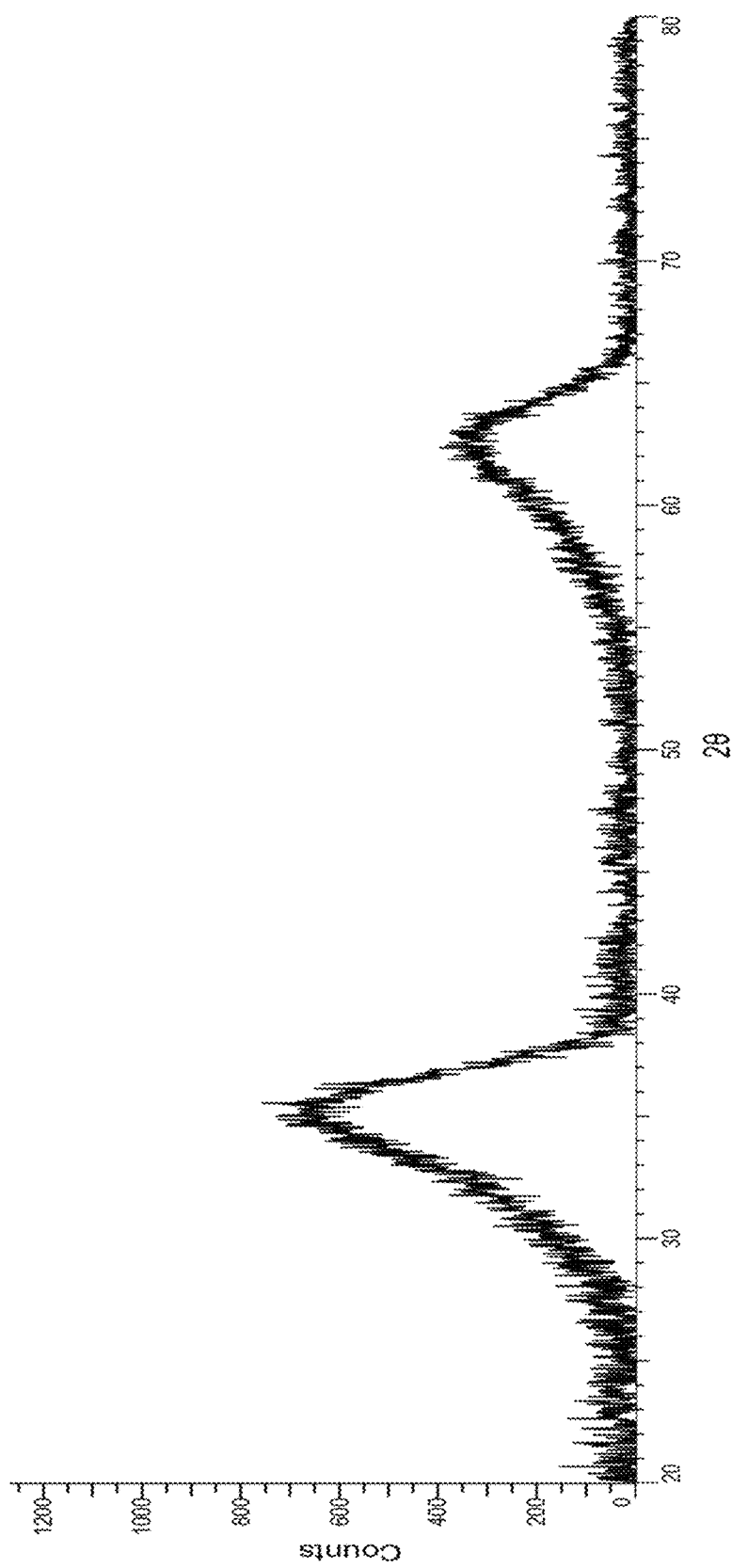

FIG. 23 is a powder XRD diffractogram of Fh synthesized by SDM.

Figure 24:
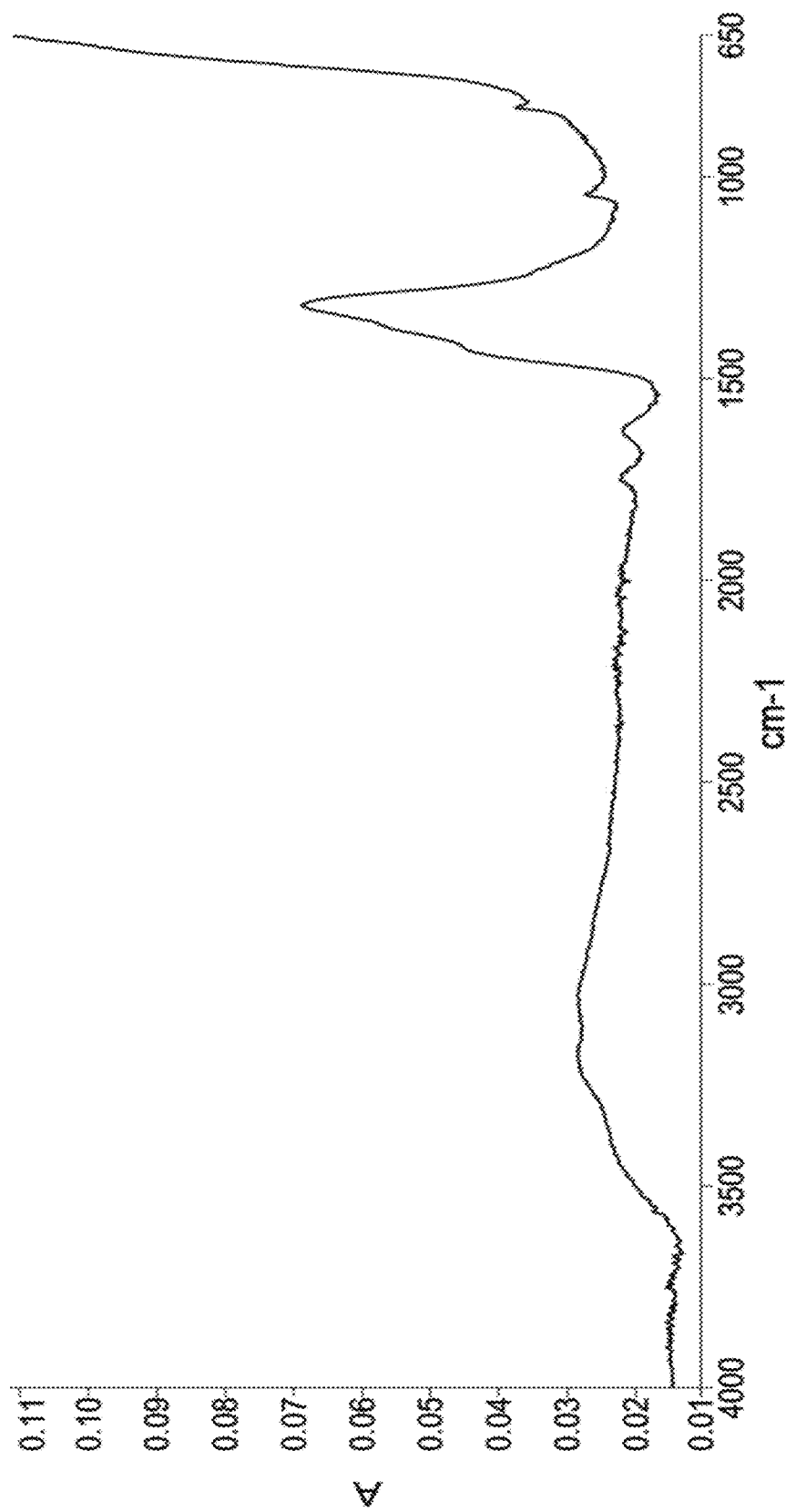

FIG. 24 is an ATR-FTIR spectrum of Fh synthesized by SDM.

Figure 25:
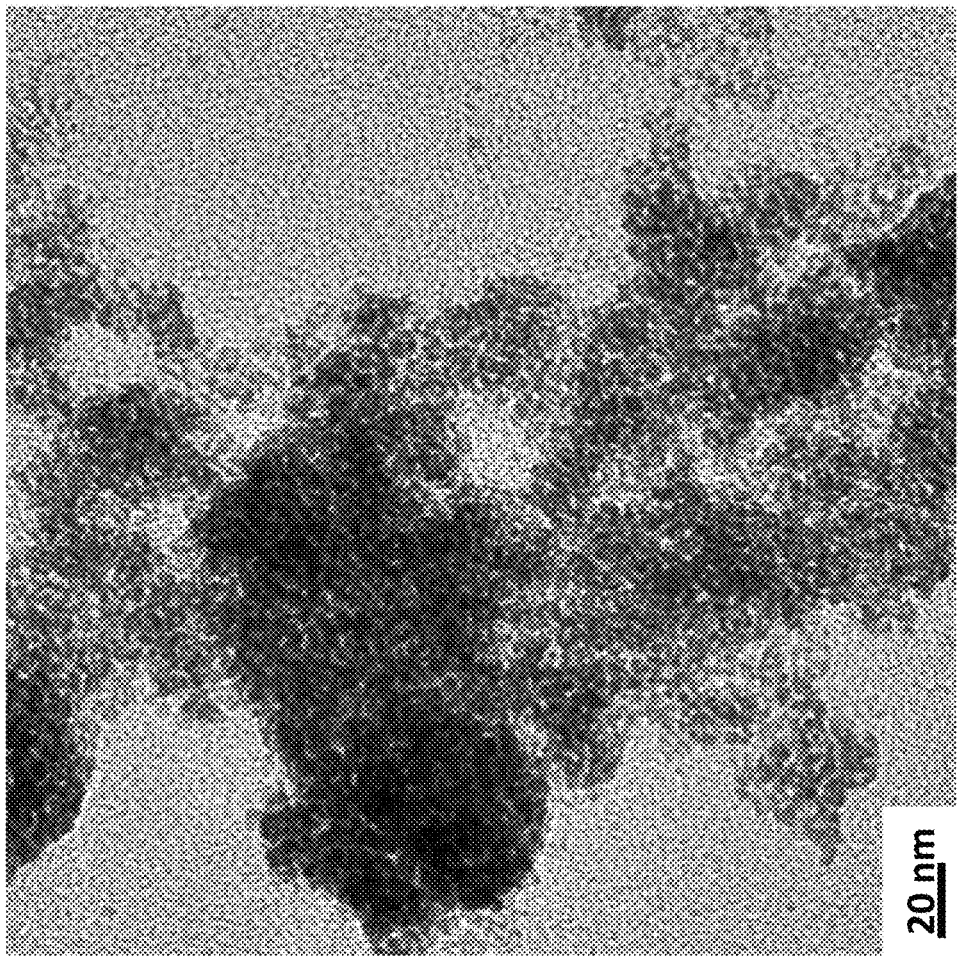

FIG. 25 is a TEM image of Fh.

Figure 26:
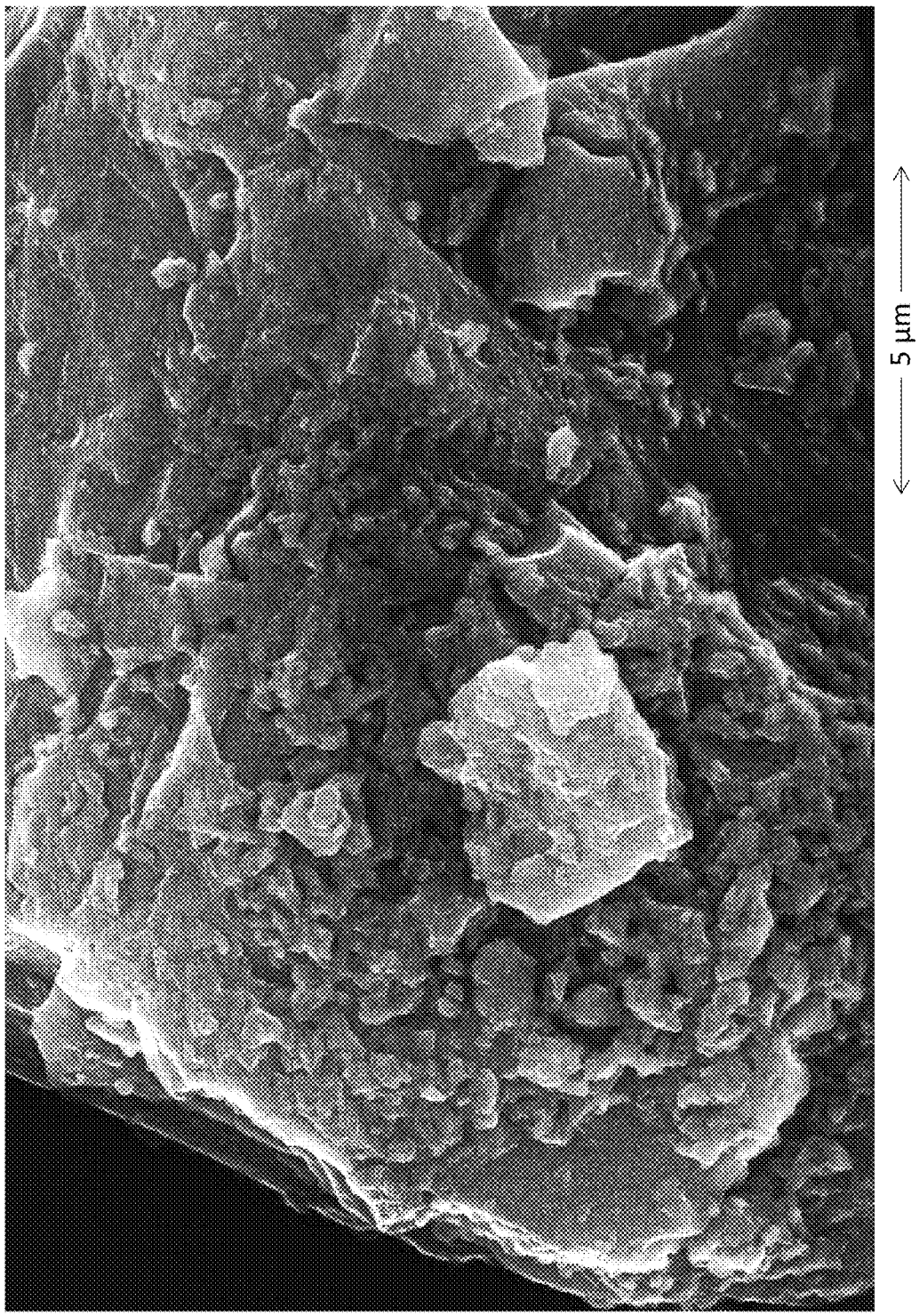

FIG. 26 is an SEM image of Fh.

Figure 27:
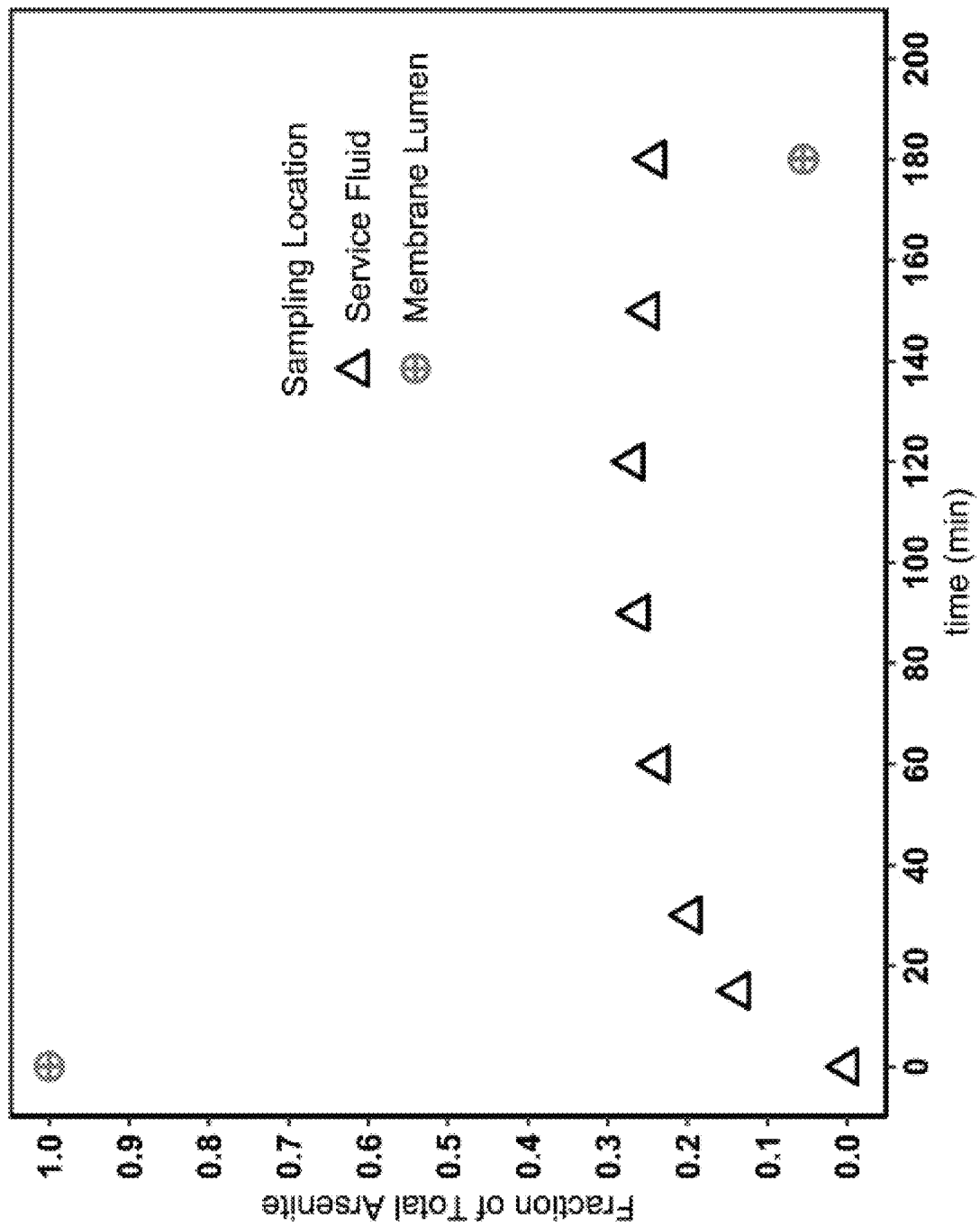

FIG. 27 is a plot of residual arsenite in the membrane lumen and service fluid of the system over time for 1.22 g/L adsorbent loading. Amount of arsenite is presented as a mass fraction of total arsenic.

Figure 28:
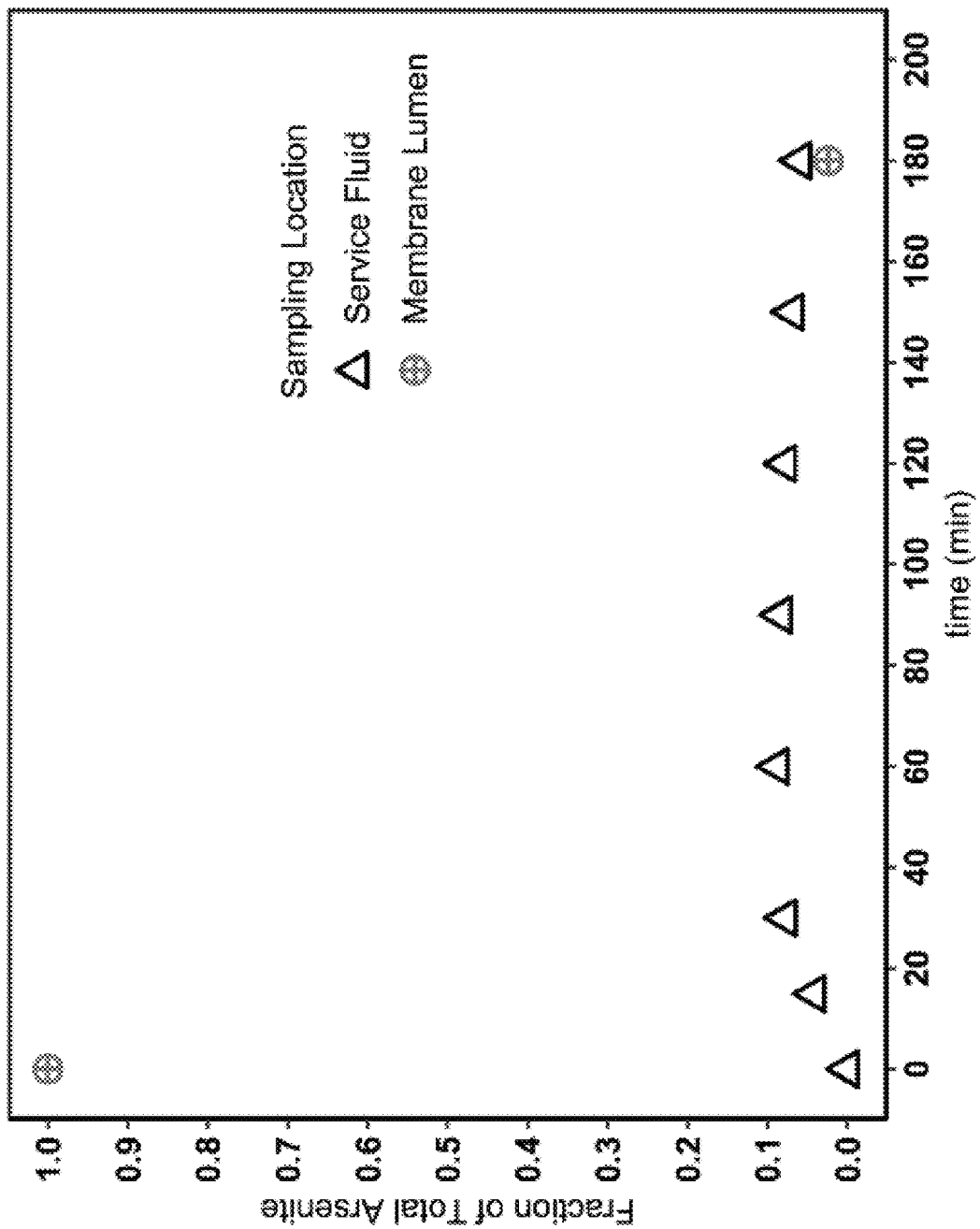

FIG. 28 is a plot of residual arsenite in the membrane lumen and service fluid of the system over time for 2.61 g/L adsorbent loading. Amount of arsenite is presented as a mass fraction of total arsenic.

Figure 29:
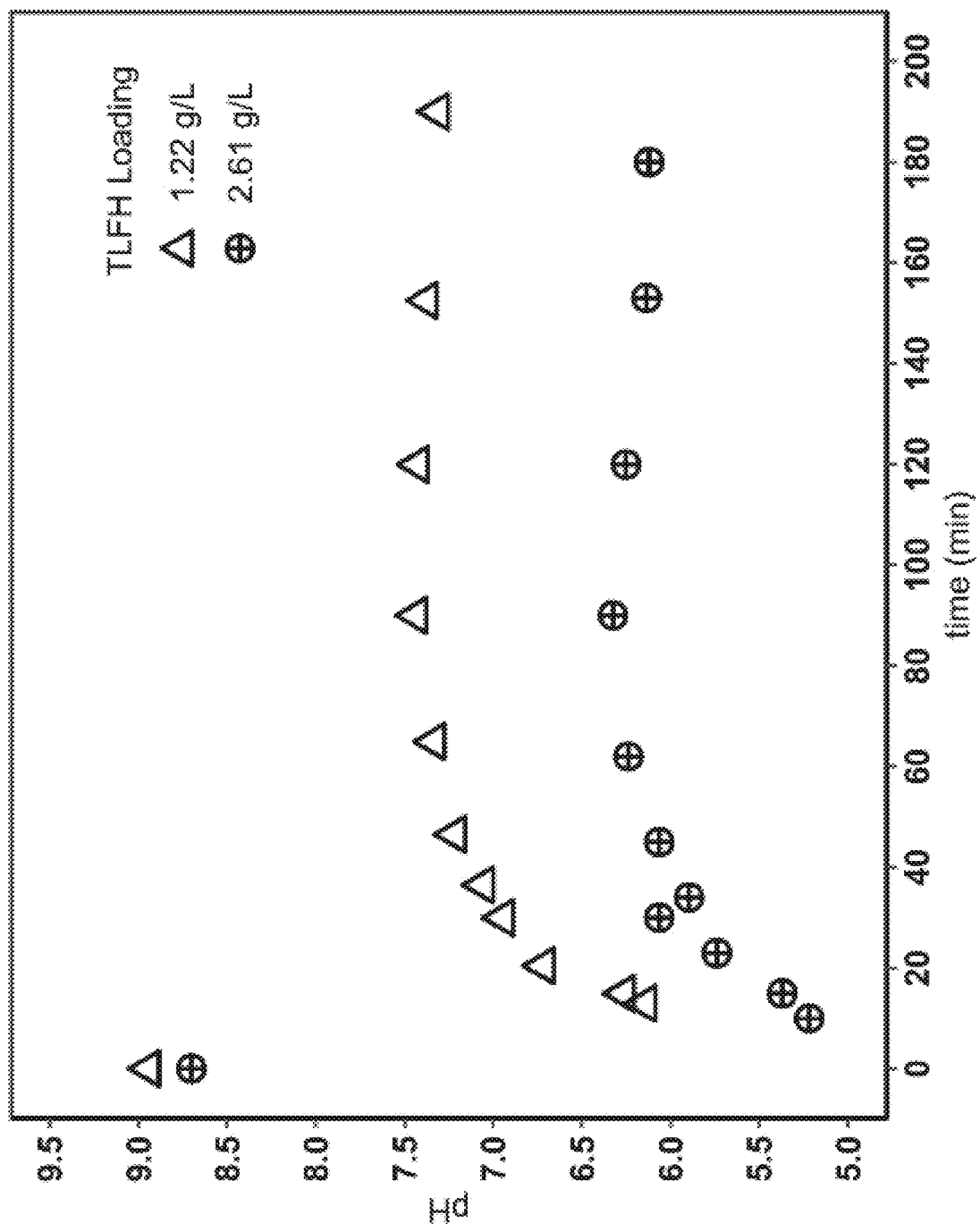

FIG. 29 is a plot of the change in pH of the service fluid with 1.25 and 2.68 g/L Fh loading.

Figure 30:
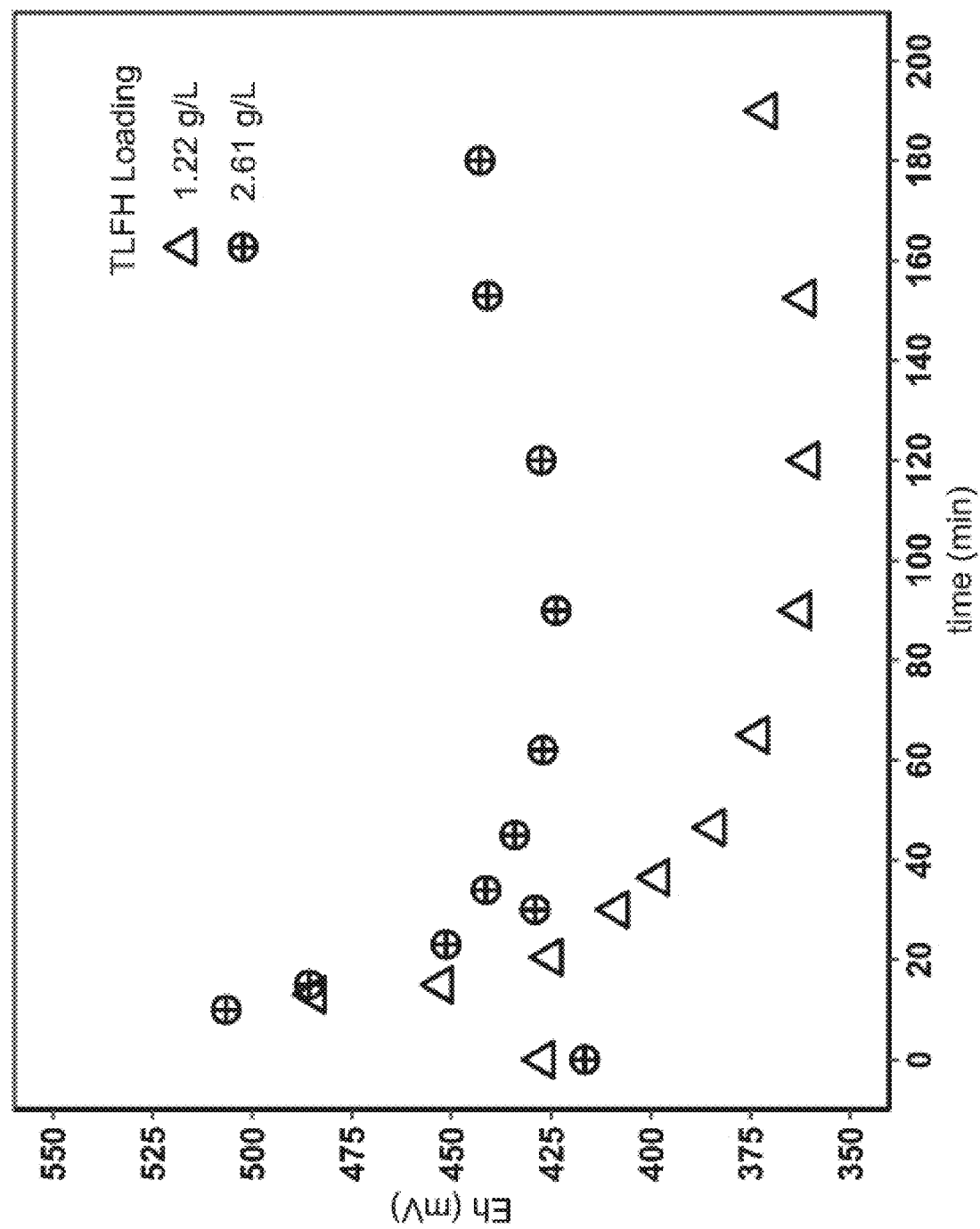

FIG. 30 is a plot of the change in Eh of the service fluid with 1.25 and 2.68 g/L Fh loading.

Figure 31:
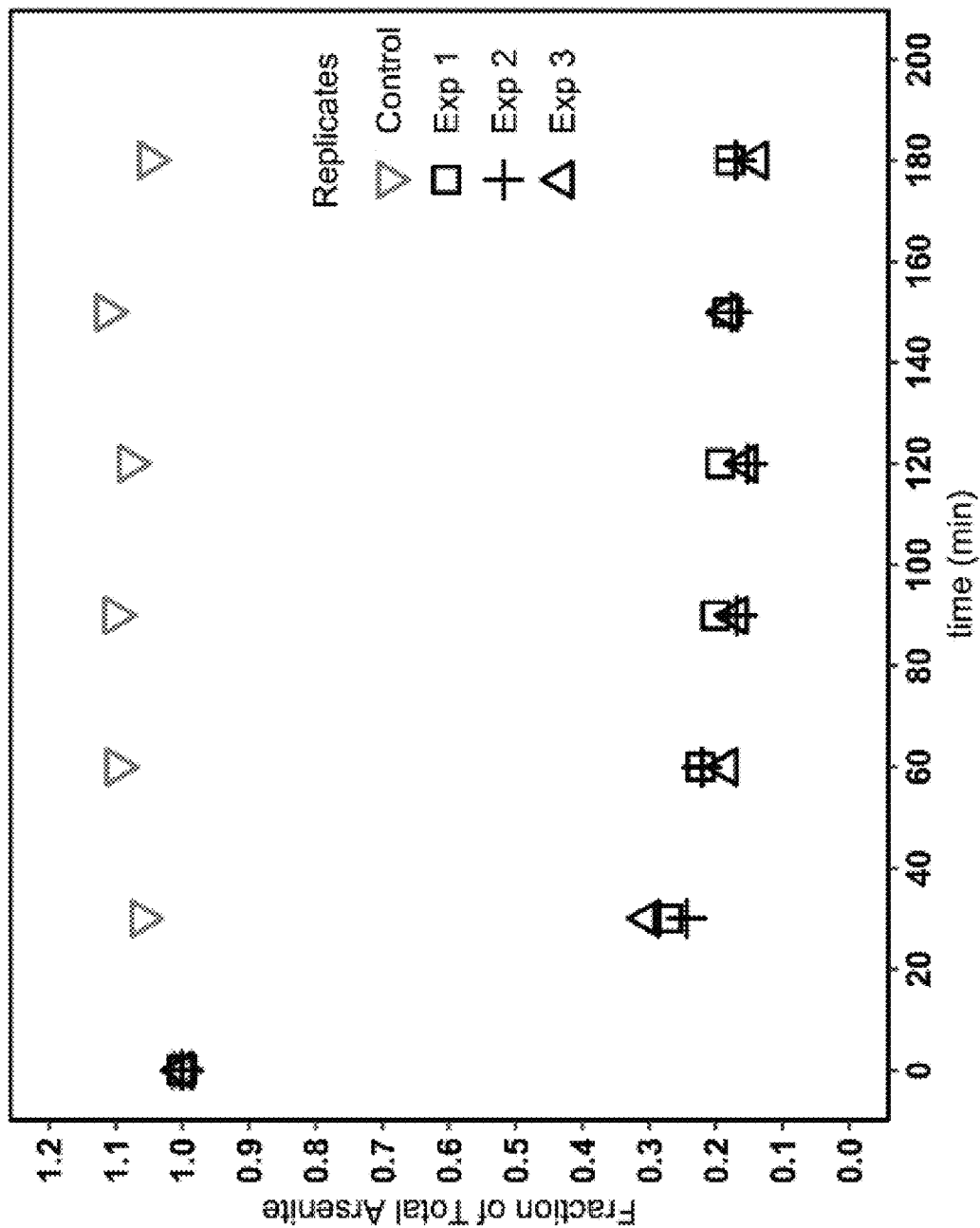

FIG. 31 is a plot of the removal of arsenite in batch experiments over time for 1.25 g/L adsorbent loading. Amount of arsenite remaining in solution is presented as a mass fraction of total arsenic.

Figure 32:
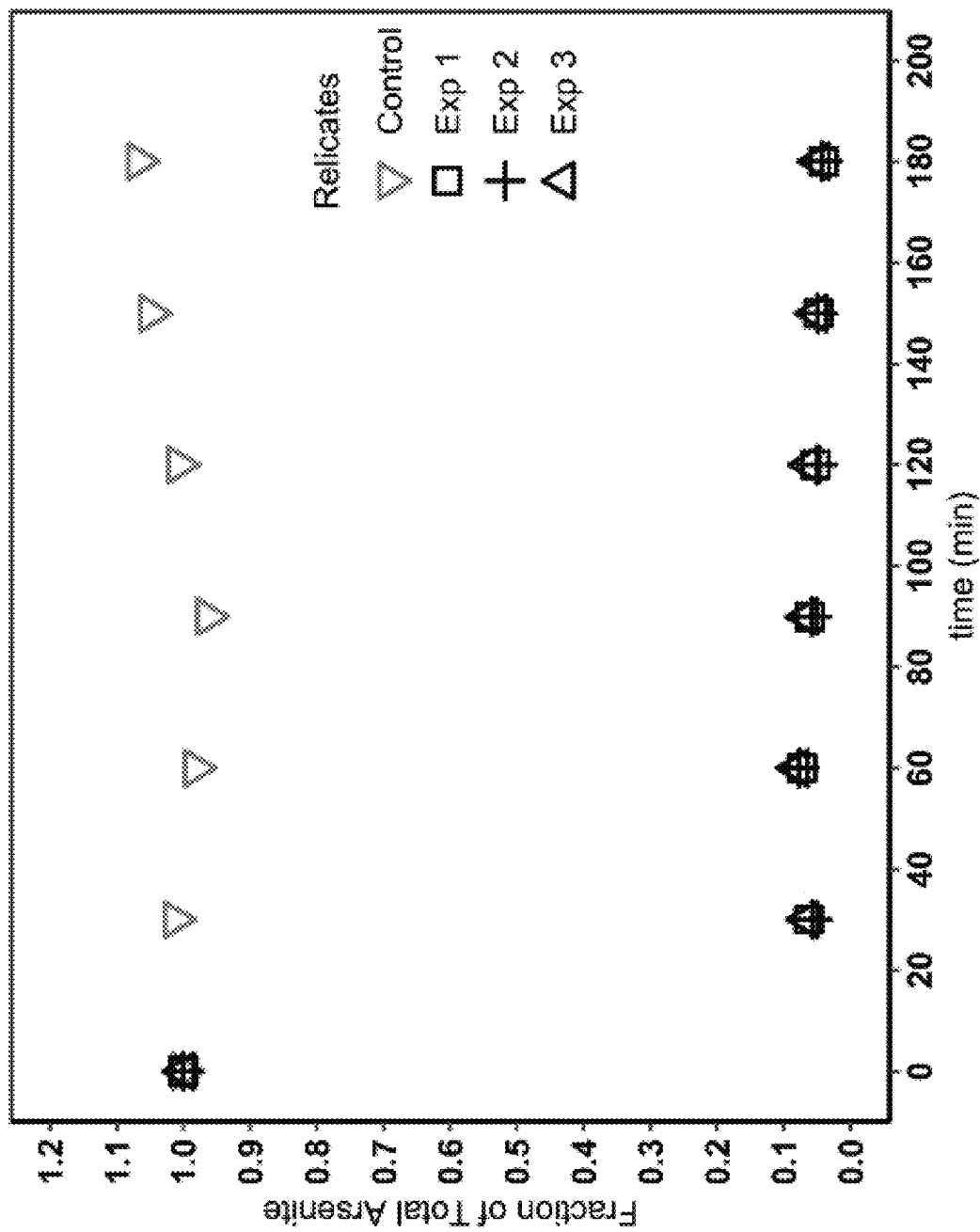

FIG. 32 is a plot of the removal of arsenite in batch experiments over time for 2.68 g/L adsorbent loading. Amount of arsenite remaining in solution is presented as a mass fraction of total arsenic.

Figure 33:
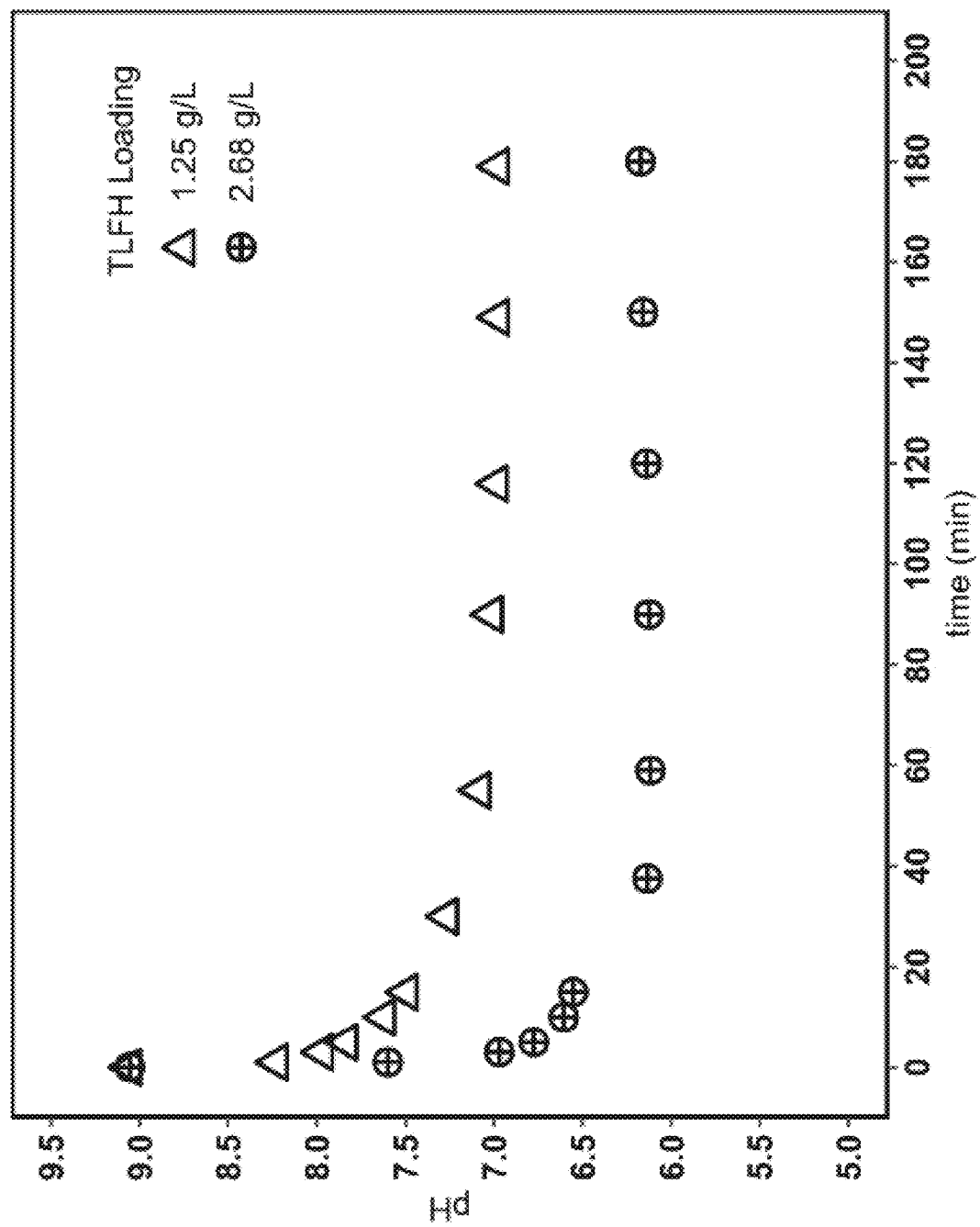

FIG. 33 is a plot showing the change in pH of batch arsenic removal with 1.25 and 2.68 g/L Fh loadings.

Figure 34:
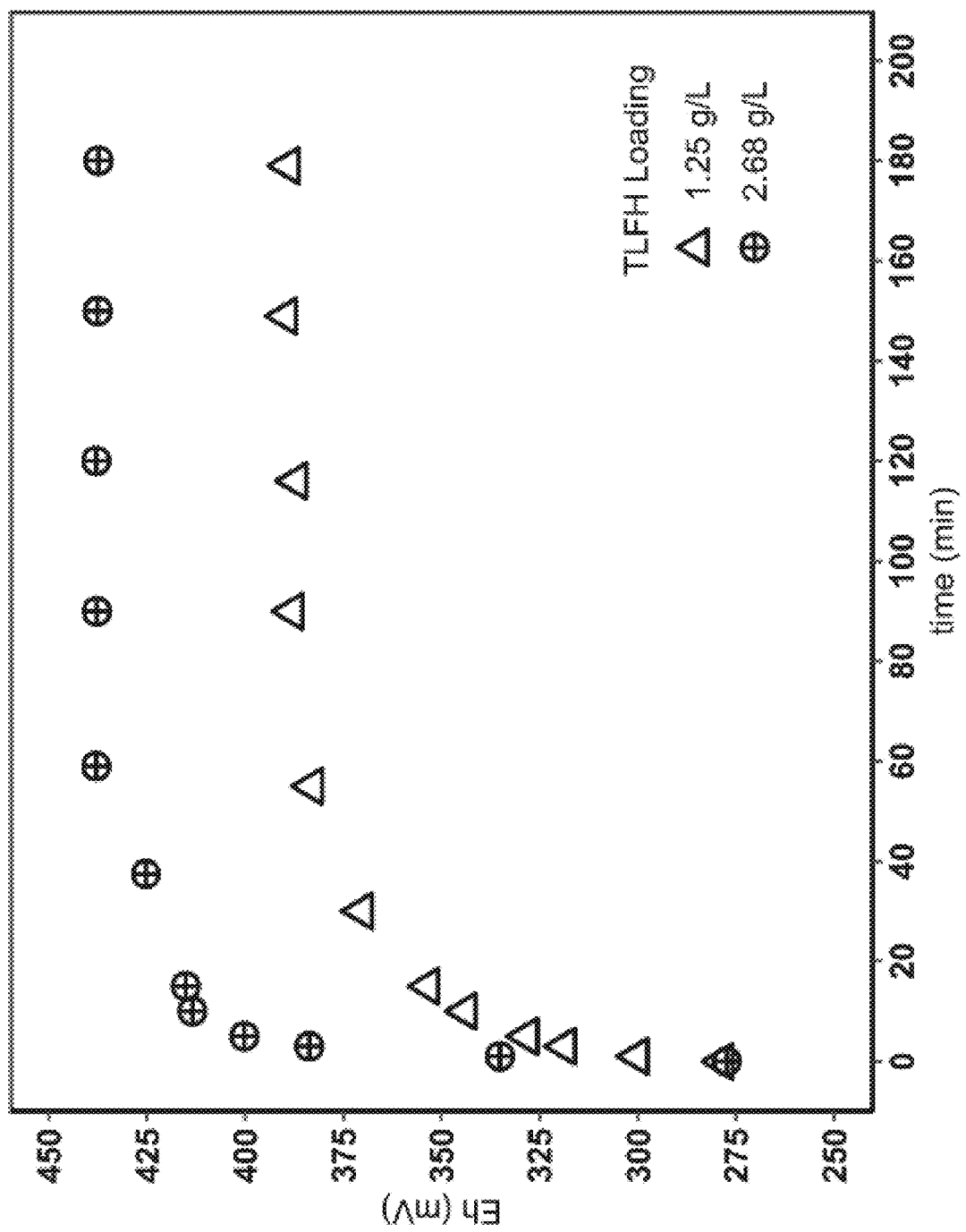

FIG. 34 is a plot showing the change in Eh of batch arsenic removal with 1.25 and 2.68 g/L Fh loadings.

Figure 35:
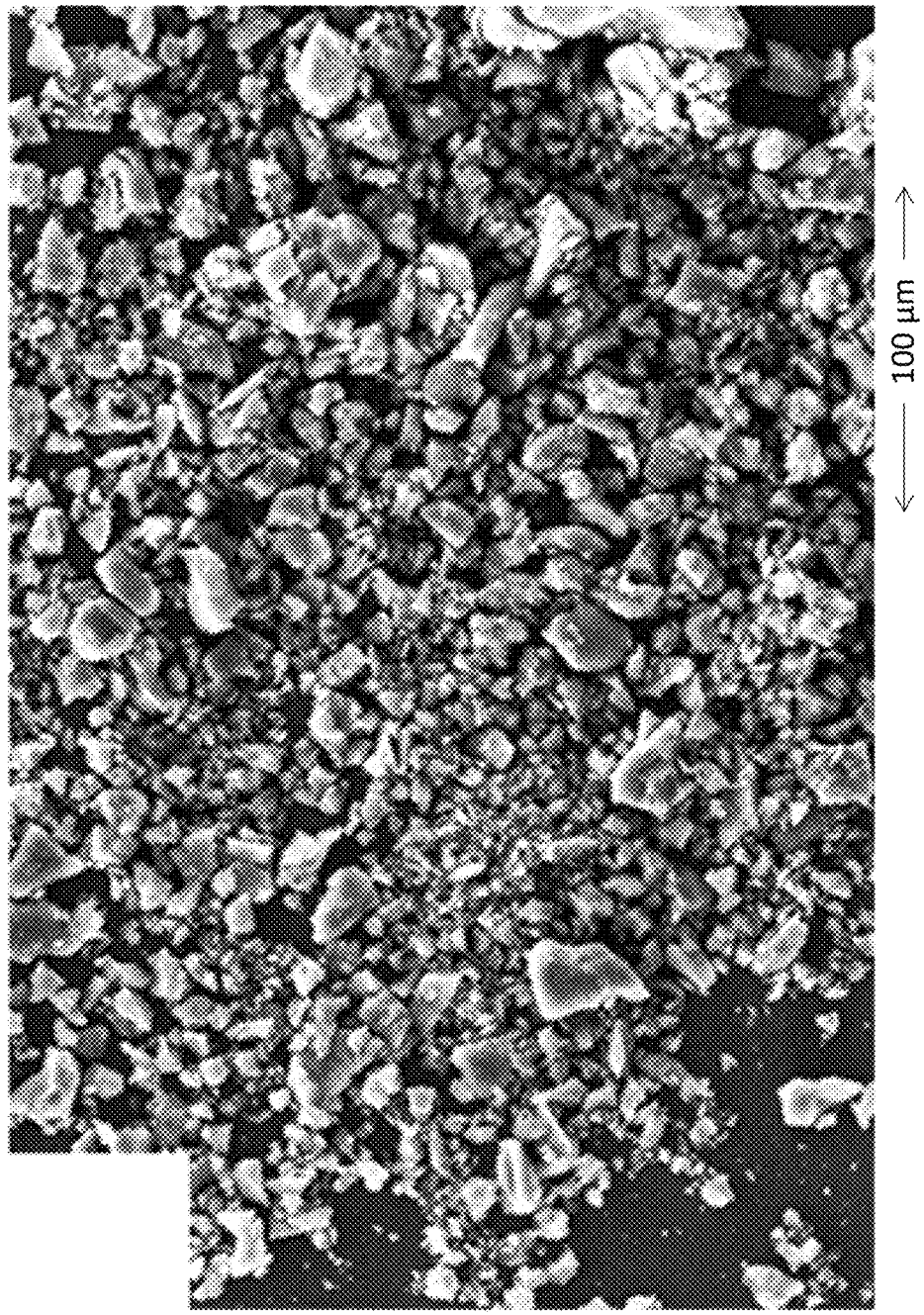

FIG. 35 is an SEM image of Fh particles prior to use in a system for arsenite removal.

Figure 36:
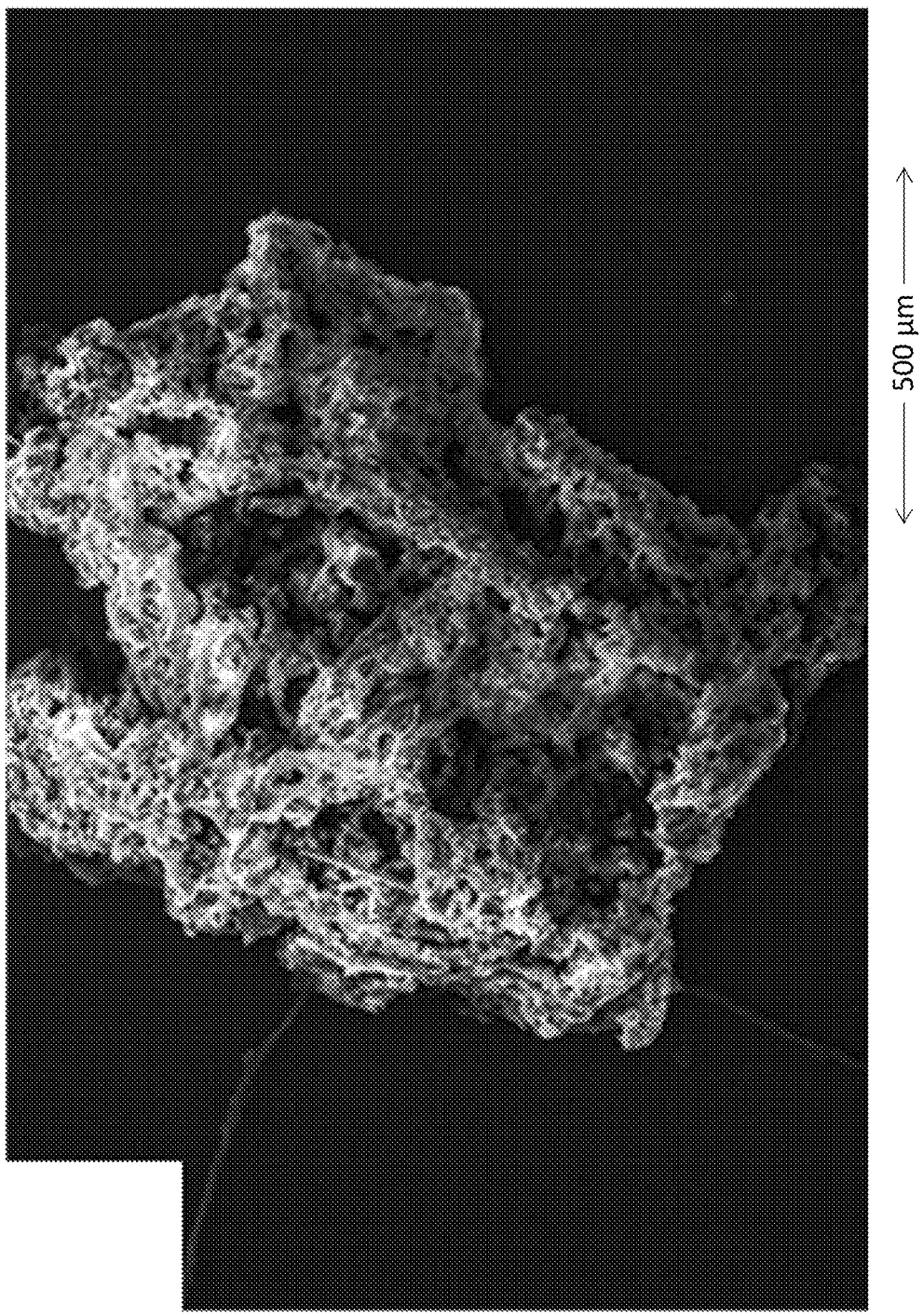

FIG. 36 is an SEM image of Fh particles after use in a system for arsenite removal.

DETAILED DESCRIPTION

It is to be understood that the Figures and descriptions of the present invention have been simplified to illustrate elements that are relevant for a clear understanding of the present invention, while eliminating, for the purpose of clarity, many other elements used in water purification. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

As used herein, each of the following terms have the meanings associated with it as specified below. Unless defined otherwise, all technical and scientific terms used herein generally have the same meaning as commonly understood by one of ordinary skill in the art to which this invention belongs.

The articles "a" and "an" are used herein to refer to one or more than one (i.e. to at least one) of the grammatical object of the article. By way of example, "an element" means one element or more than one element.

As used herein, the term "about" will be understood by persons of ordinary skill in the art and will vary to some extent depending on the context in which it is used. As used herein when referring to a measurable value such as an amount, a temporal duration, and the like, the term "about" is meant to encompass variations of ±20% or +10%, more preferably ±5%, even more preferably ±1%, and still more preferably ±0.1% from the specified value, as such variations are appropriate to perform the disclosed methods.

The terms "fluid" or "liquid medium" are used herein to refer to a substance which is in the form of a liquid at ambient temperature or room temperature. Non-limiting examples of fluid include: water, blood, blood serum, body fluids, oils, milk, and any combination thereof.

The term "water" is used herein to preferably refers to water having a total organic carbon content of at least 4 ppm, or at least 5 ppm, or at least 10 ppm, or at least 50 ppm, or at least 100 ppm, or at least 500 ppm, or at least 1000 ppm. Alternatively, the term "water" may refer to wastewater from various sources, ocean or sea water, river water, etc. In addition, the term "purified water" as used herein refers to water having a total organic carbon content of less than 10 ppm, preferably less than 5 ppm, preferably less than 4 ppm, preferably less than 3 ppm, preferably less than 2 ppm, preferably less than 1 ppm.

The term "membrane" is used herein to refer to a film capable of performing separations. The separation may be absolute (i.e., non-permeable membrane), selective (i.e., semi-permeable membrane), or limited (i.e., permeable membrane).

The terms "filter press" or "plate and frame filter press" are used herein to refer to an apparatus for physical separation of solids and liquids. A filter press generally comprises multiple filter plates arranged in parallel, such that when a slurry or suspension is passed through the filter press, solids are retained on the filter plates and liquid passes through. Filter presses are well known in the art and are described in more detail below.

The terms "filter" or "filter medium" are used herein to refer to any medium suitable for physical separation of liquids and solids. Filter presses generally comprise filter plates having a filter medium disposed thereon. Filter medium may include substrates having pores sized to exclude passage of solid particles, while allowing passage of smaller liquid molecules (e.g., filter cloths, membranes and the like). Filter medium also includes substrates comprising a plurality of particles, such that the particles serve as a physical barrier to the passage of other solid particles (e.g., diatomaceous earth and the like). Non-limiting examples of filter media include: PES (polyethersulfone) membranes, cellulose, cellulose acetate and regenerated cellulose membranes (i.e., typical paper filters), polypropylene membranes/cloth, Teflon and other fluoropolymer (hydrophilic and hydrophobic) membranes, glass fibers or fritted glass, other polymer membranes (e.g., polyester), metal mesh, charcoal, powdered activated carbon (PAC), graphite, graphene, graphene oxide, manganese oxides ($MnO_x$), manganese sulfides ($MnS_x$), molybdenum oxides ($MoO_x$), molybdenum sulfides ($MoS_x$), silicon oxides ($SiO_x$), silicon sulfides ($SiS_x$), aluminum oxides ($Al_yO_z$), aluminum sulfides ($Al_yS_z$), boron oxides ($B_yO_z$), zeolites, tungsten diselenide ($WSe_2$), niobium diselenide ($NbSe_2$), boron nitride (BN), tungsten sulfide ($WS_2$), phosphorene ($PR_3$), tin (Sn), and transition metal di-chalcogenides.

The phrase "passing contaminated fluid through a membrane" is used herein to refer to a process whereby the contaminated fluid from an upstream source, e.g. a wastewater tank, etc. is brought into contact with an inner semi-permeable membrane, and preferably a pressure and/or stirring is applied to force the contaminated fluid through the inner semi-permeable membrane. The pressure may be a positive pressure, which is provided by, for example, a positive displacement pump that is located upstream of and fluidly connected to the transparent section of the pipe. Alternatively, the pressure may be a negative pressure, which is provided by, for example, a vacuum pump that is located downstream of and fluidly connected to the outlet of the filter housing. Each of the positive or negative pressure may be in a range of 1 to 10 bars, preferably 2 to 8 bars, preferably about 4 bars.

The term "nanomaterial" is used herein to refers to a material having at least one dimension on the order of nanometers (e.g. between about 1 and 100 nanometers). Nanomaterials include, but are not limited to, nanoparticles, nanocrystals, nanowires, nanorods, nanoplates, nanotubes and the like.

The terms "nanoparticle" or "nanocrystal" are used herein to refer to a particle having at least one diameter on the order of nanometers (e.g. between about 1 and 100 nanometers).

The term "nanowire" is used herein to refer to a wire-like structure having at least one diameter on the order of nanometers (e.g. between about 1 and 100 nanometers) and an aspect ratio greater than or equal to 10:1. The "aspect ratio" of a nanowire is the ratio of the actual length (L) of the nanowire to the diameter (D) of the nanowire.

The term "nanoplate" is used herein to refer to a plate-like structure having at least one dimension on the order of nanometers (e.g. between about 1 and 100 nanometers) and an aspect ratio less than or equal to 1:5.

The term "nanotubes" is used herein to refer to cylindrical structures having at least one diameter on the order of nanometers (e.g. between about 1 and 100 nanometers). Nanotubes generally have an aspect ratio greater than or equal to 10:1.

Exemplary nanotubes include carbon nanotubes and silicon nanotubes.

The term "nanorod" is used herein to refer to a rod-like structure having at least one diameter on the order of nanometers (e.g. between about 1 and 100 nanometers) and an aspect ratio less than 10:1.

The term "2D material" is used herein to refer to a material that, within each sub-layer, tends to form strong bonds such as covalent bonds, whereas between sub-layers, tends to form relatively weaker bonds such as Van der Waals bonds. Electrons in each sub-layer of these materials are free to move in the two-dimensional plane, but their motion in the third dimension is restricted and governed by quantum mechanics.

Graphene is an example of a "2D material" in which each sub-layer has a thickness of only a single atom. Molybdenum disulfide ($MoS_2$) is an example of a "2D material" in which each sub-layer has three internal monolayers: a middle monolayer of Mo, sandwiched between upper and lower monolayers of S. The bonds between the Mo atoms and the S atoms are covalent, whereas bonds between the lower S level of one layer and the upper S level of the layer below it are Van der Waals bonds. Other examples of "2D materials" include tungsten diselenide ($WSe_2$), niobium diselenide ($NbSe_2$), boron nitride (BN), tungsten sulfide ($WS_2$), phosphorene ($PR_3$), tin (Sn), and the transition metal di-chalcogenides. A "2D material layer" typically has a thickness of less than one nanometer. Those 2D materials which are electrically conductive are of particular interest herein.

The terms "adsorbent" or "nanoadsorbent" are used herein to refer to a substance which has the ability to condense or hold molecules of other substances on its surface or in its inner structure, an activity often referred as "adsorbing" or "absorbing". Non-limiting examples of adsorbent include: activated carbon, alumina, bauxite, charcoal, zeolites, silica gel, molecular sieves, activated clays, bauxite, and mixtures thereof. The present invention is not limited to any specific adsorbents. Although there are many different adsorbents and there are various trace contaminants, it is believed that any trace contaminant can be in principle entrapped by a properly-chosen adsorbent. Choosing a proper adsorbent for a given contaminant is well within the ordinary skill of the artisans in the field. One of ordinary skill in the art can make an initial choice based on their knowledge and experience (for example, weighing the factors such as the molecular size of the contaminant and the pore size of an adsorbent as well as electronic charges it carries) and then conduct tests to determine the actual effectiveness, and the effective amount, of the chosen adsorbent against a given contaminant. One of ordinary skill in the art may need to repeat the process until a proper adsorbent is found. One of the tests for finding an effective adsorbent against adduct formation is described herein and can be adopted by people skilled in the art to determine the actual effectiveness of any adsorbent, currently existing or to be developed in the future.

The terms "microbe" and "microorganism" are used herein to refer to an organism that is too small to be visible with the naked eye. A microorganism can be formed by a single cell or by a small number of cells. Non-limiting examples of microorganisms include: bacteria, (Archaea, Eubacteria), yeast, fungi, parasites and for the purposes of this disclosure, shall be understood to include viruses. Bacteria and Protozoa are examples of microorganisms that comprise a single cell. Some microorganism (e.g., fungi) cycle through two or more developmental stages ranging from a multi-cellular organism to a single cell, both of which are encompassed by the term "microbe" and the term "microorganism". Furthermore, both terms also refer to the spores of fungi and similar devices of reproduction derived from other organisms, provided they contain the genetic information of the microbe. Non-limiting examples of parasites include: multi-cellular organisms, such as Cestodes, Tremades, or Nematodes.

The term "viruses" is used herein to refer to further examples of microorganisms and includes enveloped and non-enveloped viruses as well as bacteriophages. The term "viruses" also includes infectious nucleic acid molecules, such as those of viroids, which are not associated with a coat but are capable of replicating themselves.

The term "species of microorganism" is used herein to refer to a taxonomically and/or genetically distinct group of microorganism. Individual species of microorganisms obtained from a subject, such as a human, animal or plant subject, may exist in various relationships with respect to the subject (or host). For example, the microorganism can be a "symbiotic microorganism" that exists in a relationship with its host that provides a benefit to both the microorganism and the host, that is, a mutually beneficial relationship. The microorganism also can be a "commensal microorganism" that exists in a relationship that is beneficial to the microorganism and neither benefits nor harms the host. Alternatively, the microorganism can be a "parasitic microorganism" that derives benefit from its host at the expense of or detriment to the host. Additionally, a microorganism can be a "pathogenic microorganism" that causes or is capable of causing a disease state or condition in the host.

The term "predominant species" (for example, predominant species of microorganism) refers to one or more species that is/are numerically more frequent than other species in a mixed sample or population. For example, a predominant species may be the most numerically frequent species in a mixed sample or population, or a predominant species may be one of several numerically frequent species present in a mixed sample or population. In an embodiment, a predominant species is at least 10% of the mixed sample or population. For example, a predominant species can be at least 20%, or at least 30%, frequently greater than about 40%, or greater than 50% of the mixed population. In some cases, the predominant species is often than about 60%, sometimes greater than about 70%, and can be greater than 80% or even 90% of the mixed sample or population. In another embodiment, a predominant species is at least 2× as prevalent in the mixed sample as another species of microorganism. Alternatively, the predominant species is at least 3× as frequent in the mixed sample as other organisms. In some cases, the predominant species is at least 4×, or at least about 5×, or even as much as 10× as frequent in the mixed sample or population than another species of microorganism.

The terms "microbiota" and "microflora" are used herein to refer to an assemblage of microorganism localized to a distinct environment.

The term "microbial community" is used herein to refer to one or more microbial populations found together in a shared environment. For example, a shared environment can be a defined site or location on or in a subject (e.g., a host), or can be an environmental site or location not associated with a subject. Thus, a shared environment can be a specific organ, tissue, or site or location, such as soil, water, or another environmental source not pertaining to a particular subject (such as a human subject).

The term "microbial profile" is used herein to refer to a set of the species and/or strains of microorganisms present in a sample of microorganisms. To the extent that a sample of microorganisms is obtained from, and corresponds to the species found in, a shared environment, the microbial profile details the species present in a microbial community.

The term "consensus profile" is used herein to refer to the species common to multiple samples with similar microbial profiles. That is, a consensus profile includes the species of microorganisms that are common to each of multiple samples, which may or may not have additional unshared species.

The term "aspect ratio" of a nanomaterial is used herein to refer to the ratio of the actual length (L) of the nanomaterial to the diameter (D) of the nanomaterial. Aspect ratio is expressed as L:D.

The term "actual length" of a nanomaterial, for example a nanowire, is used herein to refer to the distance between the two distal ends of a nanomaterial as traced through the backbone of the nanomaterial as measured by TEM in bright field mode at 5 keV.

The term "diameter" of a nanomaterial is used herein to refer to a measurement of an axis perpendicular to the axis of nanomaterial's actual length (i.e. perpendicular to the nanowire's or nanorod's backbone). The diameter of a nanomaterial will vary from narrow to wide as measured at different points along the nanomaterial backbone. As used herein, the diameter of a nanomaterial is the most prevalent (i.e. the mode) diameter.

The term "effective length" of a nanowire is used herein to refer to the shortest distance between the two distal ends of a nanowire as measured by transmission electron microscopy (TEM) in bright field mode at 5 keV. "Average effective length" refers to the average of the effective lengths of individual nanowires within a plurality of nanowires.

The term "pipe" is used herein to refer to a means for carrying a fluid or a liquid stream, e.g. a water stream. The pipe may have a circular, rectangular, triangular, elliptical, or rectilinear cross-section. Preferably, the pipe has a circular cross-section with a diameter in the range of 10 to 100 mm, preferably 20 to 90 mm, preferably 30 to 80 mm, preferably 40 to 60 mm, preferably about 50 mm. The pipe may have a uniform cross-section, wherein a cross-sectional area is substantially the same along the length of the pipe, or may have a non-uniform cross-section, wherein a cross-sectional area is not the same along the length of the pipe. However, a cross-sectional area of the pipe along the transparent section is preferably substantially the same.

The term "organic" is used herein to refer to polymeric materials as well as small molecule organic materials and biological macromolecules (e.g., proteins, nucleic acids, etc.). For example, preferred small organic molecules range in size from approximately 10 Da up to about 5000 Da, more preferably up to 2000 Da, and most preferably up to about 1000 Da.

The term "inorganic" is used herein to refer to a substance comprising a metal element. Typically, an inorganic substance (e.g., nanowire) includes one or more metals in its elemental state, or more preferably, a compound formed by a metal ion ($M^{n+}$, wherein n is 1, 2, 3, 4, 5, 6 or 7) and an anion ($X^{m-}$, m is 1, 2, 3 or 4) which balance and neutralize the positive charges of the metal ion through electrostatic interactions. Non-limiting examples of inorganic compounds include oxides, hydroxides, oxyhydroxides, halides, nitrates, oxynitrates, sulfates, carbonates, oxycarbonates, phosphates, acetates, oxalates, and combinations thereof, of metal elements.

The term "salt" is used herein to refer to a compound comprising negative and positive ions. Salts are generally comprised of cations and counter ions or anions and counter ions.

The term "oxide" is used herein to refer to a metal compound comprising oxygen. Examples of oxides include, but are not limited to, metal oxides ($M_xO_y$), metal oxyhalides ($M_xO_yX_z$), metal oxynitrates ($M_xO_y(NO_3)_z$), metal phosphates ($M_x(PO_4)_y$), metal oxycarbonates ($M_xO_y(CO_3)_z$), metal carbonates, metal oxyhydroxides ($M_xO_y(OH)_z$) and the like, wherein x, y and z are numbers from 1 to 100.

The term "contaminant" or "contaminating agent" is used herein to refer to an impurity added to or incorporated within a contaminated liquid medium. A contaminant may comprise any organic compound, any inorganic compound, and any element from the periodic table.

The term "bulk material" is used herein to refer to a material prepared by traditional techniques, for example by milling or grinding large particles to obtain smaller/higher surface area particles. Bulk materials are prepared with minimal control over the size and/or morphology of the material.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to purification filters, kits, and systems comprising tubular membrane filters and methods of purification of various contaminated fluids using said purification filters, kits, and systems. The present invention also related to multi-use flow-through fluid filters.

Purification Filters

Figure 1:
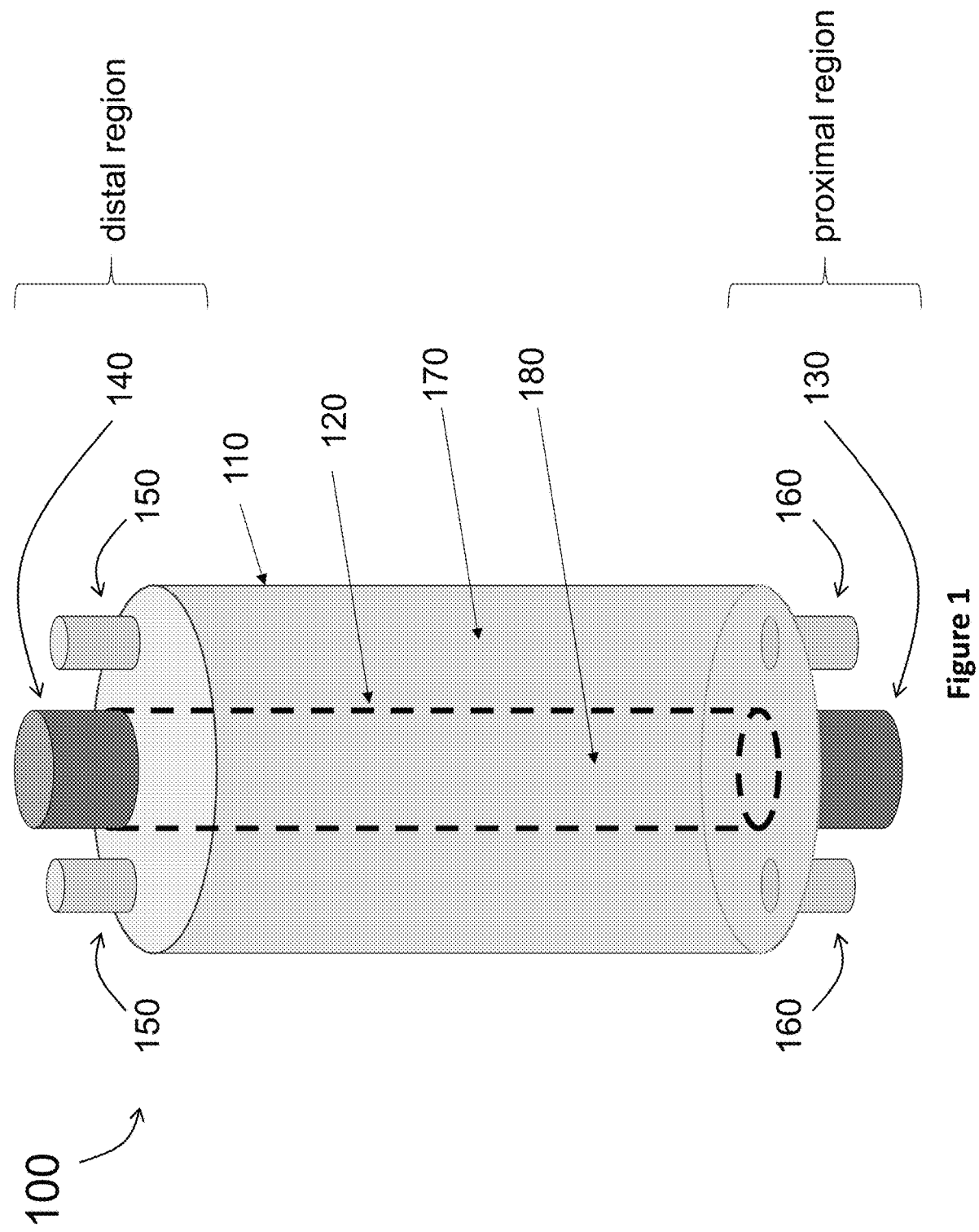
FIG. 1 depicts exemplary filter 100.

The present invention relates to a fluid purification filter. Exemplary fluid purification filter 100 is presented in FIG. 1. In one aspect, the filter comprises tubular housing 110, a tubular membrane 120, contaminated fluid sample inlet 130, contaminated fluid sample outlet 140, a purification material inlet 150, and purification material outlet 160. In one embodiment, the tubular housing has a proximal end, a distal end, and lumen 170 therethrough. In one embodiment, tubular membrane 120 has a proximal end, a distal end, and membrane lumen 180 therethrough. In one embodiment, the tubular membrane has a proximal end, a distal end, and a lumen therethrough. In one embodiment, tubular membrane 120 is positioned within lumen 170 of housing 110. In one embodiment, contaminated fluid sample inlet 130 is fluidly connected to the proximal region of membrane 120. In one embodiment, contaminated fluid sample outlet 140 is fluidly connected to the distal region of membrane 120. In one embodiment, contaminated fluid sample inlet 130 and contaminated fluid sample outlet 140 create a sample flow-path from the sample inlet through membrane lumen 180 to the sample outlet. In one embodiment, purification material inlet 150 is fluidly connected to a distal region of housing lumen 170. In one embodiment, purification material outlet 160 is fluidly connected to a proximal region of housing lumen 170. In one embodiment, purification material inlet 150 and purification material outlet 160 create a purification material flow-path from the purification material inlet through housing lumen 170 to the purification material outlet. In one embodiment, the direction of the sample flow-path is in the opposite direction of the purification material flow-path.

In one embodiment, tubular housing 110 is non-permeable. In one embodiment, the tubular housing is non-permeable to any or all of a fluid, a contaminant, and/or a purification material.

Tubular housing 110 may comprise any material known in the art, including, but not limited to, organic polymers, inorganic polymers, homopolymers, copolymers, thermoplastics, thermosets, glass, quartz, ceramic, silica, alloy, metal alloy, stainless steel, stainless steel alloy, aluminum, aluminum alloy, aluminum oxide, copper, copper alloy, titanium, titanium alloy, brass, plastic, or any combination thereof. Exemplary plastics include, but are not limited to, polyolefins, polyethylene, high-modulus polyethylene (HMPE), polypropylene, polybutylene, polybutene, polybutadiene, polybutylene terephthalate (PBT), polyethylene terephthalate (PET), polytetrafluoroethylene (PTFE), polyvinylidene fluoride (PVDF), polycyclopentadiene (PCP), hydrogenated polycyclopentadiene (HCPC), polyetherimide (PEEK), polystyrene (PS), polyurethane (PU), polycarbonate (PC), polyacrylate, polymethacrylate, poly(methyl) methacrylate, polyoxymethylene, polylactic acid, polyether ether ketone, polyvinyl ether, polyvinyl chloride (PVC), chlorinated polyvinyl chloride, acrylonitrile butadiene styrene (ABS), polyethylene vinyl acetate (PEVA), styrene-butadiene copolymer, fluorinated polymer, and combinations thereof.

In one embodiment, tubular membrane 120 is a non-permeable membrane. In one embodiment, the tubular membrane is a semi-permeable membrane. In one embodiment, the tubular membrane is a permeable membrane. In one embodiment, the tubular housing is a pipe.

In various embodiments, tubular membrane 120 has a circular, rectangular, triangular, elliptical, or rectilinear cross-section. In one embodiment, the tubular membrane has a uniform cross-section area. In one embodiment, the cross-sectional area is substantially the same along the length of the pipe. In one embodiment, the tubular membrane has a non-uniform cross-section area. In one embodiment, the cross-sectional area is not the same along the length of the pipe.

In various embodiments, tubular membrane 120 has a circular cross-section with a diameter in the range of 10 mm to 1,000 mm. In one embodiment, the tubular membrane has a circular cross-section with a diameter in the range of 20 to 90 mm. In one embodiment, the tubular membrane has a circular cross-section with a diameter in the range of 30 to 80 mm. In one embodiment, the tubular membrane has a circular cross-section with a diameter in the range of 40 to 60 mm. In one embodiment, the tubular membrane has a circular cross-section with a diameter of about 50 mm.

In one embodiment, tubular membrane 120 is permeable to at least one fluid. In one embodiment, the tubular membrane is permeable to at least one contaminant. In one embodiment, the tubular membrane is permeable to at least one fluid and at least one contaminant. In one embodiment, the tubular membrane is non-permeable to at least one purification material.

In one embodiment, tubular membrane 120 is permeable to a material with a molecular weight of at most 1,000,000 kDa. In one embodiment, the tubular membrane is permeable to a material with a molecular weight of at most 10,000 kDa. In one embodiment, the tubular membrane is permeable to a material with a molecular weight of at most 1,000 kDa. In one embodiment, the tubular membrane is permeable to a material with a molecular weight of at most 100 kDa. In one embodiment, the tubular membrane is permeable to a material with a molecular weight of at most 50 kDa. In one embodiment, the tubular membrane is permeable to a material with a molecular weight of at most 7.2 kDa. In one embodiment, the tubular membrane is permeable to a material with a molecular weight of at most 1 kDa. In one embodiment, the tubular membrane is permeable to a material with a molecular weight of at most 800 Da. In one embodiment, the tubular membrane is permeable to a material with a molecular weight of at most 250 Da. In one embodiment, the tubular membrane is permeable to a material with a molecular weight of at most 100 Da. In one embodiment, the tubular membrane is permeable to a material with a molecular weight of at most 50 Da. In one embodiment, the tubular membrane is permeable to a material with a molecular weight of at most 40 Da. In one embodiment, the tubular membrane is permeable to a material with a molecular weight of at most 30 Da. In one embodiment, the tubular membrane is permeable to a material with a molecular weight of at most 25 Da. In one embodiment, the tubular membrane is permeable to a material with a molecular weight of at most 20 Da. In one embodiment, the tubular membrane is permeable to a material with a molecular weight of at most 19 Da.

In one embodiment, tubular membrane 120 comprises a cation exchange membrane (CEM). In one embodiment, the tubular membrane comprises an anion exchange membrane (AEM). In one embodiment, the tubular membrane comprises an alkali anion exchange membrane (AAEM). In one embodiment, the tubular membrane comprises a proton exchange membrane (PEM). In one embodiment, the tubular membrane comprises a charge mosaic membrane (CMM). In one embodiment, the tubular membrane comprises a bipolar membrane (BPM). In one embodiment, the tubular membrane comprises at least one organic polymer. In one embodiment, the tubular membrane comprises an inorganic polymer. In one embodiment, the tubular membrane comprises aa combination of organic polymers and inorganic polymers. In one embodiment, the tubular membrane comprises homopolymers, copolymers, block copolymers, thermoplastic, thermosets, and/or combinations thereof. In one embodiment, the tubular membrane comprises a material selected from the group consisting of a nylon, cellulose, cellulose ester, fluorinated polymer, and any combination thereof.

In one embodiment, the inner fluid inlet is downstream of the contaminated water source. In one embodiment, the outer fluid outlet is downstream of the purification material source.

Method of Fluid Purification

Figure 2:
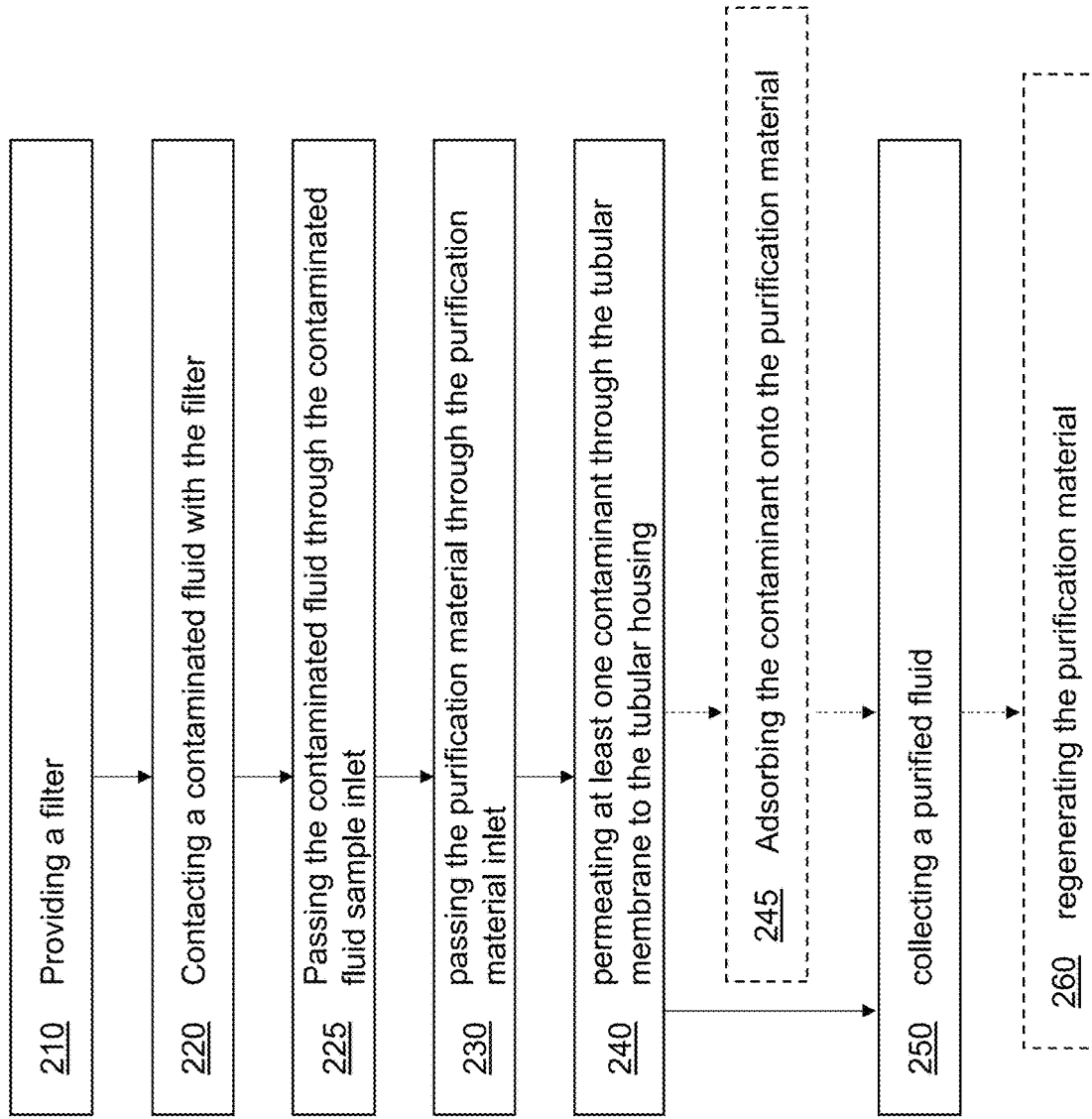
FIG. 2 depicts exemplary method 200.

In one aspect, the present invention relates in part to a method of purifying a contaminated fluid. Exemplary method 200 is provided in FIG. 2. In step 210, a filter is provided. In step 220, a contaminated fluid is contacted with the filter. In step 225, the contaminated fluid is passed through the contaminated fluid sample inlet. In step 230, a purification material is passed through the purification material inlet. In step 240, at least one contaminant is permeated through the tubular membrane to the housing lumen. In step 250, a purified fluid is collected.

In one embodiment, the step of permeating the at least one contaminant through the tubular membrane to the tubular housing further comprises step 245 in which the contaminant is adsorbed onto the purification material. In one embodiment, the step of permeating the step of permeating the at least one contaminant through the tubular membrane to the tubular housing further comprises the step of separating the contaminated fluid into a permeate, said permeate comprising the at least one contaminant, and a retentate. In one embodiment, the permeate is contacted with the purification material such that the at least one contaminant is adsorbed onto the purification material.

In one embodiment, the tubular filter is any tubular filter disclosed herein. In one embodiment, the tubular filter comprises a horizontally-oriented tubular membrane. In one embodiment, tubular filter comprises a vertically-oriented tubular membrane.

In one embodiment, the step of passing the contaminated fluid through the tubular filter comprises the step of passing the contaminated fluid through into the inner inlet, through the tubular membrane, and out the inner outlet. In one embodiment, the at least one contaminant permeates the tubular membrane. In one embodiment, the contaminant is transferred from the tubular membrane to the region between the tubular housing and the outer surface of the tubular membrane.

In one embodiment, the step of contacting the permeate with the purification material further comprises the step of passing the purification material through the region between the tubular housing and the outer surface of the tubular membrane. In one embodiment, the flow of the purification material is countercurrent to the flow of the contaminated fluid. In one embodiment, the flow of the purification material is cocurrent to the flow of the contaminated fluid.

In one embodiment, no pressure loss is observed during the operation of the filter.

In one embodiment, the step of contacting the permeate with the purification material further comprises the step of circulating the purification material around the tubular membrane. In one embodiment, the purification material is stirred. In one embodiment, the mixture of the purification material is shaken. In one embodiment, the purification material is dispersed homogeneously.

In one embodiment, the purification material is selected such that it is capable of absorbing at least a portion of at least one contaminant present in the contaminated fluid.

In one embodiment, the purification material comprises a loose powder. In one embodiment, the purification material is a tablet. In one embodiment, the purification material is a capsule. In one embodiment, the purification material is dissolved in a solvent. In one embodiment, the purification material is dispersed in a solvent. In one embodiment, the purification material is suspended in a solvent. In one embodiment, the purification material forms an aggregate in the solvent. In one embodiment, the purification material does not form an aggregate in the solvent.

In one embodiment, the purification material is a nanoadsorbent. In one embodiment, the purification material is an adsorbent. In one embodiment, the purification material is a microorganism. In one embodiment, the purification material is a bacterium. In one embodiment, the purification material is a bacterial community. In one embodiment, the purification material is a bacterial slurry. In one embodiment, the purification material is any combination of a nanomaterial, a nanoadsorbent, an adsorbent, a microorganism, a bacterium, a bacterial community, and/or a bacterial slurry.

Exemplary nanomaterials include, but are not limited to, charcoal, activated carbon, powdered activated carbon (PAC), graphite, graphene, graphene oxide, manganese oxides ($MnO_x$), iron oxides ($Fe_yO_z$), manganese sulfides ($MnS_x$), molybdenum oxides ($MoO_x$) such as birnessite, molybdenum sulfides ($MoS_x$), silicon oxides ($SiO_x$), silicon sulfides ($SiS_x$), aluminum oxides ($Al_yO_z$), aluminum sulfides ($Al_yS_z$), boron oxides ($B_yO_z$), zeolites, tungsten diselenide ($WSe_2$), niobium diselenide ($NbSe_2$), boron nitride (BN), tungsten sulfide ($WS_2$), phosphorene ($PR_3$), tin (Sn), transition metal di-chalcogenides, alumina, bauxite, silica gel, molecular sieves, activated clays, bauxite, and any combination thereof.

In various embodiments, the nanomaterial may be in any form known to one of skill in the art. In one embodiment, the nanomaterial comprises a nanoparticle. In one embodiment, the nanomaterial comprises a nanocrystal. In one embodiment, the nanomaterial comprises a nanowire. In one embodiment, the nanomaterial comprises a nanorod. In one embodiment, the nanomaterial comprises a nanoplate. In one embodiment, the nanomaterial comprises a nanotube. In one embodiment, the nanomaterial comprises a nanofiber. In one embodiment, the nanomaterial comprises a planar material. In one embodiment, the planar material is a 2D material.

In one aspect, the nanomaterial has at least one dimension on the order of nanometers. In various embodiments, the nanomaterial has at least one dimension between about 1 and 100 nm. In one embodiment, the nanomaterial has at least one dimension of about 1 nm. In one embodiment, the nanomaterial has at least one dimension of about 5 nm. In one embodiment, the nanomaterial has at least one dimension of about 10 nm. In one embodiment, the nanomaterial has at least one dimension of about 20 nm. In one embodiment, the nanomaterial has at least one dimension of about 30 nm. In one embodiment, the nanomaterial has at least one dimension of about 50 nm. In one embodiment, the nanomaterial has at least one dimension of about 75 nm. In one embodiment, the nanomaterial has at least one dimension of about 90 nm. In one embodiment, the nanomaterial has at least one dimension of about 100 nm.

In one aspect, the purification material has a molecular weight of at least 20 Da. In one embodiment, the purification material has a molecular weight of at least 200 Da. In one embodiment, the purification material has a molecular weight of at least 250 Da. In one embodiment, the purification material has a molecular weight of at least 300 Da. In one embodiment, the purification material has a molecular weight of at least 400 Da. In one embodiment, the purification material has a molecular weight of at least 500 Da. In one embodiment, the purification material has a molecular weight of at least 1 kDa. In one embodiment, the purification material has a molecular weight of at least 2.5 kDa. In one embodiment, the purification material has a molecular weight of at least 8 kDa. In one embodiment, the purification material has a molecular weight of at least 10 kDa. In one embodiment, the purification material has a molecular weight of at least 72 kDa. In one embodiment, the purification material has a molecular weight of at least 500 kDa. In one embodiment, the purification material has a molecular weight of at least 1,000 kDa. In one embodiment, the purification material has a molecular weight of at least 10,000 kDa. In one embodiment, the purification material has a molecular weight of at least 1,000,000 kDa In one embodiment, the purification material has a molecular weight of at least 100,000,000 kDa.

In one embodiment, the purification material comprises an additive. In one embodiment, the additive serves to increase the adsorption capacity.

In one embodiment, the purification material comprises at least one surfactant. In one embodiment, the surfactant prevents aggregation of the purification material. In one embodiment, the surfactant is ingestible. In one embodiment, the ingestible surfactant is FDA-approved. In various embodiments, the surfactant is polyethoxylate sorbitan surfactants (such as T-MAZφ-60, T-MAZ® 20, polyoxyethylene (20) sorbitan monostearate, and polyoxyethylene (20) sorbitan tristearate), sorbitan monolaurate, sorbitan monooleate, sorbitan trioleate, sorbitan monostearate, sorbitan tristearate, bis(2-ethylhexyl) sodium sulfosuccinate, sodium methylnaphthalene sulfonate, sodium dimethylnaphthalene sulfonate, lecithin, polyglycerol polyricinoleate (PGPR), monoglycerides, diglycerides, sodium steoryl lactylate, citric acid esters of monoglycerides and diglycerides, MYVATEX® Brand Mighty Cream, acetylated monoglycerides, glycerol monostearate, monolaurin, glyceryl hydroxystearate, glycerol triacetate, fatty acids, sucrose laurate, sucrose caprate, sucrose coprylate, diacetyl tartrate esters of monoglycerides, acetylated monoglyceride, lactylated monoglyceride, propylene glycol monoester, polyglycerol monostearate, 'Ryoto™ Sugar Ester' (sucrose fatty acid esters) and 'Ryoto™ Polyglycerol Ester' (polyglycerol fatty acid esters), sodium stearoyl lactylate, sodium stearyl fumarate, and sodium dodecyl sulfate, phosphatidylethanolamine, phosphatidylinositol, phosphatidylcholine, lysolecithin, acetylated lecithin, saponin, gum arabic, Polysorbate 20, Polysorbate 65, Polysorbate 80, capric acid, caprylic acid, lauric acid, myristic acid, oleic acid, palmitic acid, agar, alginic acid, beta glucan, carrageenan, cassia gum, chicle gum, dammar gum, gellan gum, glucomannan, guar gum, gum ghatti, gum karaya, konjac, locust bean gum, psyllium, sodium alginate, tara spinose, tragacanth, xanthan gum, quillaja, baker's yeast glycan, mastic, stearic acid, monoglycerides of fatty acids, butyric acid, potassium caprate, potassium caprylate, potassium laurate, potassium myristate, potassium oleate, potassium palmitate, sodium myristate, sodium palmitate, sodium stearate, ethyl methyl cellulose, DATEM, ethoxylated glycerides, sorbitan monostearate, Polysorbate 60, docusate, lactylated fatty acid ester of glycerol, lactylated fatty acid ester of propylene glycol, polyethylene glycol oleate, sucrose acetate isobutyrate, glycerol, sorbitan monooleate, polyethylene glycol, and cyclodextrin.

In one embodiment, the amount of surfactant in the purification material is equal to the critical micelle concentration (CMC) of the surfactant. In one embodiment, the amount of surfactant in the purification material is greater than the CMC of the surfactant. In one embodiment, the amount of surfactant is between 1.2 and 50 times the CMC of the surfactant. In one embodiment, the amount of surfactant is between 1.2 and 45 times the CMC of the surfactant. In one embodiment, the amount of surfactant is between 1.2 and 40 times the CMC of the surfactant. In one embodiment, the amount of surfactant is between 1.2 and 35 times the CMC of the surfactant. In one embodiment, the amount of surfactant is between 1.2 and 30 times the CMC of the surfactant. In one embodiment, the amount of surfactant is between 1.2 and 25 times the CMC of the surfactant. In one embodiment, the amount of surfactant is between 1.2 and 20 times the CMC of the surfactant. In one embodiment, the amount of surfactant is between 1.2 and 15 times the CMC of the surfactant. In one embodiment, the amount of surfactant is between 1.5 and 12 times the CMC of the surfactant.

In one embodiment, the contaminant source comprises a fluid. In one embodiment, the contaminant source comprises a contaminant. In one embodiment, the contaminant is an impurity in a fluid. The contaminant may be any organic compound, inorganic compound, salt, or any combination thereof. In one embodiment, the contaminant comprises an organic contaminant. In one embodiment, the organic contaminant comprises an organic compound. In one embodiment, the contaminant comprises an inorganic contaminant. In one embodiment, the inorganic contaminant comprises an inorganic compound. In various embodiments, the contaminant comprises a combination of an organic compound and an inorganic compound.

In one embodiment, the organic contaminant is a polymeric material. In one embodiment, the organic compound is a small organic molecule. In one embodiment, the small organic molecule has a size in range from approximately 10 Da up to about 5000 Da. In one embodiment, the small organic molecule has a size up to about 1000 Da. In one embodiment, the small organic molecule has a size up to 2000 Da. In one embodiment, the organic contaminant comprises a biological macromolecule such as, for example, a protein, a nucleic acid, a pharmaceutical product, an antibiotic, an organic solvent, a pesticide, or an endocrine disruptor. Additional organic contaminants include, but are not limited to, 1,1-dichloroethane, 1,1,1,2-tetrachloroethane, 1,2,3-trichloropropane, 1,3-butadiene, 1,4-dioxane, 17a-estradiol, 1-butanol, 2-methoxyethanol, 2-propen-1-ol, 3-hydroxycarbofuran, 4,4'-methylenedianiline, acephate, acetaldehyde, acetamide, acetochlor, acetochlor ethanesulfonic acid, acetochlor oxanilic acid, acrolein, alachlor ethanesulfonic acid, alachlor oxanilic acid, α-hexachlorocyclohexane, aniline, bensulide, benzyl chloride, butylated hydroxyanisole, captan, chlorate, chloromethane, clethodim, cobalt, cumene hydroperoxide, cyanotoxins, dicrotophos, dimethipin, diuron, equilenin, equilin, erythromycin, estradiol, estriol, estrone, ethinyl estradiol, ethoprop, ethylene glycol, ethylene oxide, ethylene thiourea, formaldehyde, germanium, HCFC-22, Halon 1011, hexane, hydrazine, manganese, mestranol, methamidophos, methanol, methyl bromide, methyl tert-butyl ether, metoclachlor, metolachlor ethanesulfonic acid, metolachlor oxanilic acid, molybdenum, nitrobenzene, nitroglycerin, N-methyl-2-pyrrolidone, N-nitrosodiethylamine, N-nitrosodimethylamine, N-nitroso-di-N-propylamine, N-nitrosodiphenylamine, N-nitrosopyrrolidine, nonylphenol, norethindrone, N-propylbenzene, o-Toluidine, oxirane, oxydemeton, oxyfluorfen, perfluorooctanesulfonic acid, perfluorooctanoic acid, permethrin, profenofos, quinoline, hexahydro-1,3,5-trinitro-1,3,5-triazine, sec-butylbenzene, tebuconazole, tebufenozide, tellurium, thiodicarb, thiophanate, toluene diisocyanate, tribufos, triethylamine, trphenyltin hydroxide, urethane, vanadium, vinclozolin, ziram, amoxycillin, atenolol, bezafibrate, carbamazepine, cetirizine, clofibric acid, diclofenac, felbamate, ibuprofen, bleomycin, clotrimazole, norfluoxetine, paracetamol, tamoxifen, tetracycline, sulfamethoxazole, mefenamic acid, propranolol, theophylline, trimethoprim, iopromide, bisphenol A, bispenol S, dichlorodiphenyltrichloroethane (DDT), polychlorinated biphenols, polybrominated diphenyl ethers, and phthalates.

Exemplary inorganic contaminants include any substances comprising inorganic materials, such as elemental metals or metal salts. In one embodiment, the inorganic contaminant comprises an inorganic compound or inorganic salt formed by a metal ion ($M^{n+}$, wherein n is 1, 2, 3, 4, 5, 6 or 7) and an anion ($X^{m-}$, m is 1, 2, 3 or 4). Exemplary inorganic contaminants include, but are not limited to, inorganic oxides, hydroxides, oxyhydroxides, halides, nitrates, oxynitrates, sulfates, carbonates, oxycarbonates, phosphates, acetates, oxalates, and combinations thereof. Additional inorganic contaminants include aluminum, ammonia, arsenic, barium, cadmium, chloramine, chromium, copper, fluoride, lead, nitrates, nitrites, mercury, perchlorates, radium, selenium, sulfur, silver, uranium, iron, iron oxides ($Fe_yO_z$), asbestos, perfluoroalkyl substances, polyfluoroalkyl substances (PFAS), perfluorooctanesulfonic acid (PFOS), perfluorooctanoic acid (PFOA), bacteria, viruses, potassium bicarbonate, sodium bicarbonate, phosphates, and any combination thereof.

In one embodiment, the contaminate comprises a biological contaminate. In one embodiment, the contaminate comprises a bacterium. In one embodiment, the contaminate comprises a virus. In one embodiment, the contaminate comprises a microbe. In one embodiment, the contaminate comprises a protozoan. In one embodiment, the contaminate comprises natural organic matter. Non-limiting examples of biological contaminates include: adenovirus, PR772, caliciviruses, *Campylobacter jejuni*, entovirus, *Escherichia coli*, *Helicobater pylori*, Hepatitis A virus, *Legionella pneumophila*, *Mycobacterium avium*, *Naegleria fowleri*, *Salmonella enterica*, *Shigella sonnei*, *Aeromonas hydrophila*, coxsackieviruses, cyanobacteria, echoviruses, microsporidia (such as enterocytozoon and septata), *Mycobacterium avium intracellulare*, *Acanthamoeba*, bacteriophage MS2, bacteriophage f2, and bacteriophage Qβ.

In one embodiment, the contaminated fluid comprises at least one contaminant such as any contaminant disclosed herein. In one embodiment, the fluid comprises water. In one embodiment, the fluid comprises an emulsion. In one embodiment, the contaminated fluid comprises a drinking fluid. In one embodiment, the contaminated fluid comprises a beverage. In one embodiment, the contaminated fluid comprises a bodily fluid. In one embodiment, the contaminated fluid comprises blood. In one embodiment, the contaminated fluid comprises blood serum. In one embodiment, the contaminated fluid comprises an oil. In one embodiment, the contaminated fluid comprises milk. In one embodiment, the contaminated fluid comprises an alcohol. In one embodiment, the contaminated fluid comprises a paint. In one embodiment, the contaminated fluid comprises a solvent. In one embodiment, the contaminated fluid comprises an organic solvent. In various embodiments, the contaminated fluid may comprise any combination of water, drinking fluids, beverages, blood, blood serum, oils, milk, alcohols, paint, solvents, and organic solvents.

In one aspect, the water is provided from a water source. In one embodiment, the water source is a stagnant water source. In various embodiments, the stagnant water source is a pond, wetland, puddle, or any combination thereof. In one embodiment, the water source is a flowing water source. In various embodiments, the flowing water source is a stream or river. In one embodiment, the water source is a freshwater source. In one embodiment, the water source is a salt water source.

In one embodiment, the purification material is immobilized on the outer surface of the tubular membrane. In one embodiment, the purification material is immobilized on a support. Exemplary supports may include, but are not limited to, textiles, corn husks, hemp, cellulose, paper, egg shells, grass, activated carbon, alumina, silica, ceramics, nanoparticles, carbon nanotubes, and polymers. In one embodiment, the support with immobilized purification material is used in a multi-use flow-through water filter.

Purification Kits

The present invention also relates to various purification kits. In one aspect, the kit comprises at least one purification material, at least one tubular filter, and instructional materials. In one embodiment, the tubular filter is any filter of the present invention. In one embodiment, the purification material is any purification material of the present invention.

The purification material may be in any form as described elsewhere herein. In one embodiment, the purification material is provided as a loose powder. In one embodiment, the purification material is provided in a storage container. In one embodiment, the storage container is a bottle. In one embodiment, the storage container is a pouch. In one embodiment, the storage container is a sachet. In one embodiment, the storage container is a packet. In one embodiment, the storage container is a sleeve. In one embodiment, the storage container can be torn open. In one embodiment, the storage container can be cut open.

In one embodiment, the kit includes a stirring apparatus. In one embodiment, the stirring apparatus comprises a stir bar. In one aspect, the kit comprises a surfactant. The surfactant may be one of the exemplary surfactants described elsewhere herein.

In one embodiment, the kit includes a support to immobilize the purification material. In one embodiment, the purification material is immobilized on a support. The support may be any exemplary support described elsewhere herein. In one embodiment, the purification material is contained in a filter. In one embodiment, the filter is a commercial water filter. In one embodiment, the kit contains enough of the one or more purification material for more than one use.

In one embodiment, the kit includes an instruction booklet which describes the method for using the tubular membrane kit to purify fluids. In one embodiment, the instructions include the amount of purification material to add to the tubular membrane such that it will be sufficient to purify the amount of fluid that can be put in the tubular membrane. In one embodiment, the instructions will provide advice on how to scale the amount of purification material needed to purify fluid depending on the size of the tubular membrane. In one embodiment, the instruction booklet includes information on how to use the optional surfactant and/or support. In one embodiment, the instructions include how to stir the fluid. In one embodiment, the instructions include how to shake the fluid.

In one embodiment, the kit includes a transparent bottle. In one embodiment, the bottle comprises a cap or a closure so that the bottle can be sealed. The transparent bottle may be any material that allows for the transmission of the light source through the material. Non-limiting examples of materials include: glass, plastics, such as polyethylene terephthalate, high-density polyethylene, low-density polyethylene, polyvinyl chloride, polypropylene, polystyrene, polycarbonate, or bisphenol-A.

Multi-Use Flow-Through Water Filter

The present invention also relates to multi-use flow-through water treatment filters comprising at least one purification material and at least one membrane. The purification material may be any exemplary purification materials described elsewhere herein. The membrane may be any exemplary membranes described elsewhere herein. The water treatment filter further comprises a support. Exemplary supports include, but are not limited to, carbon block, activated carbon, activated coal, ceramic, or mixtures thereof. In one embodiment, the purification material is immobilized on the support.

In one embodiment, the water treatment filter comprises an indicator that undergoes a color change or a loss of color. In various embodiments, the indicator is Chlorophyllin sodium copper salt, Tartrazine (FD&C Yellow No. 5), Allura Red AC (FD&C Red No. 40), Chromotrope FB (CI 14720, Food Red 3), Erioglaucine disodium salt (FD&C Blue No. 1), Fast Green FCF (FD&C Green No. 3), Lissamine Green B, Naphthol Green or Acid Green, Carmoisine azorubine, Amaranth, Brillant Scarlet 4R, Brillant black BN (PN), Brillant Blue FCF, Chocolate Brown HT, Beta-carotene, Bixin, Lycopene, Betanin, $TiO_2$ Anatase P25 Degussa, or any combination thereof.

In various embodiments, a concentration of the indicator is between 1 µM and 10 mM. In one embodiment, the concentration is between 1 µM and 9.5 mM. In one embodiment, the concentration is between 1 µM and 9 mM. In one embodiment, the concentration is between 1 µM and 8.5 mM. In one embodiment, the concentration is between 1 µM and 8 mM. In one embodiment, the concentration is between 1 µM and 7.5 mM. In one embodiment, the concentration is between 1 µM and 7 mM. In one embodiment, the concentration is between 1 µM and 6.5 mM. In one embodiment, the concentration is between 1 µM and 5.5 mM. In one embodiment, the concentration is between 1 µM and 5 mM. In one embodiment, the concentration is between 1 µM and 4.5 mM. In one embodiment, the concentration is between 1 µM and 4 mM. In one embodiment, the concentration is between 1 µM and 3.5 mM. In one embodiment, the concentration is between 1 µM and 3 mM. In one embodiment, the concentration is between 1 µM and 2.5 mM. In one embodiment, the concentration is between 1 µM and 2 mM. In one embodiment, the concentration is between 1 µM and 1.5 mM. In one embodiment, the concentration is between 1 µM and 1 mM.

In one embodiment, the change in color in the water source indicates that the water source has become potable. In one embodiment, the loss of color or color change indicates that the water is purified. In one embodiment, the loss of color or color change indicates that 80% to 100% of the contaminates have been removed. In one embodiment, the loss of color or color change indicates that 83% to 100% of the contaminates have been removed. In one embodiment, the loss of color or color change indicates that 85% to 100% of the contaminates have been removed. In one embodiment, the loss of color or color change indicates that 87% to 100% of the contaminates have been removed. In one embodiment, the loss of color or color change indicates that 90% to 100% of the contaminates have been removed. In one embodiment, the loss of color or color change indicates that 93% to 100% of the contaminates have been removed. In one embodiment, the loss of color or color change indicates that 95% to 100% of the contaminates have been removed. In one embodiment, the loss of color or color change indicates that 97% to 100% of the contaminates have been removed.

In one embodiment, the color change or loss of color of the indicator signifies that the water treatment filter should be regenerated. In one embodiment, the water treatment filter is regenerated by contacting the filter with a purification material. In one embodiment, the water treatment filter is contacted with a solid purification material. In another embodiment, the water treatment filter is contacted with a solution of purification material.

The water treatment filter can be used with any water source known to a person of skill in the art. The water source may be any exemplary water source described elsewhere herein. In one embodiment, the water source is contaminated. The contaminates may be any exemplary contaminates described elsewhere herein. In one embodiment, the water treatment filter is used on a faucet. In one embodiment, the water treatment filter is used in a water storage container such as a pitcher or bottle. In one embodiment, the water filter is submergible. In one embodiment, the water filter is submerged in a water source. In one embodiment, the water source flows through the water filter. In one embodiment, the water source is stirred while in contact with the water filter. In one embodiment, the water source, in contact with the water filter, is shaken.

Multi-Use Flow-Through Dialysis Filter

The present invention also relates to multi-use flow-through dialysis filters comprising at least one purification material and at least one membrane. The purification material may be any exemplary purification materials described elsewhere herein. The membrane may be any exemplary membranes described elsewhere herein. The dialysis filter further comprises a support. Exemplary supports include, but are not limited to, carbon block, activated carbon, activated coal, ceramic, or mixtures thereof. In one embodiment, the purification material is immobilized on the support.

Purification Systems

The present invention also relates to a fluid purification system. In one aspect, the present invention relates to a purification system comprising a contaminated fluid source and at least one filter. In one aspect, the filter comprises at least one purification material, at least one tubular membrane, and at least one tubular housing. In one embodiment, the filter may comprise the components described elsewhere herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the materials, devices, and kits of the present invention and practice the claimed methods. The following working examples therefore, specifically point out exemplary embodiments of the present invention, and are not to be construed as limiting in any way the remainder of the disclosure.

Example 1: Employing 2D/Nanomaterials and Membrane Technology in Water Treatment Previous studies have been conducted to make and test many nanoadsorbent for water treatment, but barely any can be used on an industrial scale for water treatment because the smaller the adsorbent, the higher adsorption capacity, but the harder it is to separate the adsorbent from treated water.

As such, the current major technical constrains of nano-technology in water treatment are: 1) separation of nanoadsorbents from treated water, which is more costly than removing contaminants; 2) unknown toxicity and fate of nanoadsorbents; 3) aggregation of nanoadsorbents in water; 4) reuse of exhausted nanoadsorbents; and 5) significant pressure loss.

This invention employs in part nanoadsorbents and membrane technology simultaneously to mitigate the following issues: 1) economic feasibility; 2) instability of nanoparticles; 3) hazardous release of used nanoparticles; 4) infeasible separation of used nanoparticles; 5) complex regeneration/reuse of used nanoparticles; 6) unclear environmental toxicity of nanomaterials; and 7) significant pressure loss or fouling.

The present invention in part provides a simultaneous use of nanoadsorbent and tubular membranes. The purification mechanism uses a design of countercurrent heat exchanger. The present setup was in part designed for removal of heavy metals and small organic compounds (lead (Pb) removal has been successfully tested).

Synthesis of Iron Oxide Nanomaterials

Figure 5:
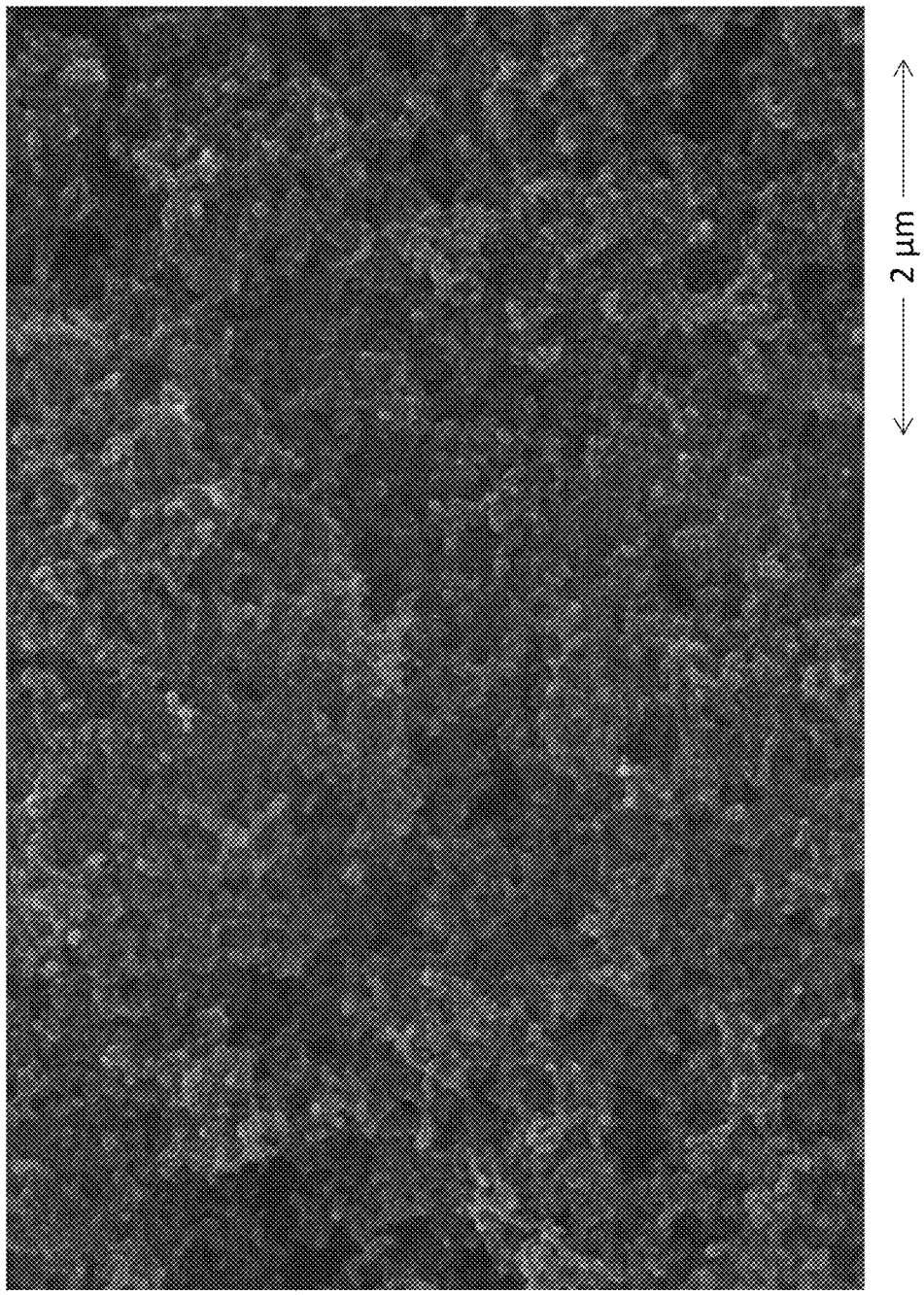
FIG. 5 depicts a scanning electron microscopy (SEM) image of iron oxide.

To synthesize iron oxide, 200 mg iron chloride was dissolved in 19.5 mL DI water, and then 500 µl of 1M aqueous sodium hydroxide was added to the solution. The solution was transferred to a 30 mL reaction vessel that was sealed with a septum cap and placed in a microwave reactor (Monowave 400, Anton Parr). The dispersion was then quickly heated to a predetermined temperature (e.g., 80° C.) during the course of approximately 5 s and the same temperature was held for 30 min. The reaction solution was then quickly cooled down to room temperature. The products (FIG. 5) were then collected via centrifugation at 6000 rpm for 10 min followed by washing with DI water.

Iron oxide materials can be produced with different sizes, morphologies, and phases. The iron precursors can be dissolved in a variety of solvents. Non-limiting examples of solvent include: water, ethanol, and dimethylformamide. Non-limiting examples of iron precursor include: iron nitrate, iron chloride, iron acetate, and iron acetylacetonate.

The pressure, microwave power, and temperature can be adjusted in the synthesis of iron oxide via a microwave-assistant hydrothermal process under high pressures.

The pH of the solution can be used to control the particle size, morphology, and phase of iron oxide materials. The pH of the solution can range from 0.1 to 14. Acids, bases, or buffers can be used to control the pH of the solution. Non-limiting examples of methods used to control the pH of the solution include the addition of sodium hydroxide, calcium hydroxide, ammonium hydroxide, hydrochloric acid, sulphuric acid, nitric acid, acetic acid, ascorbic acid, tris buffer, HEPES buffer, and any combination thereof.

Stabilizers can be used to control the particle size and morphology. The molar ratio of stabilizer to the iron precursor can range between 1:1 and 1:60. The stabilizer can be a polymer or surfactant. Non-limiting examples of stabilizer include: cetyltrimethylammonium bromide (CTAB), sodium dodecyl sulfate (SDS), poly ethylene oxide (PEO), polyoxyethylene sorbitan monolaurate (Tween), octyl phenol ethoxylate (Triton X-100), and/or polymers, such as polyvinylpyrrolidone (PVP), copolymer (e.g., poly(ethylene glycol), poly(propylene glycol), poly(ethylene glycol) triblock copolymer), polyvinyl alcohol (PVA), and any combination thereof.

Synthesis of Manganese Oxide Nanomaterials

Figure 6:
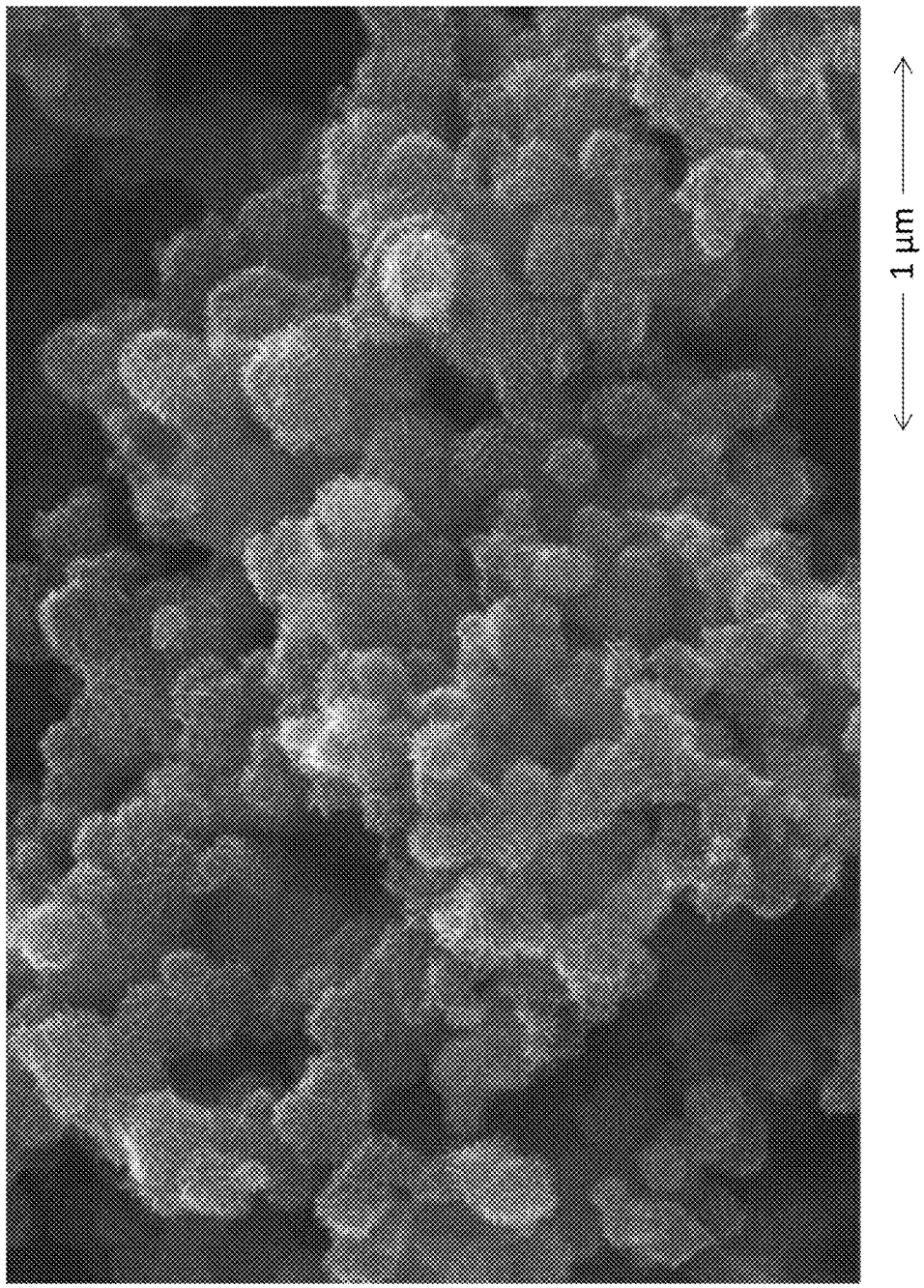
FIG. 6 depicts a scanning electron microscopy (SEM) image of manganese oxide.

To synthesize manganese oxide, 170 mg of $Mn(NO_3)_2$ and 60 mg copolymer (i.e., poly(ethylene glycol), poly(propylene glycol), poly(ethylene glycol) triblock copolymer) were dissolved in 10 mL DI water, and then 10 mL of 0.1 M aqueous $KMnO_4$ was added into the solution. The solution was transferred to a 30 mL reaction vessel that was sealed with a septum cap and placed in a microwave reactor (Monowave 400, Anton Parr). The solution was then quickly heated to a predetermined temperature (e.g., 60° C.) during the course of approximate 5 s and the same temperature was held for 30 min to complete the reaction. The reaction was then quickly cooled down to room temperature. The products (FIG. 6) were then collected via centrifugation at 6000 rpm for 10 min followed by washing with DI water.

Manganese oxide materials can be produced with different sizes, morphologies, and phases. The manganese precursors can be dissolved in a variety of solvents. Non-limiting examples of solvent include: water, ethanol, and dimethylformamide. Non-limiting examples of manganese precursor include: manganese chloride, manganese sulfate, manganese acetate, manganese nitrate, potassium permanganate, and manganese nitrate.

The pressure, microwave power and temperature can be adjusted in the synthesis of manganese oxide via a microwave-assistant hydrothermal process under high pressures.

pH of the solution can be used to control the particle size, morphology, and phase of manganese oxide materials. The pH of the solution can range from 0.1 to 14. Acids, bases, or buffers can be used to control the pH of the solution. Non-limiting examples of methods used to control the pH of the solution include the addition of sodium hydroxide, calcium hydroxide, ammonium hydroxide, hydrochloric acid, sulphuric acid, nitric acid, acetic acid, ascorbic acid, tris buffer, HEPES buffer, and any combination thereof.

Stabilizer can be used to control the particle size and morphology. The molar ratio of stabilizer to the manganese precursor can range between 1:1 and 1:60. The stabilizer can be a polymer or surfactant. Non-limiting examples of stabilizer include: cetyltrimethylammonium bromide (CTAB), sodium dodecyl sulfate (SDS), poly ethylene oxide (PEO), polyoxyethylene sorbitan monolaurate (Tween), octyl phenol ethoxylate (Triton X-100), and/or polymers, such as polyvinylpyrrolidone (PVP), copolymer (e.g., poly(ethylene glycol), poly(propylene glycol), poly(ethylene glycol) triblock copolymer), polyvinyl alcohol (PVA), and any combination thereof.

Nanomaterial Filter Prototype

The present invention provides methods for purification of various fluids, such as water or blood, wherein high concentrations of contaminants are delivered to the system by tubular membranes. The tubular membranes are permeable to the contaminants but are non-permeable to the nanoadsorbents. As such, the tubular membranes allow contaminants to leave but do not allow nanoadsorbents to enter the tubular membranes.

Figure 3A:
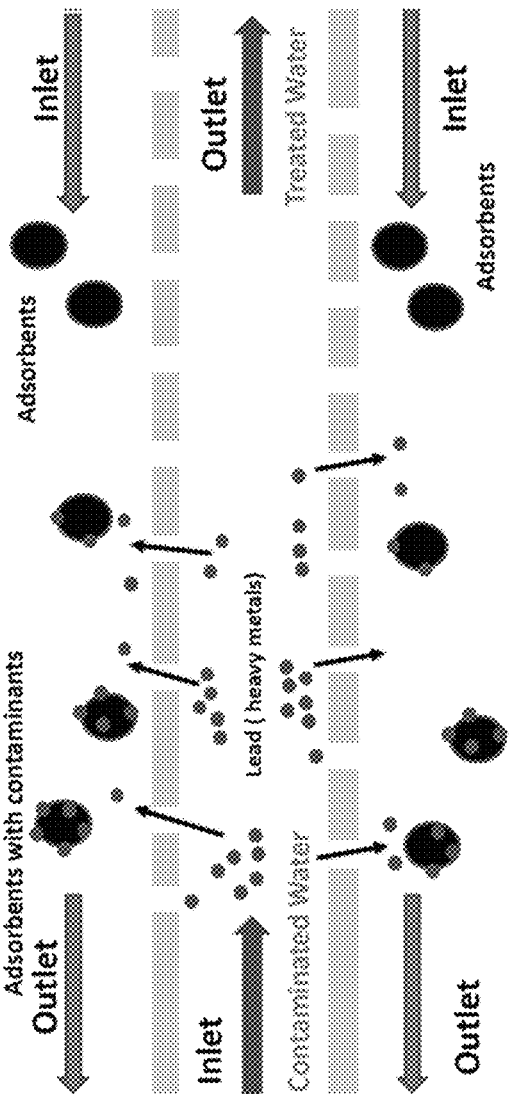
FIG. 3A and FIG. 3B, depicts a design of a purification membrane filter.
Figure 3B:
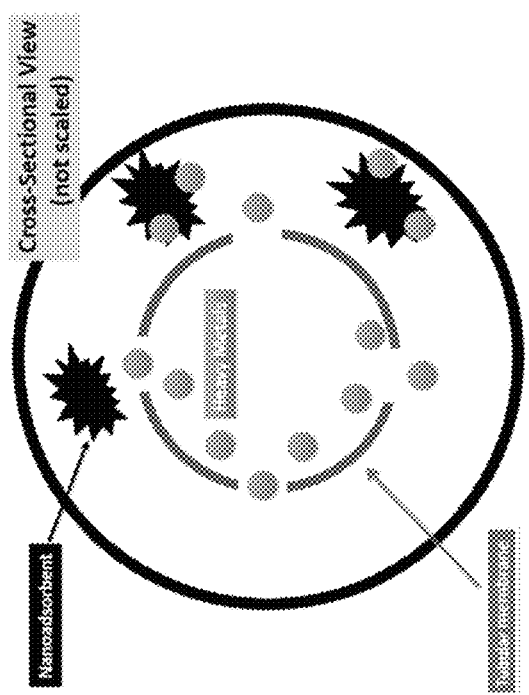
Figure 4:
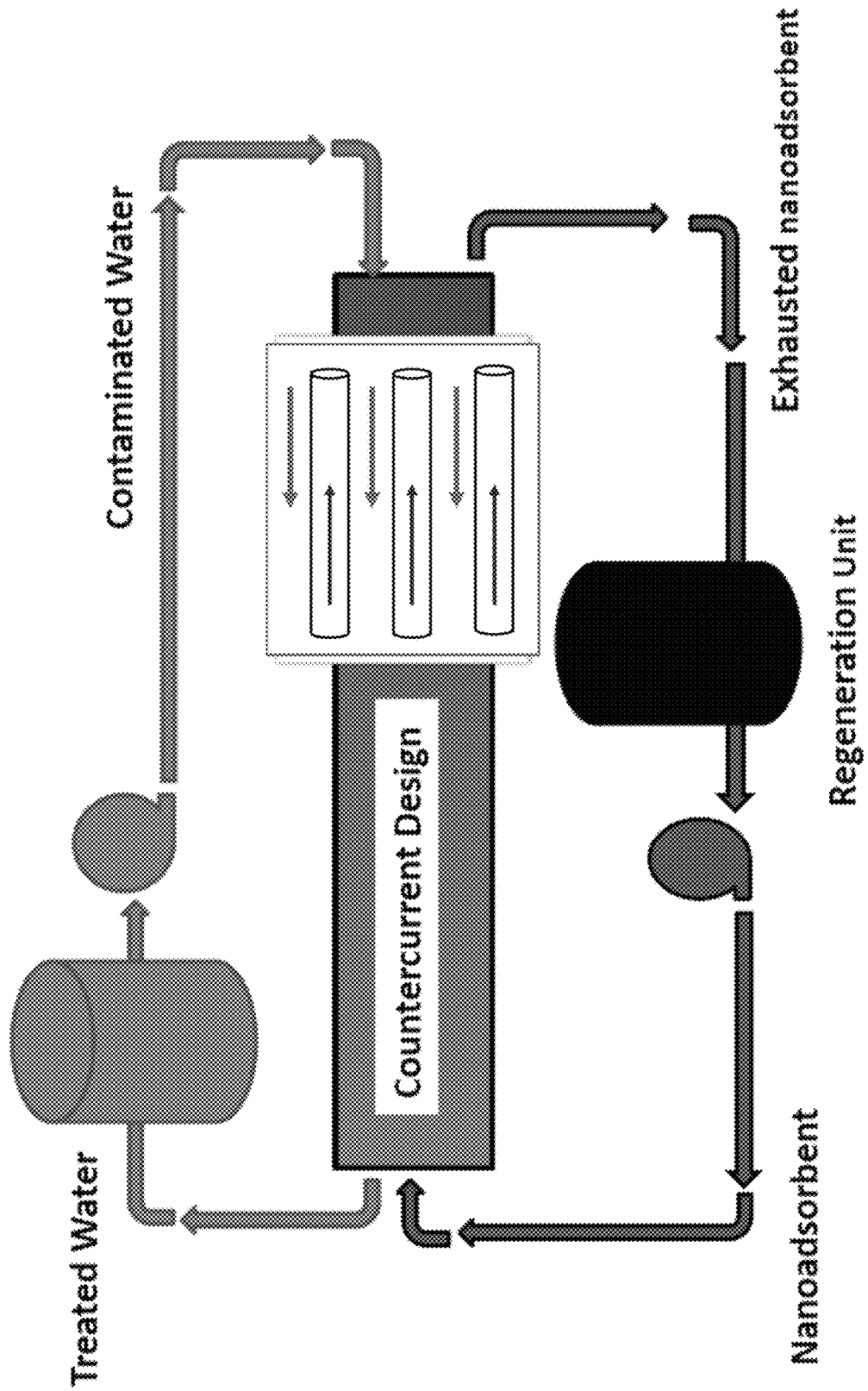
FIG. 4 depicts a process designed for an industrial-scale water treatment system.

Nanoadsorbents are delivered by bigger tubes. These bigger tubes carry tubular membranes in them. The tubular membranes deliver contaminated water to the system. The tubular membranes also allow contaminants to leave and enter another solution that carries nanoadsorbents. The tubular membranes block the nanoadsorbents from entering the water. Treated water leaves the system through the tubular membrane without any nanoadsorbent and with lower concentration of contaminants (FIG. 3A, FIG. 3B, and FIG. 4).

Figure 7:
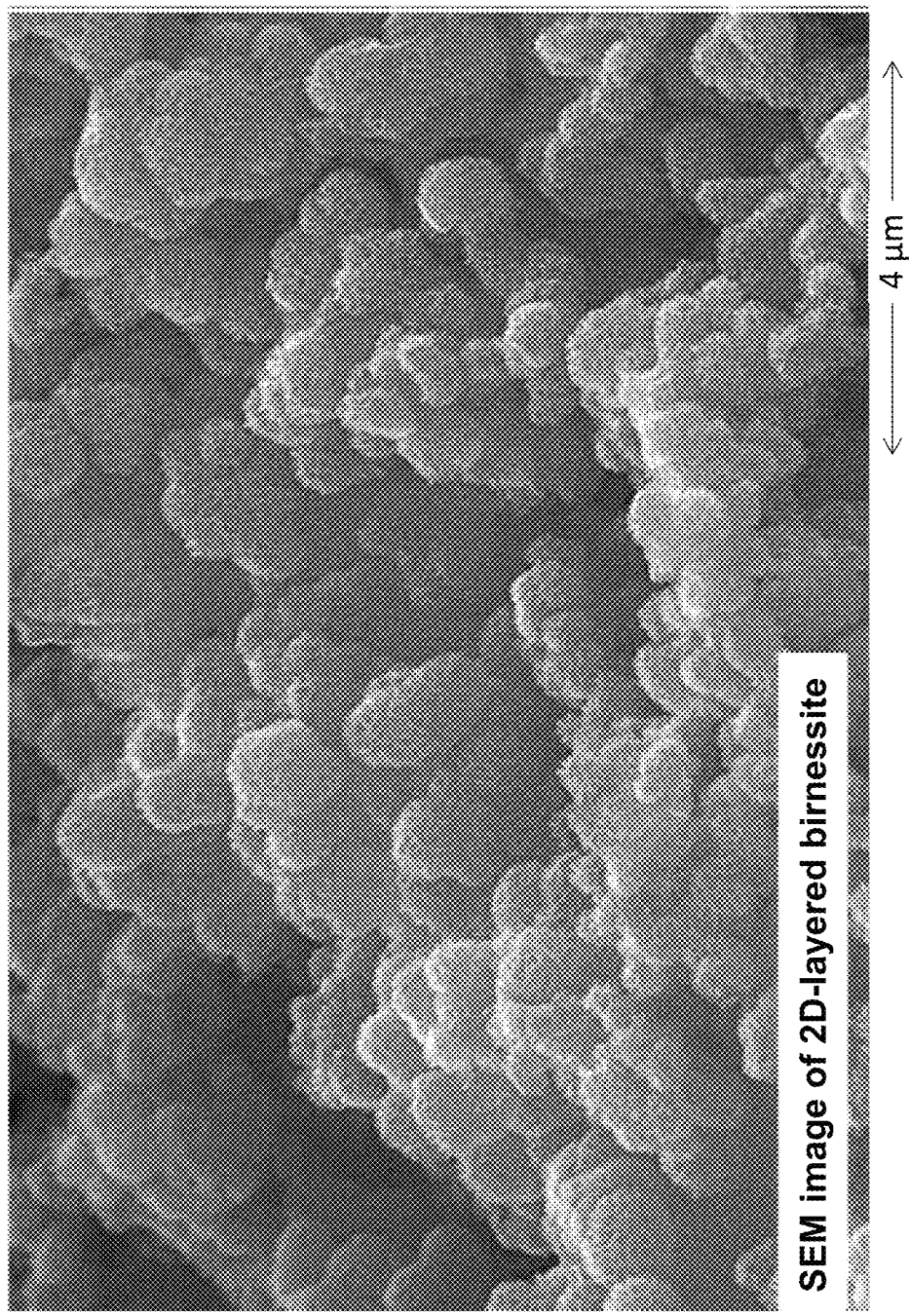
FIG. 7 depicts a scanning electron microscopy (SEM) image of 2-D layered birnessite.
Figure 8C:
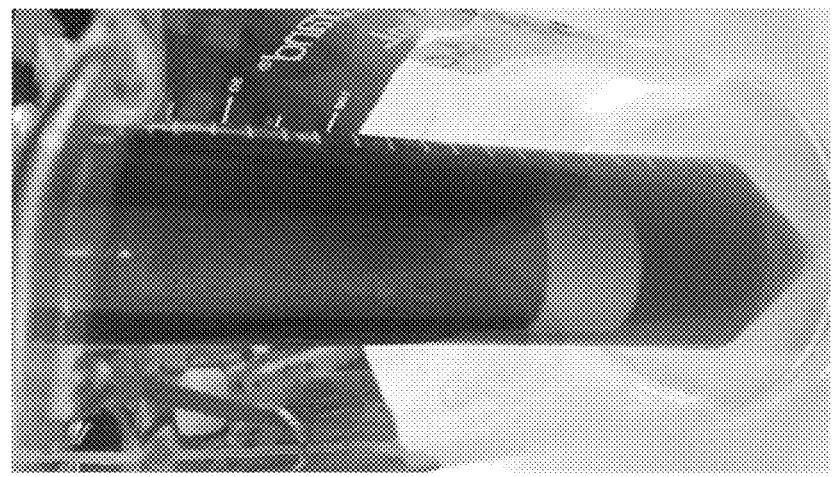
FIG. 8A, FIG. 8B, and FIG. 8C, depicts a small-scale purification membrane filter.
Figure 8B:
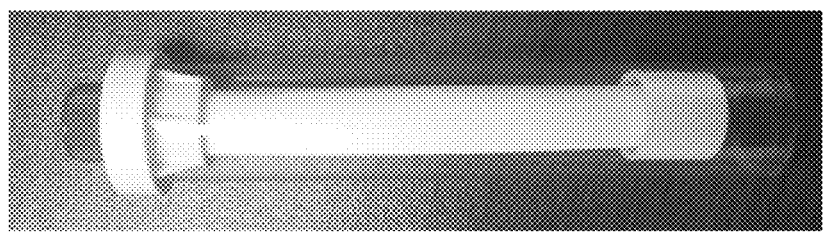
Figure 8A:
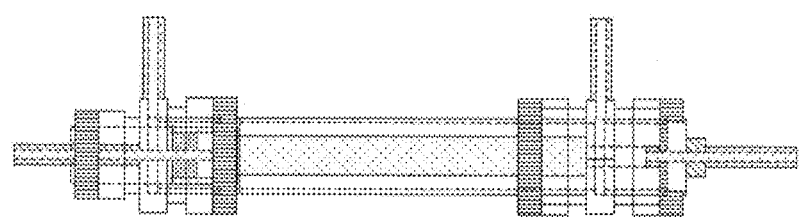
Figure 9B:
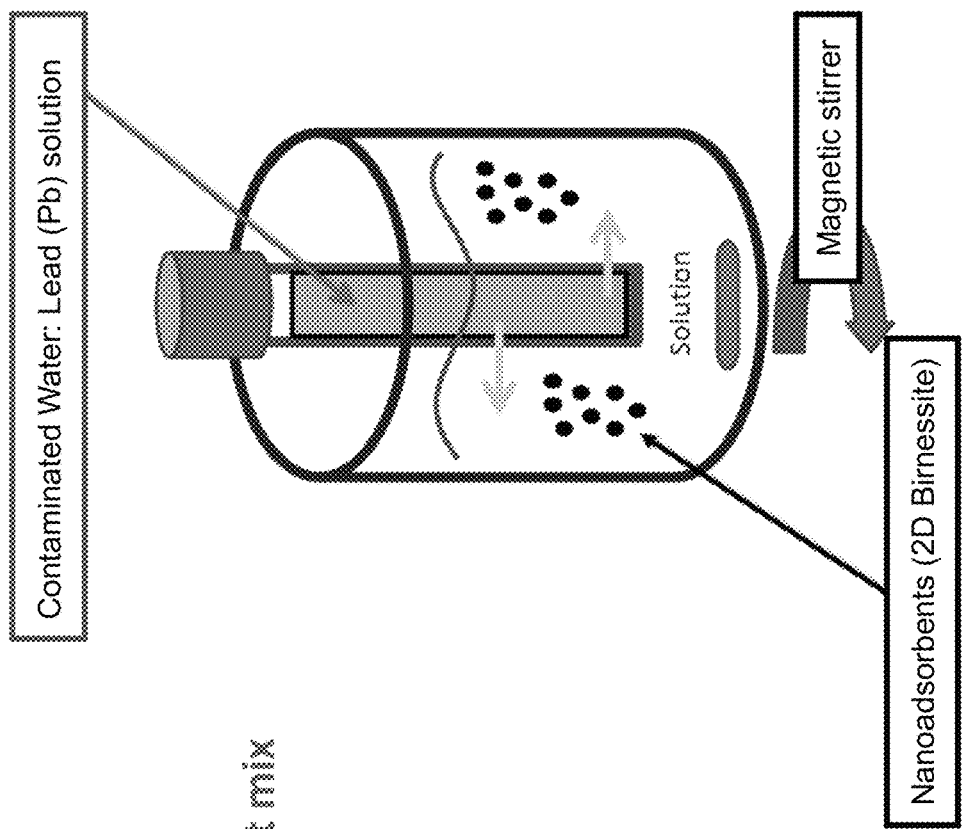
FIG. 9A and FIG. 9B, depicts a process of a purification method of contaminated water using a purification membrane filter.
Figure 9A:
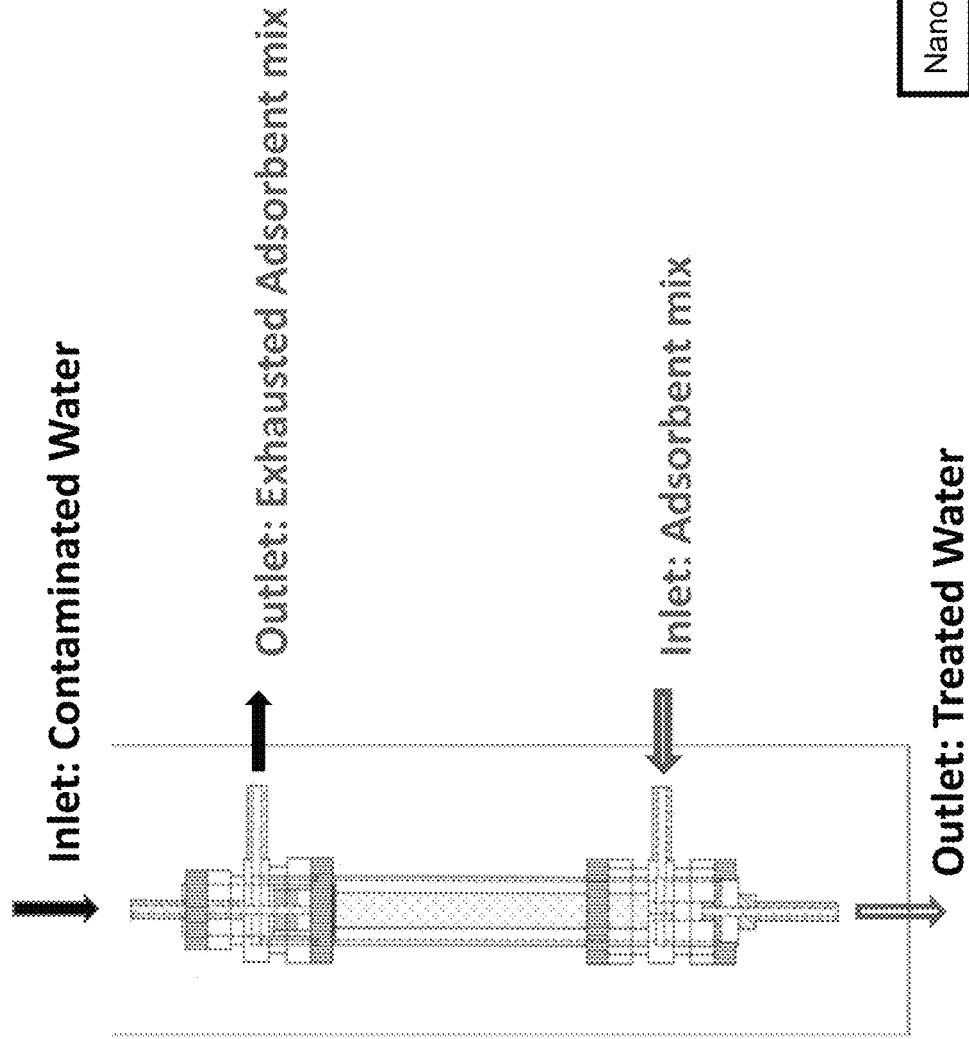

Birnessite (2D particles; FIG. 7), dispersed in water, was circulated around a tubular membrane to adsorb the contaminant (lead) that was being transferred from the inner solution to the outer solution using a tubular membrane (FIG. 8A, FIG. 8B, and FIG. 8C). The fluid was mixed to increase: 1) adsorption rate of lead by birnessite; 2) mass transfer of lead from inner solution to outer solution; 3) to homogeneously disperse the adsorbents and prevent sedimentation of the adsorbents (FIG. 9A and FIG. 9B). The result of these experiments demonstrated that the present invention provides at least three major advantages: 1) no pressure loss due to the use of nanomaterials (economic feasibility); 2) no health concerns due to the use of nanomaterials (nanomaterial and treated water never mix); 3) no separation unit was needed (economic feasibility).

Figure 10B:
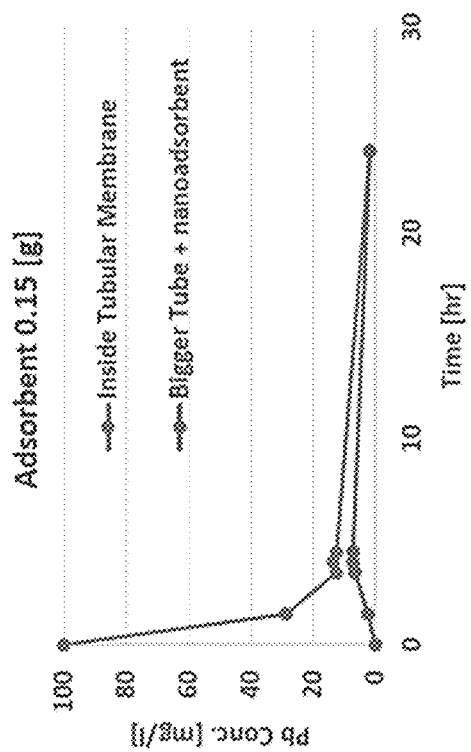
FIG. 10A and FIG. 10B, depicts a concentration of lead (Pb) in an inside and outside tubular membrane of the purification membrane filter.
Figure 10A:
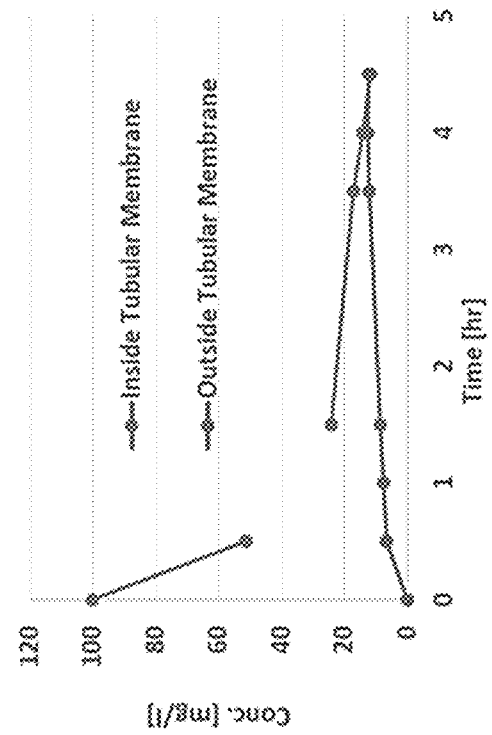

The tubular membranes were tested for delivery of lead. The inside tubular membrane was filled with aqueous solution with an initial lead concentration of 100 mg/L and was equilibrated during the course of 4 hrs of mixing. No adsorbent was added to the bigger tubes. Lead concentration in both the inner and the outer solution was close to the theoretical concentration of 12 mg/L. The experiment was stopped after the solution concentrations equilibrated (FIG. 10A).

The removal of lead using the tubular membrane filter was also tested. The inside tubular membrane was filled with aqueous solution with an initial lead concentration of 100 mg/L and the bigger tubes were filled with adsorbent mass of 0.15 g. After 24 hrs of mixing, the lead concentration reached 1.70 mg/L in both tubes (in the inside tubular membrane and in the bigger tube, which contained the nanoadsorbent) (FIG. 10B).

The examples described above demonstrate the utility of the nanomaterial tubular membrane filter prototype in the removal of lead (Pb) using 2D Manganese Oxide ($MnO_x$) nanomaterial. The demonstrated design used nanotechnology (or 2D materials) and membrane technology simultaneously to remove contaminants (or chemicals of interest) from a solution. Lead (Pb) and 2D Manganese Oxide were solely examples to prove the concept. This process has a vast potential to resolve the bottleneck of using nano- and 2D materials in water treatment and many refining processes.

Nanomaterials have been extensively explored in the past few decades as a new class of adsorbents for water treatment. However, many researchers have proposed the addition of a separation step for removal of used nanoadsorbent. This approach has made the use of nanoscale adsorbents infeasible. In addition, most nanoparticles tend to aggregate in aqueous solutions and this aggregation results in a drastic decrease in removal efficiency. To the best of our knowledge, no feasible and realistic use of nanoadsorbent in water treatment has been published to this date. This invention allows the industry and scientific community to overcome the most crucial bottleneck in employing 2D- and nanomaterials in treatment processes such as contaminant removal in water treatment.

In order to test industrial scale applications, a small pilot-scale setup was tested in two different configurations. Similarly, the small pilot-scale setup design also employed 2D materials and membrane technology simultaneously.

Figure 11:
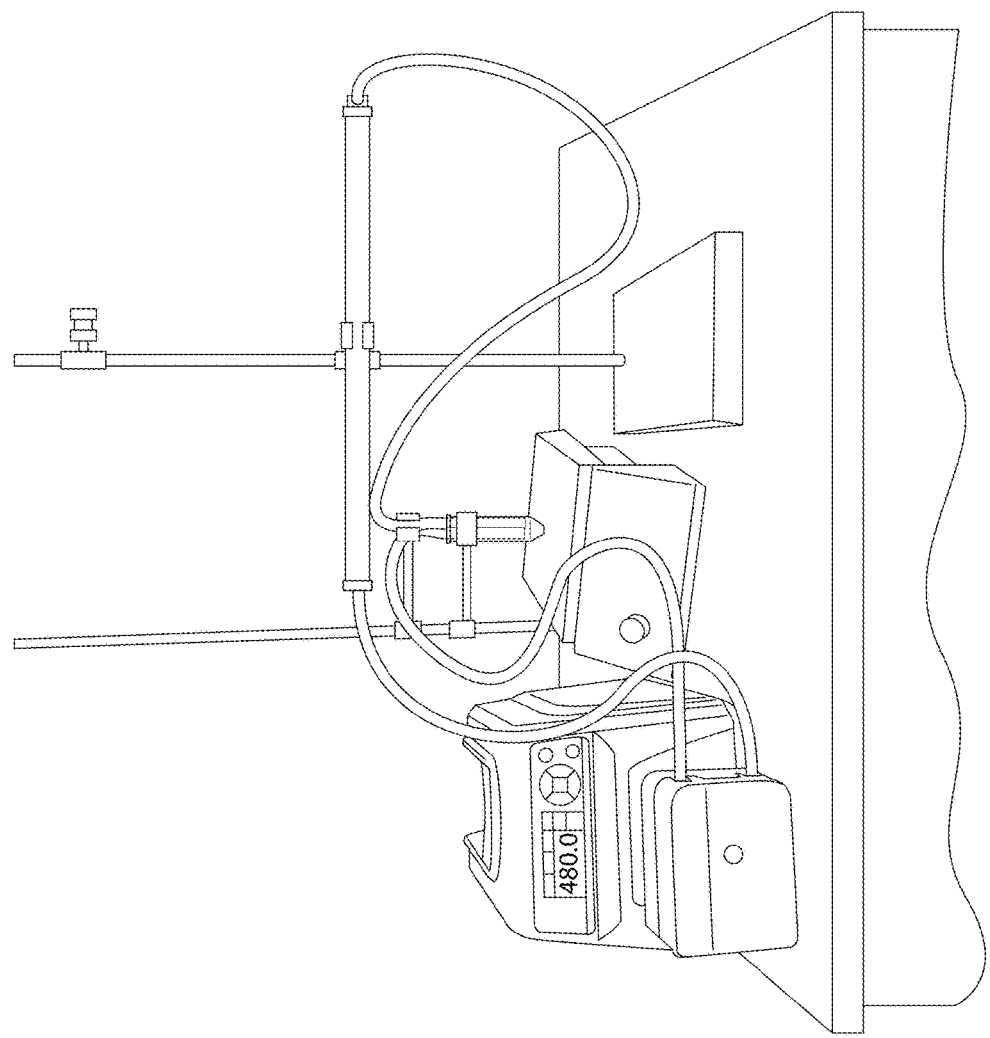
FIG. 11 depicts a small pilot-scale horizontal setup of a simultaneous use of 2D materials and membrane technologies.
Figure 12:
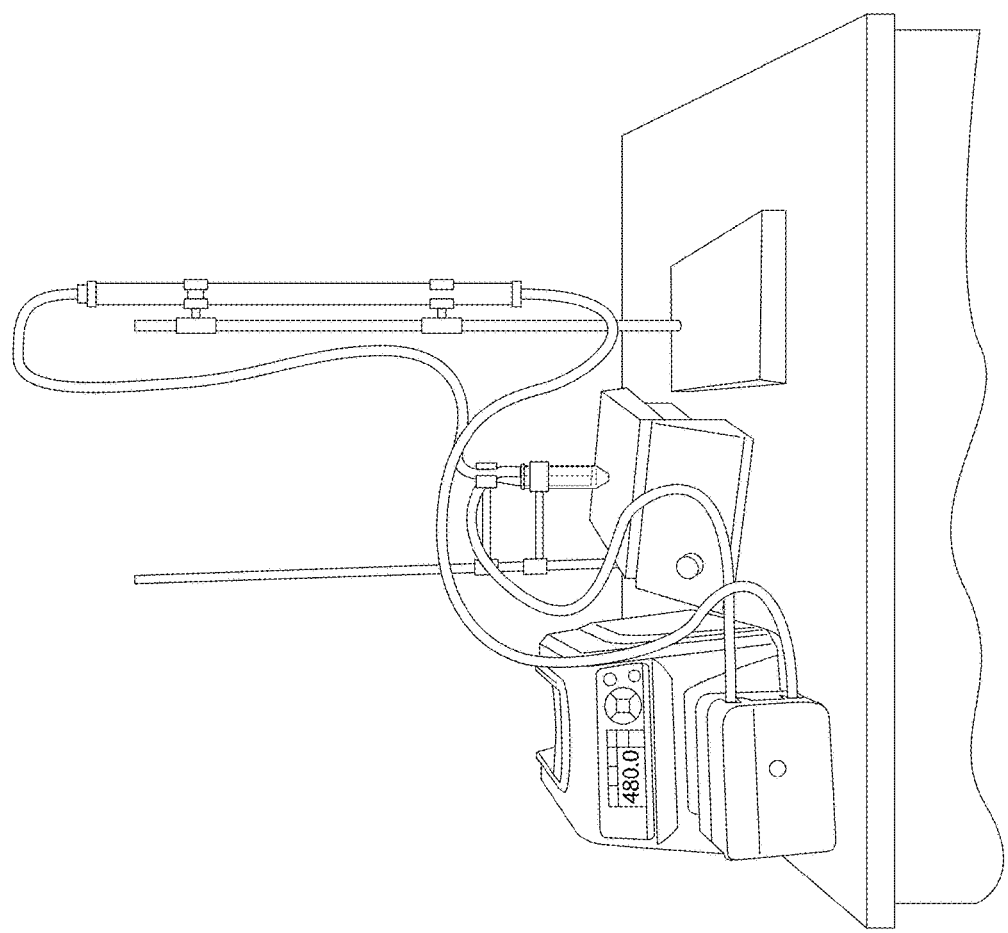
FIG. 12 depicts a small pilot-scale vertical setup of a simultaneous use of 2D materials and membrane technologies.
Figure 13A:
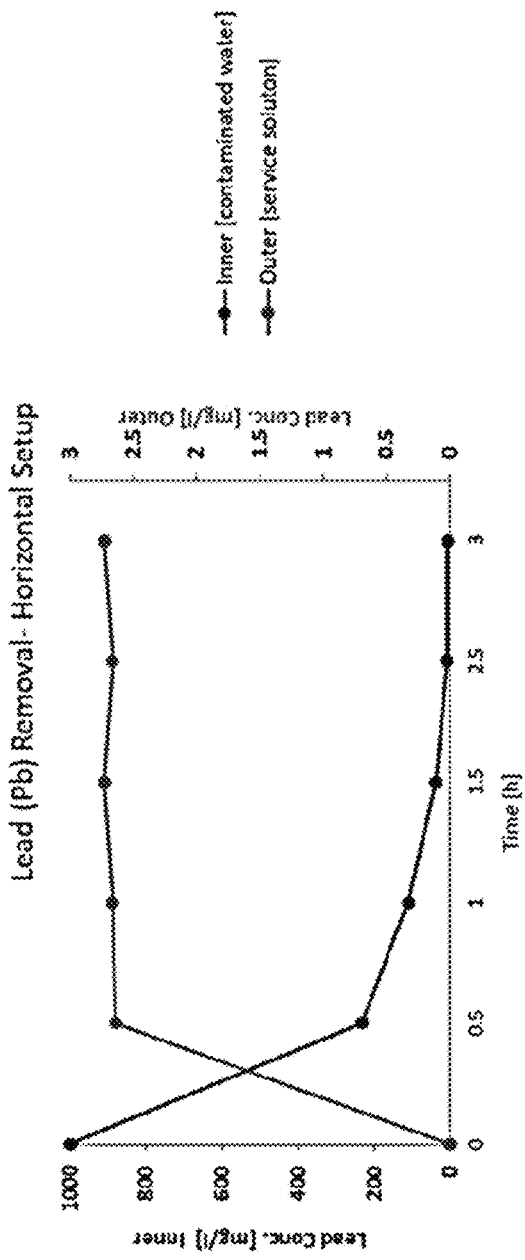
FIG. 13A and FIG. 13B, depicts a concentration of lead (Pb) in an inside and outside tubular membrane of the purification membrane filter.

In order to test the nanomaterial filter for both water treatment and dialysis industry, a new setup, as shown in FIG. 11 and FIG. 12, was assembled. In these experiments, contaminated water, which has an initial lead (Pb) concentration of 1000 mg/L, was purified using the nanomaterial tubular filters. The contaminated water was inside a tubular membrane (inner flow). A solution of deionized (DI) water and in-house synthesized 2D $MnO_x$ was running outside the tubular membrane (outer flow or service solution). The first setup, as shown in FIG. 11, was able to remove lead (Pb) by 99.6% after 3 hrs. The initial lead (Pb) concentration, 1000 mg/L, was reduced to 4.64 mg/L after 3 hours. Table 1 shows the removal efficiency of the system. The system was capable of removing lead (Pb) by 76.8% after 30 minutes and by 89.2% after 1 hour. FIG. 13A shows the removal of lead (Pb) by the system over the course of 3 hours.

TABLE 1

Lead (Pb) Removal Efficiency Using Horizontal Purification System Setup

| Time (h) | Removal (%) |
|---|---|
| 0.5 | 76.8 |
| 1 | 89.2 |
| 1.5 | 96.41 |
| 2.5 | 99.36 |
| 3 | 99.54 |

Figure 13B:
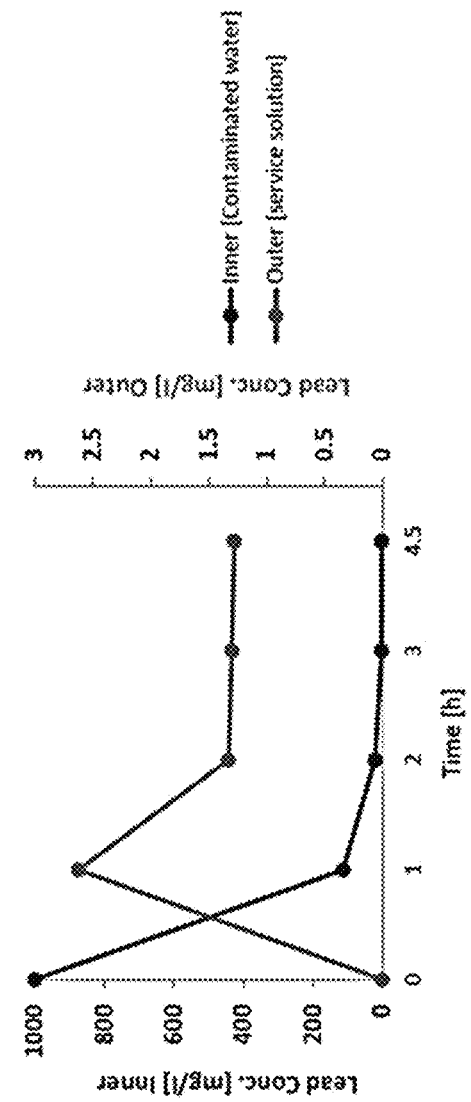

The 2nd setup, as shown in FIG. 10, was capable of removing lead (Pb) by 99.9% after 4.5 hrs. The initial lead (Pb) concentration, 1000 mg/L, was reduced to 1.28 mg/L after 4.5 hours. Table 2 shows the removal efficiency of the system. The system was capable of removing lead (Pb) by 88.8% after 1 hour and by 97.9% after 2 hours. FIG. 13B shows the removal of lead (Pb) by the purification system over the course of 4.5 hours.

TABLE 2

Lead (Pb) Removal Efficiency Using Vertical Purification System Setup

| Time (h) | Removal (%) |
|---|---|
| 1 | 88.8 |
| 2 | 97.97 |
| 3 | 99.817 |
| 4.5 | 99.9 |

This invention allows the water treatment industry to overcome the most crucial bottleneck in employing 2D nanomaterials in water treatment. In this design, almost all the technological constrains mentioned above were resolved using the novel filter and purification setup of the present invention. This invention has the potential to revolutionize the water treatment industry, specifically in the area of using 2D- and nanomaterials as the new class of adsorbent. This invention in part resolves the following challenges: economic feasibility, instability, release-and-separation, regeneration-and-reuse, and unclear fate and environmental toxicity by combing nanoscience with membrane technology.

Example 2: Nano-Assisted Dialysis for Ion Removal and Computational Modeling Presented herein is a simple method for metal sorption to resolve the bottleneck of using nanoadsorbents in conventional water treatment facilities. A tubular dialysis membrane was used as a barrier to separate hazardous synthetic water (dialysate) from the service solution (permeate) carrying nanoadsorbents. The synthetic water contained 1 [g/l] of lead inside the tubular membrane (dialysate), and the service fluid (permeate) contained 1.5 [g/l] of birnessite. FIG. 11 presents a simplified purification system. The concentration gradient generated between the lead solution (dialysate) and the service fluid (permeate) creates a driving force for lead ions to move from dialysate to permeate by diffusing through the membrane. Once the lead ions enter the permeate, they are adsorbed by birnessite. The addition of nanoadsorbents to permeate allows maintaining the highest concentration gradient between dialysate and permeate. The service fluid, permeate containing nanoadsorbents, was continuously pumped through the dialysis system to keep the nanoadsorbent floating in the system, in an attempt to create a homogenous distribution of adsorbents. Two sets of experiments were conducted using the tubular membrane setup vertically and horizontally to test if the gravity could impact the flow regime of the service fluid and consequently affect the removal efficiency.

Lead (Pb) toxicity has been well documented as it can cause a wide range of health effects and thus poses a serious threat to public health. Several structures of the manganese oxides have been used and studied for the removal of heavy metals (McCann, et al.; *Chemosphere*. 2015; 138:211-217; Beak, et al., Environ Sci Technol. 2008; 42(3):779-785; Cho, et al., J Porous Mater. 2011, 18, 125-131; Villalobos, et al., Environ Sci Technol. 2005; 39(2):569-576; Van Genuchten, et al., Environ Sci Process Impacts. 2016; 18(8):1030-1041; Liu, et al., Catal Sci Technol. 2018; 8(20):5344-5358). However, layered manganese oxide has attracted much attention because of its layered structure which can be occupied by heavy metals (Beak, et al., Environ Sci Technol. 2008; 42(3):779-785). To confirm the adsorption and removal of lead by hexagonal birnessite, the synthesized 2-dimensional (2D) layered $MnO_2$ was characterized before and after the adsorption process.

Chemicals: All chemicals were analytical grade and were used as received without further purification.

Instrumentation: X-ray diffraction (XRD) was performed using a Bruker d8 instrument. Scanning electron microscopy (SEM) images of birnessite were collected using a FEI Quanta 450FEG microscope. Transmission electron microscopy (TEM) images were recorded using a JEOL JEM-1400 microscope operating at 120 kV.

Synthesis of the Hexagonal Birnessite: K-Birnessite (hexagonal birnessite) was synthesized by McKenzie procedure. $KMnO_4$ solution (0.4M, 250 ml) was heated at 80° C. and hydrochloric acid (HCl, 4M, 50 ml) was added dropwise (1 ml/min) for 30 min after addition of acid. Then the solution was aged for 15 h at 50° C. and centrifuged and washed five times (McKenzie, *Mineral Mag.* 1971; 38(296):493-502).

Rapid Adsorption Studies: To calculate adsorption isotherms, a modified rapid adsorption experiment was used to reach equilibrium in a short time and to count for desorption of lead under vigorous mechanical stresses. 6 [ml] of lead solution was added to a 15 [ml] vessel and then birnessite was added. Vessels were put on an orbital shaker rotating at the speed of 200 [RPM] for 40 [min] and 48 [h]. Different masses of adsorbents or initial lead concentrations were added for each set of experiments.

Figure 14:
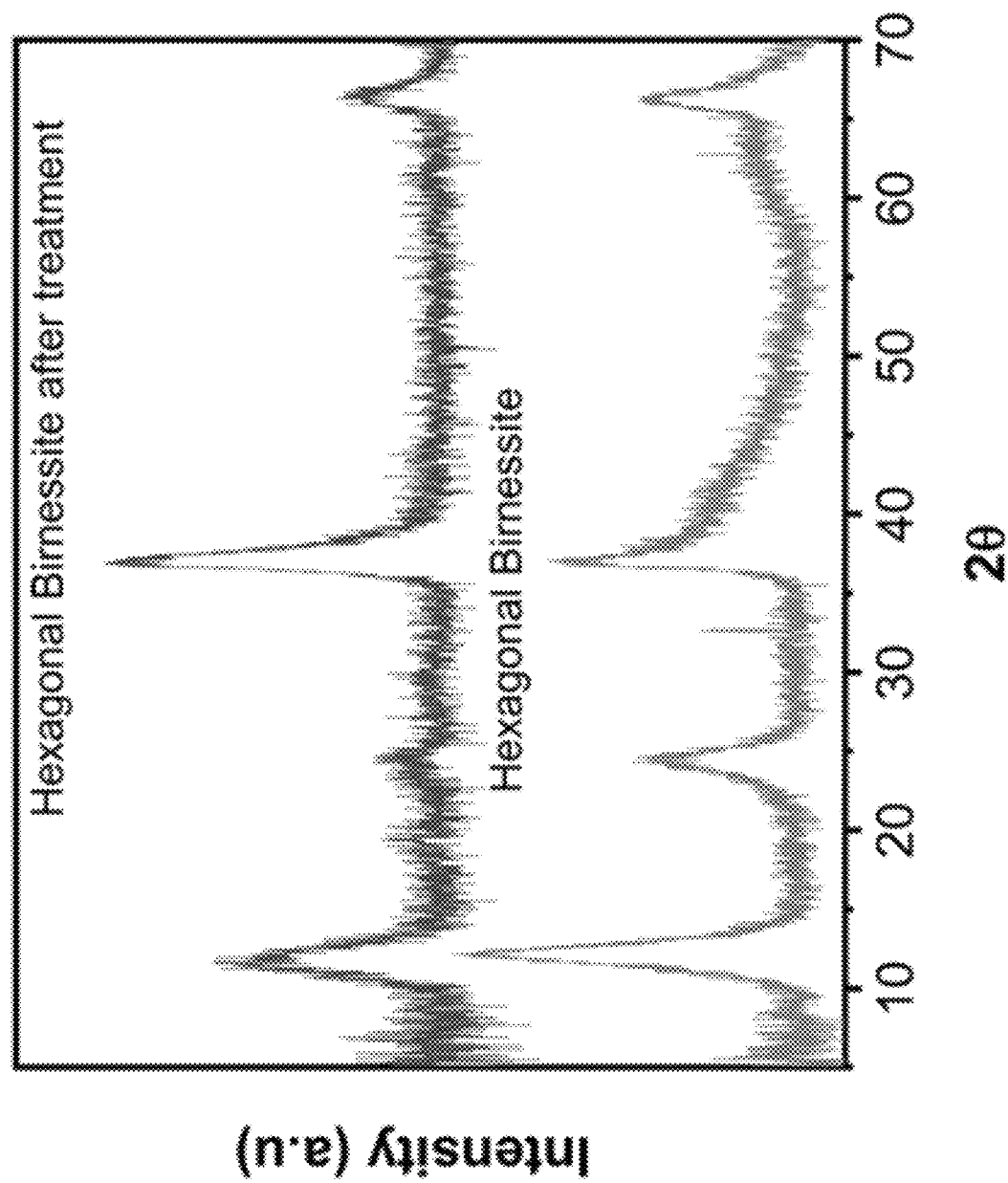
FIG. 14 is an XRD pattern of birnessite and Pb$^{2+}$/birnessite.
Figure 15:
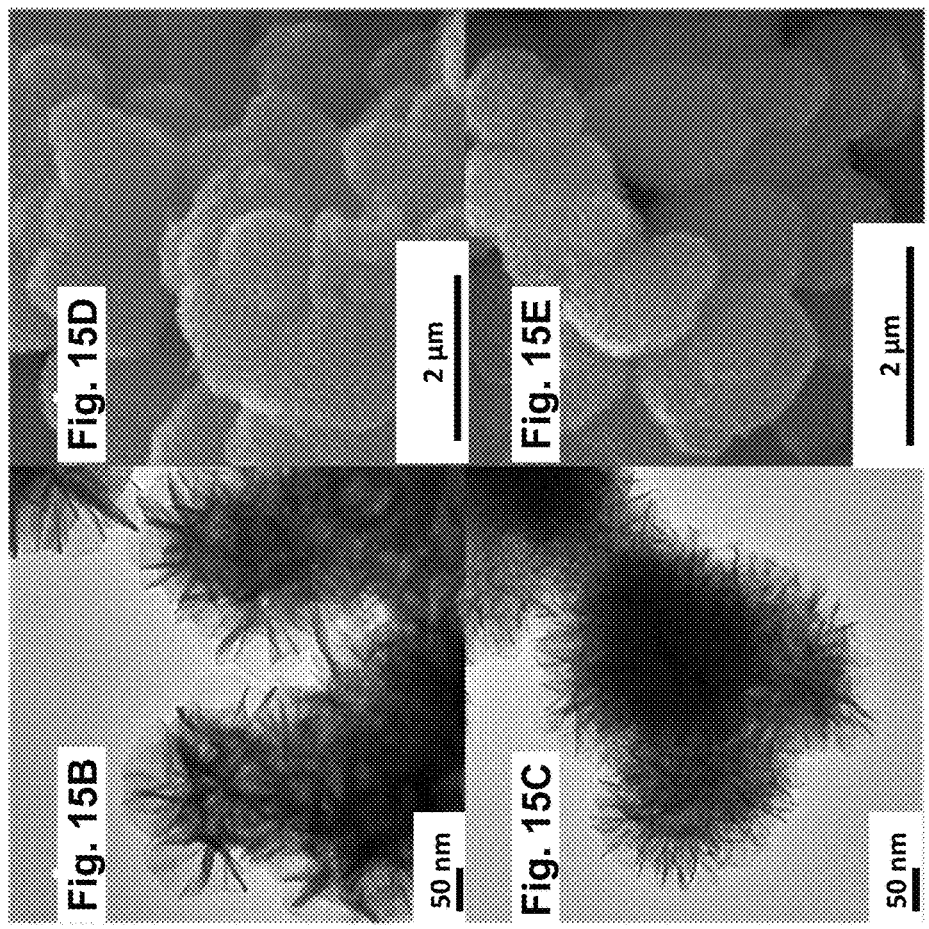
FIG. 15, comprising
Figure 16:
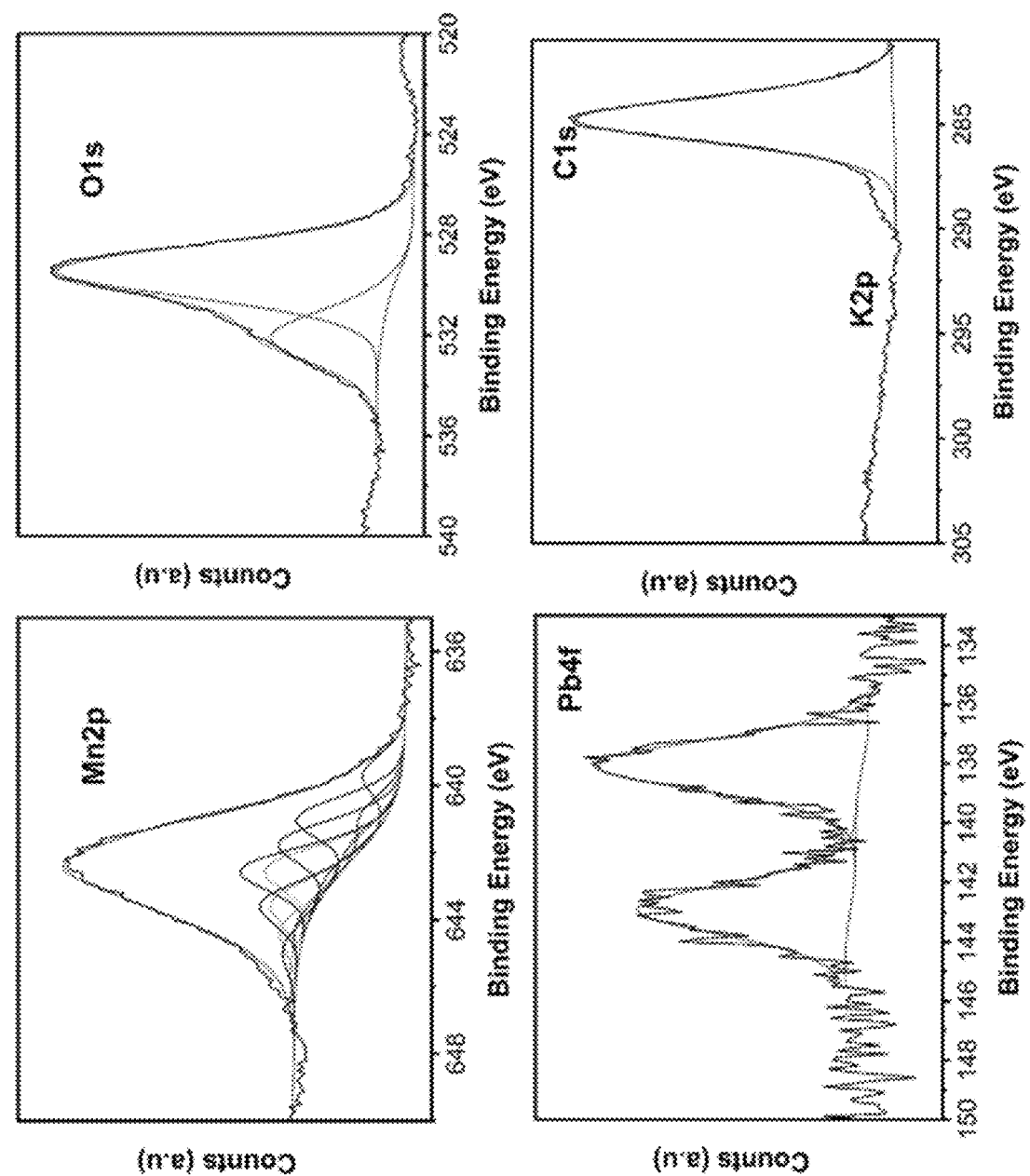
FIG. 16 depicts an XPS analysis of birnessite after Pb adsorption.

Material Characterization: Energy dispersive x-ray spectroscopy (EDS) analysis detected a Pb concentration of 0.6 atomic percentage after the adsorption process. The EDS mapping analysis showed a uniform detection of Pb adsorbed by birnessite particles. X-ray diffraction (XRD) pattern of hexagonal birnessite is presented in FIG. 14. The (001) brag reflection indicates that the interlayer spacing of birnessite is around 7.25 Å. After the adsorption, (001) reflection of the birnessite shifted toward a lower two theta value, and the interlayer distance of layers increased to 7.57 Å. The XRD pattern confirms lead ions intercalated and trapped to the interlayer of birnessite. It is imperative that there is a single layer of water and $K^+$ in the interlayer region of hexagonal birnessite. Flower-like microsphere nanostructure of hexagonal birnessite was observed before and after the adsorption studies, proof that the structure was reserved after Pb adsorption. FIGS. 15B, 15C, 15D, and 15E exhibit SEM and TEM images showing the morphology of birnessite before and after exposure to Pb. X-ray photoelectron spectroscopy (XPS) was used to verify the adsorption of $Pb^{2+}$ to the birnessite interlayer. The peak at 530 eV was attributed to lattice oxygen in $MnO_2$. Another peak appeared at the higher binding energy due to $H_2O$. It indicates there is water in interlayer space which is consistent with XRD results. After the adsorption process, two peaks appeared at 138 eV and 143 eV which can be attributed to Pb $4f_{7/2}$ and Pb $4f_{5/2}$, respectively. The XPS results suggest that the average oxidation state of the manganese changed, and this is consistent with prior studies (Ling, et al., Chem Geol. 2018; 479:216-227; Wang, et al., Chem Geol. 2012; 292-293:25-34). FIG. 16 exhibits an XPS analysis of birnessite after Pb adsorption.

Figure 17:
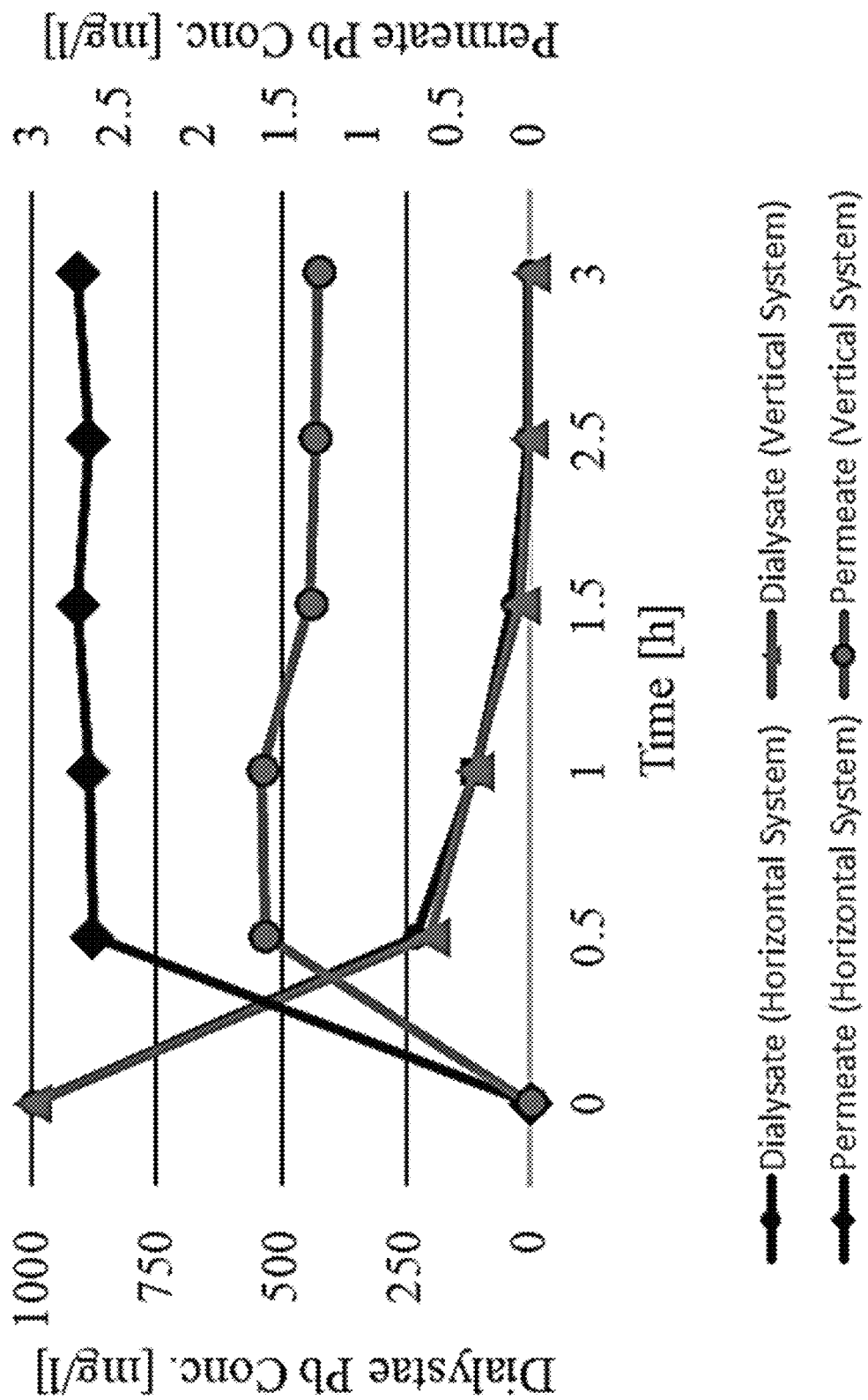
FIG. 17 is a chart showing lead (Pb) concentration in dialysate and permeate overt time of operation.

Nano-Assisted Dialysis: FIG. 17 presents the lead concentration in dialysate and permeate over time. The system was tested in vertical and horizontal arrangements. The initial dialysate concentration was 1 [g/l]. Substantial removal of lead was observed in dialysate for both arrangements after 0.5 [h], removal of 79.9% for the vertical, and 76.8% for the horizontal arrangement. Permeate lead concentration remained relatively the same for both arrangements throughout the experiment. However, the permeate concentration was lower for the vertical arrangement, about 0.001 [g/l] lower than the horizontal arrangement. After 1.5 [h] of operation, both arrangements removed more than % 95 of lead from the dialysate. For the vertical arrangement, the dialysate and permeate concentration reached 0.001 [g/l] after 3 [h]. As for its counterpart, the horizontal arrangement, the dialysate lead concentration reached 0.0046 [g/l], and 0.0027 [g/l] for the permeate after 3 [h].

Simulation: For a better demonstration of the proposed system, COMSOL Multiphysics® version 5.5 was used to simulate a theoretical scenario for the use of nanoadsorbents in a dialysis system. FIG. 18A presents the transport and adsorption of dissolved contaminants in the system. Arrows in FIG. 18B depict simulated contaminant flow across a dialysis membrane. The arrows are not scaled. This figure shows an axisymmetrical geometry for a vertical tubular membrane apparatus. The contaminants diffuse through a membrane due to a concentration gradient between the dialysate and permeate. Therefore, they move from the dialysate, high concentration domain, to permeate domain with much lower concentration. The dialysate and permeate laminarly flow in the opposite direction, a counterflow arrangement, around the tubular dialysis membrane. Without the addition of nanoadsorbents in permeate, the contaminants are transported by diffusion and convection in dialysate and permeate domains. The diffusion is the only mass transport mechanism in the membrane. The mass transport is modeled using the Transport of Dilute Species interface, and laminar flow is assumed to study the convective flux. The Langmuir model is considered for the surface reaction between the adsorbents and contaminants. The data presented herein represent the simultaneous calculation of the spatial variation of the dissolved contaminant concentration and adsorbent open-sites within permeate domain in a dialysis system.

The proposed model solves for spatial variation of contaminant concentration (non-adsorbed contaminant) and considers the adsorption of the contaminants on the adsorbent particles as a spatially continuous process described by a sink term, equation (1), in the permeate domain. This sink term is written as:

$$R = r \cdot A_p \cdot n_p \quad (1)$$

$$R \left[ \frac{mol}{m^3 \cdot s} \right]$$

represents the sink reaction due to adsorption, where $$r \left[ \frac{mol}{m^2 \cdot s} \right]$$

is surface reaction rate (Langmuir type), $$A_p \left[ \frac{m^2}{particle} \right]$$

is the surface area of a single adsorbent particle, and $$n_p \left[ \frac{m^2}{particles} \right]$$

is the number of adsorbent particles per unit volume. Therefore, the transport equation for the contaminant is written as shown in equation (2).

$$-D_1 \cdot \nabla C_i + u_1 \nabla C_i = R_i \quad (2)$$

Where $$c_i \left[ \frac{mol}{m^3} \right]$$

is contaminant molar concentration, $$D_1 \left[ \frac{m^2}{s} \right]$$

is a diffusion constant, $$R_i \left[ \frac{mol}{m^3 \cdot s} \right]$$

is the sink reaction due to adsorption, and $$u \left[ \frac{m}{s} \right]$$

is the velocity. The transport equation for adsorbents open-sites is written as equation (3). Where $$D_2 \left[ \frac{m^2}{s} \right]$$

is a diffusion coefficient of open-site adsorbents and $$S_i \left[ \frac{mol}{m^3} \right]$$

is the molar concentration of open-site adsorbents.

$$-D_2 \cdot \nabla C_i + u_2 \nabla C_i = R_i + S_i \quad (3)$$

Figures 19A, 19B:
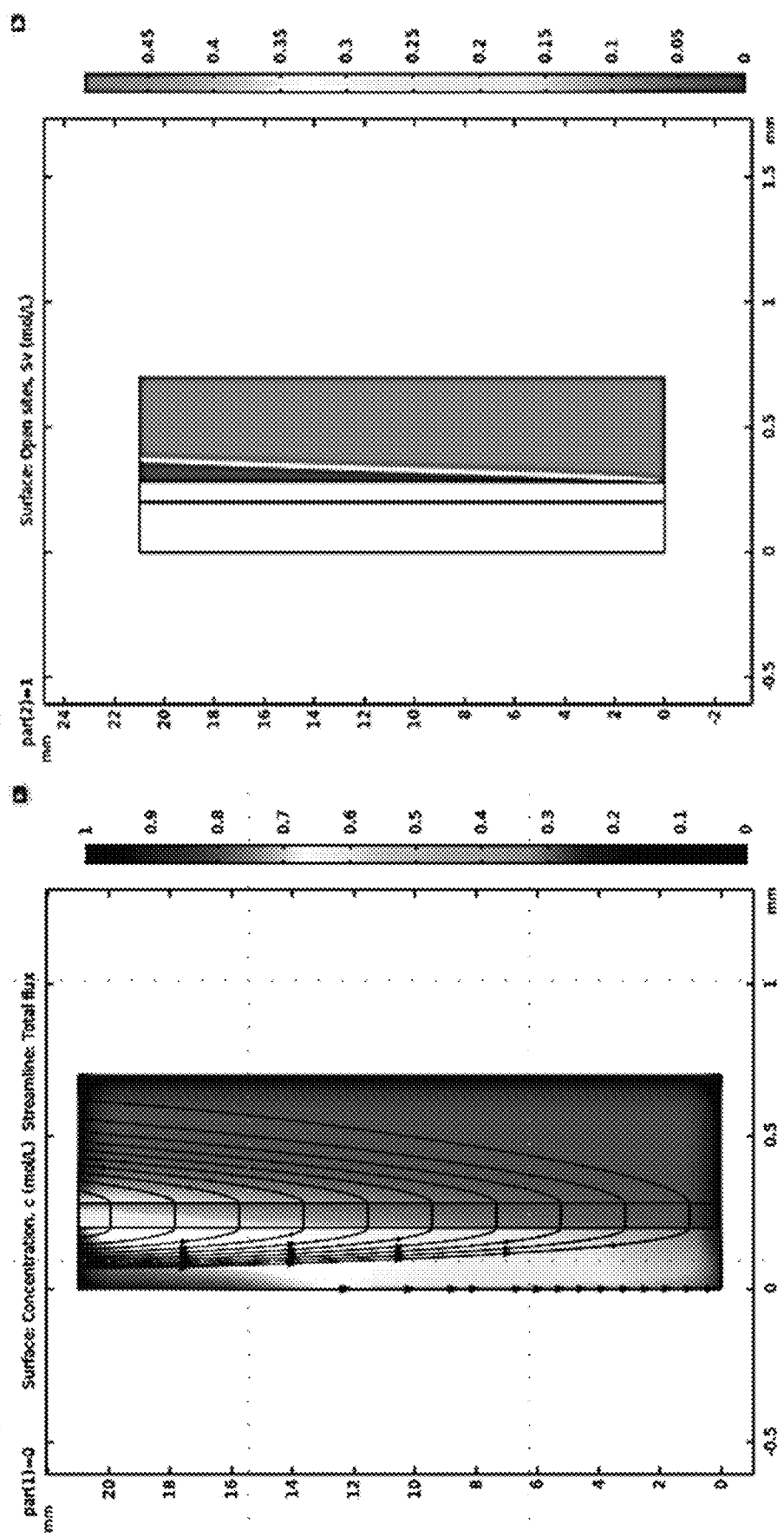
FIGS. 19A and 19B, shows results from computational simulations.

FIG. 19A shows the distribution of the contaminant in dialysate, membrane, and permeate domains where the red color represents the highest contaminant concentration, and the shades of blue signify the lowest contaminant concentrations. The arrows show the theoretical flow path of contaminants. The concentration of adsorbents open-sites in the permeate domain is shown in FIG. 19B. Adsorbents are solely dispersed in the permeate domain and react with the contaminants that have diffused through the membrane and entered the permeate. As the adsorbents travel through the permeate, they lose their open-sites to contaminants due to adsorption. The red region presents the highest concentration of open-sites for adsorption, and the blue region represents an area where adsorbents are fully exploited.

Figure 20:
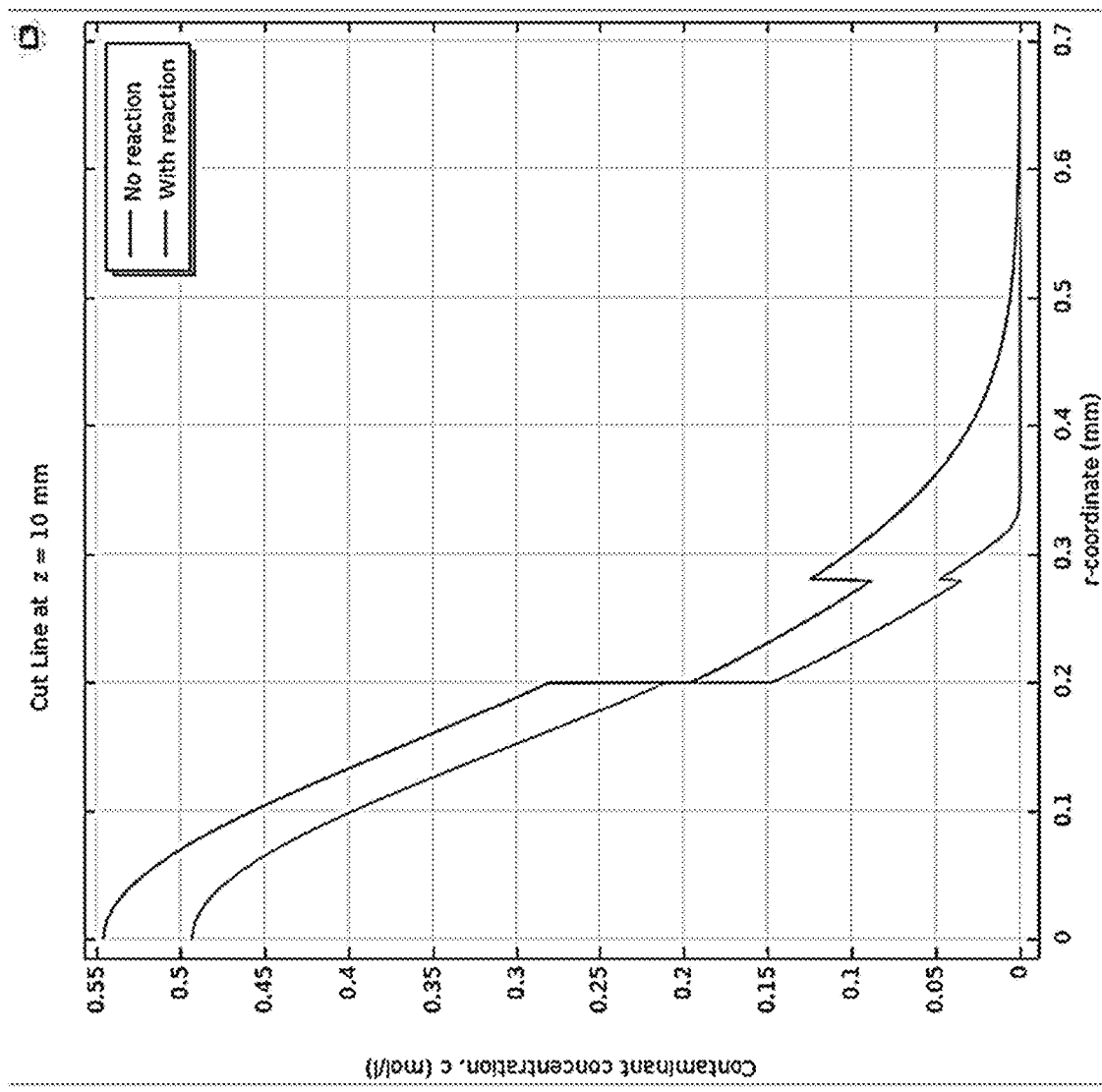
FIG. 20 is a plot of stationary contaminant concentration profile over the radius (r), the blue line, which starts at 0.55 mol/l presents the concentration in a conventional dialysis setup (no adsorbents), and the green line, which starts at 0.5 mol/l presents the contaminant concentration profile with adsorption.

The distribution of contaminant concentration is shown over the radius of a tubular system in FIG. 20 in an axisymmetrical geometry. The symmetry applies at r=0. The blue graph displays concentration profile in dialysate, membrane, and permeate domains without the addition of adsorbents. The green graph demonstrates the concentration profile for similar domains with the addition of adsorbents. These two graphs clearly show that the addition of adsorption has decreased the contaminant concentration noticeably at 10 [mm] downstream of the dialysate inlet.

The experimental results have shown that the addition of nanoadsorbents, birnessite ($MnO_2$), in permeate has significantly facilitated the removal of a contaminant (lead). The contaminant removal was achieved while keeping the nanoadsorbents and the dialysate phase separated. This method mitigates the problem of high-pressure loss in conventional adsorption columns for nano-sized adsorbents, avoids aggregation and agglomeration of nanomaterials in aqueous solutions by continuous mixing, and retains the nanoadsorbents in a closed system. The adsorption of contaminants in the permeate domain allows the system to maintain a high concentration gradient between the dialysate and permeate. Both vertical and horizontal arrangements performed well; however, the vertical arrangement is preferable. The use of tubular hollow fiber membranes instead of a single-layered dialysis membrane, used in this study, could considerably improve the removal efficiency for lower concentrations.

A theoretical scenario was simulated using COMSOL Multiphysics® to solve for the mass transport of contaminant in dialysate, membrane, and permeate domains. The simulated flow paths of contaminants show the mass transfer due to convection and diffusion. The addition of nanoadsorbents creates a sink for contaminant concentration in the permeate domain. The surface adsorption reaction exploits the free-sites of nanoadsorbents as they travel through the permeate and react with contaminants. More notably, the radial contaminant concentration profile shows the addition of adsorption term considerably decreases the contaminant concentration once compared to a conventional dialysis setup.

A simplified technique using dialysis and nanoadsorption simultaneously has been demonstrated for the removal of a toxic metal form water. Layered $MnO_2$ was used to remove a high concentration of lead. The analytical results confirm the removal of more than 75% of the initial lead concentration for both arrangements after 0.5 [h]. XRD and EDX analyses of used birnessite confirm the sorption of lead. The XRD results indicate lead adsorbs into the interlayer space of birnessite. Based on the simplified design used in the experiments, vertical design is preferable because nanoadsorbents tend to settle within the horizontal arrangement. The proposed method can be used for selective removal of ions in any purification systems. The dialysis processes used in medical, pharmaceutical, and chemical manufacturing industries can benefit from the use of the proposed methods.

Example 3: Removal of Arsenic with Ferrihydrite

The concept of a hemodialyzer, which is used in medicine as a biomimetic for artificial kidneys, suggests an alternative method for the application of nanomaterials in water treatment. During hemodialysis, blood is pumped into the hemodialyzer through an inlet and is distributed into a membrane. Pressure and a concentration gradient induce mass transfer through the membrane, and waste products and excess fluid are removed as blood flows to the outlet. Simultaneously, a dialysate solution is pumped in a counterflow direction outside the membrane and carries away the waste (Ding, W. et al. *Artif Organs* 39, E79-E89 (2015); Ding, W. et al. Int. J. Heat Mass Transf 47, 4849-4855 (2004)). A similar process can be adapted for the use of nanomaterials in water treatment, and fluid purification in general. As a contaminated stream is passed on one side a selective membrane, a counterflowing service fluid of nanoadsorbents is passed on the other side. As contaminants pass through the membrane, they can be picked up by fast-acting nanoadsorbents. This concept can also be applied more simply by passing a service fluid with unidirectional flow over a membrane containing a static contaminant solution.

A simplified application is demonstrated as a proof-of-concept for water treatment by utilizing a system to adsorb arsenite ($H_3AsO_3$ at or near a circumneutral pH) with two-line ferrihydrite (Fh). Arsenic is a naturally occurring metalloid that is both abundant and ubiquitous in the Earth's crust and is released in large quantities through industrial processes and agricultural applications. In the environment, arsenic combines with other elements and is found in several organic and inorganic forms (Bhattacharya, P. et al. Science of the Total Environment 379, 109-120 (2007)), but arsenite is most mobile and toxic (Jain and Ali, Water Res. 34, 4304-4312 (2000); Fernando, Critical Reviews in Environmental Control 21, 1-39 (1991)). Adsorption of arsenic onto iron oxide minerals has been investigated over the years (Bowell, Applied Geochemistry 9, (1994); Dixit & Hering, Environ. Sci. Technol. 37, 4182-4189 (2003); Gimenez, et al., J. Hazard. Mater. 141, 575-580 (2007); Aredes, et al., J. Clean. Prod. 60, 71-76 (2013)), and Fh, a naturally occurring nanomaterial and precursor to more crystalline iron oxides (Schwertmann, et al., Journal of Colloid and Interface Science, 209, 1, 215-223, (1999); Das, S., Hendry, M. J. & Essilfie-Dughan, J. Environ. Sci. Technol. 2011, 45, 1, 268-275), has gained substantial interest. Fh is an intrinsically nano-dimensioned material (2-3 nm diameter) with a BET surface area between 133-320 m2/g, a high adsorption capacity (Raven, et al., Environ. Sci. Technol. 32, 344-349 (1998); Schwertmann, & Cornell. Iron Oxides in the Laboratory. (Wiley-VCH Verlag, 2001); Li, et al., Dalt. Trans. 40, 2062-2066 (2011); Zhu, et al., J. Hazard. Mater. 189, 564-571 (2011); Kim, et al. Environ. Technol. (United Kingdom) 35, 251-261 (2014)), and strong binding to arsenic via inner-sphere 2C and 2E complexes (Ona-Nguema, et al., Environ. Sci. Technol. 39, 9147-9155 (2005)), that make it a desirable nanoadsorbent.

Presented herein are the removal efficiencies of Fh and changes in environmental variables Eh and pH. The obtained results were compared to those of traditional batch experiments (i.e., not utilizing membrane separation).

Materials and Methods

Synthesis and characterization methods of ferrihydrite: Fh was synthesized using the solvent deficient method reported by Smith, et al. (Inorg. Chem. 51, 6421-6424 (2012)). Briefly, a 1:3 molar ratio of $Fe(NO_3)$ $9H_2O$ (ACS grade, Acros) and $NH_4NO_3$ (98%, Acros) was continuously ground together using a mortar and pestle until bubbling stopped and a dark brown precipitate formed. The precipitate was dried at 100° C. for 24 hours, vacuum filtered and rinsed with small volumes of reagent grade water and dried again for another 24 hours. The material was ground to a fine dark brown powder in a mortar and pestle before analysis and use in experiments. All experiments were performed using the same single batch of Fh.

X-ray diffractograms for Fh were obtained by a Bruker $D_8$ Advance diffractometer operating at 40 kV and 40 mA using Cu-Kα radiation (λ=1.5406). The powder samples were scanned from 200 to 800 2θ in 0.02° increments with a is dwell time. The FTIR absorbance spectrum was obtained using a Perkin Elmer ATR-FTIR 100 spectrometer from 4000 to 650 $cm^{-1}$. Transmission electron microscopy (TEM) micrographs were taken using a JEOL JEM-1400 microscope. Scanning electron microscopy (SEM) micrographs were taken using a FEI Quanta 450 FEG microscope operating at 30 kV. The surface area of Fh was obtained using a Micrometrics ASAP 2020 analyzer with degassing at 100° C. for 4 hours and calculated using the Brunauer-Emmett-Teller (BET) method.

System Experiments: The dialysis system was prepared according to FIG. 21. A 100 kilodalton dialysis membrane setup was clamped vertically to a ring stand and a beaker was placed atop a stirrer with a stir bar. One end of a size 15 C-flex tubing was passed through a Cole-Parmer Masterflex L/S peristaltic pump fitted with a compatible high-performance pump head and was fixed to the bottom inlet of the dialysis system. The other end of the tube was placed inside the 600-mL beaker. The second piece of tubing was fixed to the top outlet of the system and its free end was placed inside the same beaker. Oxidation-reduction potential and pH probes were fixed from the ring stand inside the beaker to track changes in Eh and pH over time.

In preparation for use, the dialysis membrane was primed to remove the glycerin from the membrane. A 10% ethanol solution was used to both hand-fill the lumen of the membrane and to pump solution continuously through the outer body for 15 minutes. The apparatus was then rinsed several times with deionized water to remove traces of ethanol.

To start each experiment, 37 mL of pH 9.05 arsenite solution—prepared from $As_2O_3$ powder—was added by hand into the lumen of the membrane. A sample from the excess of this solution was preserved with concentrated nitric acid and analyzed to determine the initial arsenic concertation. Then, a 250 mL service solution containing a $NaNO_3$ ionic strength of 0.25 and a pH of 9.05 was prepared in the 600 mL beaker. An initial 5 mL sample was taken, and Fh was added into the beaker to attain 1.22 or 2.61 g/L loadings (by total system volume). The service solution was continuously stirred, slowly pumped from bottom to top to fill the system, and then set at a flow rate of 300 mL/min. Over the course of three hours, samples were taken from the beaker, filtered through a 0.45 μm PTFE syringe filter, acidified with concentrated nitric acid to a pH below 2, and refrigerated for preservation. Changes in the pH and Eh of the service fluid were also tracked over the run-time of each experiment. At the end of the experiment, a second sample was taken from the lumen of the membrane to determine the final arsenite concentration after treatment. Arsenite concentration in samples was analyzed using a Thermo Scientific iCAP Q ICP-MS operated by Alpha Analytical, Inc. following EPA Method 200.8 for total arsenic analysis. Solutions in the membrane lumen had initial arsenite concentrations of 545.5 and 679.5 mg/L for the 1.22 and 2.61 g/L ferrihydrite loadings, respectively.

Batch Experiments: Arsenite adsorption by Fh was evaluated with 1.25 and 2.68 g/L Fh loadings in two separate experiments. In each case, four 280 mL arsenite solutions—prepared from $As_2O_3$ powder—were adjusted to an ionic strength of 0.22 using $NaNO_3$ and set to an initial pH of 9.05 using NaOH and $HNO_3$. An initial 5 mL sample was taken from each solution, quickly filtered through a 0.45 μm PTFE syringe filter, acidified with concentrated nitric acid to a pH below 2, and refrigerated for preservation. Fh was introduced into three of the solutions while the fourth remained as a control. The solutions were continuously stirred atop a multi-stirrer at 600 RPM. Over the course of three hours, the solutions were sampled every half hour and samples were processed as described above. In between sampling periods, the solutions were covered to prevent evaporation. Changes in the pH and Eh of one of the non-control solutions was also tracked over the run-time of each experiment using pH and redox probes. Solutions with the 1.25 g/L adsorbent loading had initial arsenic concentrations of 74.4 and 111.6 mg/L and the control system had an initial arsenic concentration of 65.6 mg/L. Solutions with the 2.68 g/L adsorbent loading had initial arsenic concentrations of 88.4, 91.5, and 96.1 mg/L and the control system initial arsenite concentration was 92.7 mg/L.

The Results of the Experiments Will Now be Discussed

Ferrihydrite Surface Area Measurements: Surface area measurements performed on various batches of ferrihydrite synthesized by the SDM method yielded different values. Though batch-to-batch variation may be suspected, Table 3 shows that variance in the measurements was directly proportional to the difference in time between synthesis and BET analysis and the percentage of mass lost from degassing. Variance in the measurements was inversely proportional to the absorbance of the prominent FTIR carbonate peak at 1320 $cm^{-1}$. This data suggests that ferrihydrite adsorbs carbon dioxide over time, and the adsorption of carbon dioxide onto metal oxide materials followed by conversion to carbonate is well supported by the literature (Hausner, et al., J. Colloid Interface Sci. 337, 492-500 (2009); Hakim, et al. Ind. Eng. Chem. Res. 55, 7888-7897 (2016); Baltrusaitis, et al., Chem. Eng. J. 170, 471-481 (2011); Baltrusaitis, et al., J. Phys. Chem. C 111, 14870-14880 (2007); Miller, et al., Surf. Interface Anal. 33, 299-305 (2002); van Geen, et al., Geochim. Cosmochim. Acta 58, 2073-2086 (1994)). Adsorption of carbon dioxide onto ferrihydrite may decrease surface area results, making it difficult to compare reported values across the literature. Furthermore, there does not appear to be a standardization on the BET analysis conditions of ferrihydrite within the literature. Table 4 shows that authors have used varying degassing conditions with different combinations of drying temperature and drying time, which have been reported to impact the surface area value. In extreme cases, reported values can be erroneous, and caution is warranted in interpreting reported values (Weidler, Journal of Porous Materials volume 4, 165-169 (1997); Clausen, & Fabricius J. Colloid Interface Sci. 227, 7-15 (2000)).

TABLE 3

| BET - Syn Days | BET SA, m2/g | FTIR Abs 1320 $cm^{-1}$ | % Mass Loss from Degassing |
|---|---|---|---|
| 26 | 192 | 0.069 | 7.4 |
| 21 | 251 | 0.039 | 7.3 |
| 28 | 219 | 0.052 | 11.1 |
| 58 | 329 | 0.02 | 16 |

TABLE 4

| Degass Temp, C. | Degass Time, hr | Reference | Reported BET $m^2$/g |
|---|---|---|---|
| 80 | — | Zhu et al 2015 | 331 |
| 200 | 22 | Smith et al 2012 | 248 |
| 105 | 24 | Villacis-Garcia 2015 | 311 |
| 80 | 24 | Das et al 2011 | 347 |
| 110 | 2 | Raven et al 1998 | 202 |
| 200 | 6 | Hakim et al 2016 | — |
| 22 | 19 | Clausen & Fabricus 2000 | 215 |
| 22 | 19 | Clausen & Fabricus 2000 | 229 |
| 150 | 2 | Clausen & Fabricus 2000 | 301 |
| 150 | 2 | Clausen & Fabricus 2000 | 287 |

Ferrihydrite induced drop in pH: In preliminary trials, ferrihydrite at a loading of 1.25 g/L was added to solutions with an ionic strength of 0.22 M. In the absence of arsenic, the pH showed a sharp and fast decline in pH that plateaued within 5 minutes (FIG. 22). The change in pH is likely the complexation of hydroxyl groups to the metal iron centers of the material, leaving an excess of protons in solution that is presented as a decrease in the solution pH.

Arsenite-Ferrihydrite Batch Adsorption Profile: Data collected from the literature to determine how adsorption of arsenite by ferrihydrite could be impacted near environmental pHs. The data was taken from the referenced works and converted to the units listed below. The work of Kim et al 2014 (Environ. Technol. (United Kingdom) 35, 251-261 (2014)) and this work mainly show that as the excess arsenite concentration—the arsenite not adsorbed by ferrihydrite in a batch experiment—increases, the adsorption capacity increases and the removal efficiency decreases. In solutions were all the arsenite is adsorbed a correlation cannot be drawn.

Characterization of 2-line Fh: The XRD diffractogram in FIG. 23 identifies the material as two-line Fh. the two broad peaks (or 2 lines) at 35° and 62.5° that define 2-line Fh are in good agreement with Bragg peaks reported in the literature ranging from 34-35° and 61-63° 2θ for Cu-Kα irradiation (Li, et al., Dalt. Trans. 40, 2062-2066 (2011); Smith, et al. Inorg. Chem. 51, 6421-6424 (2012); Jia, Environ. Sci. Technol. 40, 3248-3253 (2006); Villacis-Garcia, et al. Boletin de la Sociedad Geológica *Mexicana* Volumen 67. (2015); Zhu, et al. RSC Adv. 5, 84389-84397 (2015); Das, et al., Environ. Sci. Technol. 45, 268-275 (2011); Zhao, et al., Clays Clay Miner. 42, 737-746 (1994); Jiang, et al. Appl. Surf Sci. 353, 1087-1094 (2015)). The FTIR spectrum in FIG. 24 shows broad bands at 3400 and 3200 cm$^{-1}$ attributable to structural hydroxide and sorbed $H_2O$, respectively. A series of peaks between 1750 and 800 cm$^{-1}$ are associated with the various vibrational modes of bicarbonate and carbonate, which are formed from adsorbed CO2 (Baltrusaitis, et al., J. Phys. Chem. C 111, 14870-14880 (2007); Hausner, et al., J. Colloid Interface Sci. 337, 492-500 (2009); Baltrusaitis, et al., Chem. Eng. J. 170, 471-481 (2011); Hakim, et al. Ind. Eng. Chem. Res. 55, 7888-7897 (2016)). TEM and SEM images in FIG. 25 and FIG. 26, respectively, suggest that the material is composed of particles with diameters less than 10 nm in size aggregated into larger particles on the micrometer scale. Additionally, FIG. 26 also shows smaller particles of varying size and shape embedded into larger particles. BET measurements show that Fh has a high surface area of 192 m$^2$/g, falling within the lower end of values found in the literature and lower than the 250 m$^2$/g reported by Smith et al (*Inorg. Chem.* 51, 6421-6424 (2012)). However, different batches produced using the SDM method yielded surface areas varying from 192 to 329 m$^2$/g (Table 3), and special attention should be paid to reported surface area values (Table 4).

System Performance: FIGS. 27 and 28 show the system's removal of arsenite using 1.22 and 2.61 g/L Fh loadings. The amount of arsenite in the lumen and in the service fluid over time are presented as mass fractions of the total arsenite added to the lumen initially. Total arsenite for the 1.22 g/L and 2.61 g/L loadings was 20.2 mg and 25.1 mg, respectively. During treatment, the amount of arsenite in the service fluid slowly increased and eventually plateaued as arsenite passed through the membrane and was distributed into the service fluid. At the end of three hours, concentration in the lumen had decreased by 95% (at Fh loading of 1.22 g/L) and 98% (at Fh loading of 2.61 g/L), suggesting high arsenite removal for both Fh loadings. However, the 2.61 g/L loading maintained a lower residual mass of arsenite, indicating a greater portion of arsenite was adsorbed. If true removal efficiency is quantified by the mass fraction of adsorbed arsenite, then it can be calculated by a mass balance on arsenite according to equation (1).

$$RE_{sys} = \frac{C_i^{LS} V_i^{LS} - \left(C_f^{LS} V_f^{LS} + V_s \sum_{n=1}^{m-n \geq 1} C_n^{SF} + C_m^{SF} V_f^{SF}\right)}{C_i^{LS} V_i^{LS}} \quad (1)$$

In equation (1), $C_i^{LS} V_i^{LS}$ is the initial mass of arsenite in the lumen (total arsenic); $C_f^{LS} V_f^{LS}$ is the mass of arsenite in the lumen at the end of the experiment;

$$V_s \sum_{n=1}^{m-n \geq 1} C_n^{SF}$$

is the mass of arsenite sampled from the service fluid during the runtime; $C_m^{LS} V_f^{LS}$ is the residual mass of arsenite in the service fluid at the end of the experiment; and m is the total number of samples. Removal efficiencies ($RE_{sys}$) were calculated at 67% and 91% for 1.22 and 2.61 g/L adsorbent loadings, respectively. The 1.22 g/L loading with 20.2 mg of total arsenite had a lower removal efficiency than the 2.61 g/L adsorbent loading with 25.8 mg of total arsenite, suggesting that smaller total arsenic to Fh ratio results in better removal.

Changes in the pH of the system over the course of the treatment process are shown in FIG. 29. The introduction of Fh into the service solution caused a sudden drop in pH for both loadings. Fh has been reported to accumulate protons when exposed to air through a series of reactions as carbon dioxide adsorbs to its bound water layer (Baltrusaitis, et al., J. Phys. Chem. C 111, 14870-14880 (2007); Hausner, et al., J. Colloid Interface Sci. 337, 492-500 (2009); Baltrusaitis, et al., Chem. Eng. J. 170, 471-481 (2011)). This likely occurred during the final drying stage of the synthetic process and is indicated by the FTIR spectrum in FIG. 24. The increased surface acidity transferred into the service fluid during addition of the Fh likely caused a pH drop proportional to the loading. As treatment progressed, adsorption of arsenite onto Fh caused the rise in the pH for both loadings. It has been reported that arsenite adsorbs to ferrihydrite through several possible adsorption reactions resulting in either the net release of $H^+$ or $OH^-$ depending on the operating pH (Jain, et al., Environ. Sci. Technol. 33, 1179-1184 (1999)). The 2.61 g/L loading had a smaller pH recovery than the 1.22 g/L loading because of the higher initial acidity produced by excess Fh.

FIG. 30 shows that the variance in Eh measurements of the system for both loadings. Redox potential is influenced by changes in pH according to the Nernst equation, and the two parameters have an inverse relationship. The steep drop in pH followed by introduction of Fh was mirrored by a corresponding spike in Eh, and the subsequent pH recovery throughout the remaining run-time was mirrored by a subsequent decrease in Eh. For each loading, the extent of change in the Eh was also proportional to the change in pH, with the 2.61 g/L loading having a larger drop in pH and a larger spike in Eh in comparison to the 1.21 g/L loading.

Batch Adsorption: FIG. 31 and FIG. 32 show the removal of arsenite with 1.25 and 2.68 g/L loadings. The amount of arsenite remaining in the solution at each point in time is presented as a mass fraction of the total arsenite introduced initially. The amount of arsenite adsorbed to Fh is calculated by the mass balance on arsenite according to equation (2). In equation (2), $C_i V_i$ is the initial mass of arsenite in solution;

$$V_s \sum_{n=1}^{m-n \geq 1} C_n$$

is the accumulated mass removed from sampling; $C_m V_f$ is the final mass remaining in solution; and m is the total number of samples.

$$RE_{batch} = \frac{C_i V_i - \left(V_s \sum_{n=1}^{m-n \geq 1} C_n + C_m V_f\right)}{C_i V_i} \quad (2)$$

In the experimental replicates, most of the arsenite was removed within 30 minutes. Additional reaction time minimally increased overall removal. For the 1.25 g/L loading, Table 5 shows that on average 73% of the total arsenite in solution was removed within 30 minutes and 82% within 3 hours. Thus, 89% of the arsenite to be removed was removed within that 30-minute mark, leaving 11% to be adsorbed in 2.5 hours. For the 2.68 g/L loading, Table 6 shows that on average 94% of the total arsenite and all arsenite that would be removed within 30 minutes. Raven et al. (Environ. Sci. Technol. 32, 344-349 (1998)) also showed similar adsorption behavior, having high initial removal in less than 30 minutes in 2 g/L Fh suspensions containing 40.01 mg/L and 2000.4 mg/L arsenite at pH 9.2. Li et al (Dalt. Trans. 40, 2062-2066 (2011)) also reported 90% adsorption within 1 hour using a 0.25 g/L Fh loading in a 5 mg/L arsenite solution at pH 7. Zhu (J. Hazard. Mater. 189, 564-571 (2011)) attributed this behavior to a biphasic sorption process. Working with a 5 g/L Fh loading in a 525 mg/L arsenite solution at pH 6, it was noted that a fast, initial sorption process occurred within 0.167 hours (10 minutes) that was followed by a slower secondary sorption process. Overall, these prior reports indicate that the adsorption process of arsenite to Fh is a viable process (Table 7). Rapid adsorption can have a profound effect on treatment processes, minimizing both required contact time (hydraulic retention time) and the size of treatment systems (footprint).

TABLE 5

Accumulated removal of As over time for 1.25 g/L Fh loading.

| | Fraction As Removed | | | | Statistics | |
|---|---|---|---|---|---|---|
| Δt (min) | C | E1 | E2 | E3 | E Avg | E SD |
| 30 | −0.061 | 0.727 | 0.756 | 0.699 | 0.727 | 0.029 |
| 90 | −0.101 | 0.784 | 0.816 | 0.814 | 0.804 | 0.018 |
| 180 | −0.050 | 0.804 | 0.814 | 0.841 | 0.820 | 0.019 |

TABLE 6

Accumulated removal of As over time for 2.68 g/L Fh loading.

| | Fraction As Removed | | | | Statistics | |
|---|---|---|---|---|---|---|
| Δt (min) | C | E1 | E2 | E3 | E Avg | E SD |
| 30 | −0.013 | 0.938 | 0.943 | 0.936 | 0.939 | 0.004 |
| 90 | 0.036 | 0.923 | 0.925 | 0.918 | 0.922 | 0.004 |
| 180 | −0.068 | 0.941 | 0.939 | 0.934 | 0.938 | 0.004 |

TABLE 7

| SA m^2/g | Fh Loading g/L | [AsIII] mg/L | Cap pH 6-8 mg/g Fh | Excess AsIII, mg/L | [AsIII]/Fh Load mg/g | Cap pH 6-8 w/w % | Removal Efficiency | Reference |
|---|---|---|---|---|---|---|---|---|
| 180 | 5.1 | 749.22 | 97.4 | 252.48 | 146.9 | 10% | 66% | Zhu et al 2011 |
| 202 | 2 | 40.01 | 19.99 | 0.03 | 20.0 | 2% | 100% | Raven et al 1998 |
| 202 | 2 | 119.87 | 59.94 | −0.01 | 59.9 | 6% | 100% | Raven et al 1998 |
| 202 | 2 | 2000.4 | 427.05 | 1146.3 | 1000.2 | 43% | 43% | Raven et al 1998 |
| 133 | 0.25 | 5 | 20 | 0 | 20 | 2% | 100% | Li et al 2011 |
| 247 | 25 | 1000 | 40 | 0 | 40 | 4% | 100% | Kim et al 2014 |
| 247 | 25 | 3000 | 108 | 300 | 120 | 11% | 90% | Kim et al 2014 |
| 247 | 25 | 5000 | 154 | 1150 | 200 | 15% | 77% | Kim et al 2014 |
| 247 | 25 | 10000 | 144 | 6400 | 400 | 14% | 36% | Kim et al 2014 |
| 247 | 25 | 20000 | 152 | 16200 | 800 | 15% | 19% | Kim et al 2014 |
| 247 | 25 | 30000 | 168 | 25800 | 1200 | 17% | 14% | Kim et al 2014 |
| 247 | 25 | 40000 | 192 | 35200 | 1600 | 19% | 12% | Kim et al 2014 |
| 247 | 25 | 50000 | 200 | 45000 | 2000 | 20% | 10% | Kim et al 2014 |
| 192 | 1.25 | 99.2 | 65.08 | 17.85 | 79.4 | 6.5% | 82% | This work |
| 192 | 2.68 | 92 | 32.2 | 5.704 | 34.3 | 3.2% | 94% | This work |

Variation of pH and Eh over time for the two Fh loadings is shown in FIGS. 33 and 34. As observed in the system, there is large drop in pH and a large increase in Eh. The changes in pH and Eh were inversely related and in proportion to the loading of Fh. Unlike the system, the overall change for both parameters were smoother and occurred over a longer period without a recovery. This is likely a combined effect from the introduction of Fh protons into water and from arsenite adsorption onto Fh. This contention is further supported by other experiments (FIG. 22) where 1.25 g/L of Fh was added to a solution imitating the ionic strength and pH of the batch reactions without arsenite. In this circumstance, the pH dropped sharply and plateaued within 5 minutes.

Comparison of arsenite removal by dialysis to batch adsorption: Performance of the dialysis-based system in comparison to batch adsorption was dependent on the Fh loading and the behavior of the material over the treatment process. In both the dialysis system and batch adsorption, higher Fh loadings resulted in greater removal efficiencies, but batch adsorption was overall more efficient than the system. At the lower 1.22 g/L adsorbent loading, the dialysis system had less total arsenite adsorption in contrast to its batch counterpart, yet it removed only 67% of the total arsenite in comparison to the 82% average removed by batch adsorption. At the higher 2.61 g/L adsorbent loading, where the total arsenite was similar in the dialytic system and in the batch replicates, the system removed 91% of the total arsenite in comparison to the average 94% removed by batch adsorption. Most of the arsenite passed from the membrane lumen into the service fluid, within the treatment period according to FIGS. 27 and 28, and given that batch experiments showed adsorption to be fast, differences in performance cannot be attributed to the unavailability of arsenite for adsorption or an insufficient treatment time. Differences are attributed to changes in the dispersion of Fh over time within the treatment mixtures. FIG. 35 shows that Fh in both batch and dialysis system processes is introduced as a distribution of particles generally well below 100 m in cross section. These particles disperse in solution into a fine colloidal suspension that should facilitate the fast adsorption of arsenite. However, the adsorbent in the dialytic system undergoes noticeable physical changes over the course of the treatment process. As seen in FIG. 36, particles aggregate to a large size and can lodge in rough surfaces within the body of the system. Dispersion of the adsorbent is reduced and is easily noticed by an increase in the translucency of the service fluid. This phenomenon likely adversely affected the removal efficiency of the 1.22 g/L system loading. The 2.61 g/L system loading was able to maintain a high removal because of the excess of Fh present that can counteract the effect of particle aggregation. Addition of excess adsorbent, though, underutilizes the material's adsorption capacity. The adsorption capacity of Fh can be calculated as a weight percent by taking the ratio between the concentration of arsenic adsorbed over the adsorbent loading. For the 1.22 and 2.61 g/L system loadings, adsorption capacity is 3.9% and 3.0% w/w, respectively, in comparison to 6.5% and 3.2% w/w for batch adsorption. Adsorption capacity for Fh in the literature has been reported between 2-20% (adapted as w/w) and is heavily dependent on experimental conditions (Table 7).

The disclosure provided herein demonstrates the application of a fluid purification design concept using nanoadsorbents using two-line Fh for the removal of arsenite. These experiments have served as a proof-of-concept for a new approach for applying nanomaterials in fluidic purification. Traditional batch experiments were also conducted to assess the removal efficiency, measure changes in Eh and pH, and compare the results to those obtained from the proposed system. Final Eh and pH values, at equilibrium, are approximately close for both batch experiments, however, initial Eh and pH changes are dissimilar. This is an important observation that should be considered in designing an industrial-scale purification system with short hydraulic retention time. A comparison of the two methods showed that for similar adsorbent loadings over the same runtime, the system removed 67% and 91% of arsenite while the batch method adsorbed 82% and 94%.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

I claim:
1. A filter, comprising:
a tubular housing having a proximal end, a distal end and a housing lumen therethrough;
a tubular membrane having a proximal end, a distal end and a membrane lumen therethrough, wherein the tubular membrane is positioned within the housing lumen and is permeable to at least one contaminant within a contaminated fluid sample, and non-permeable to at least one purification nanomaterial having at least one dimension less than 10 nm;
a contaminated fluid sample inlet fluidly connected to the proximal end of the membrane, and a contaminated fluid sample outlet fluidly connected to the distal end of the membrane, thereby creating a sample flow-path from the sample inlet through the membrane lumen to the sample outlet; and
a purification nanomaterial inlet fluidly connected to a distal region of the housing lumen, and a purification nanomaterial outlet fluidly connected to a proximal region of the housing lumen, thereby creating a purification nanomaterial flow-path from the purification nanomaterial inlet through the housing lumen to the purification nanomaterial outlet;
wherein the direction of the sample flow-path is in the opposite direction of the purification nanomaterial flow-path.

2. The filter of claim 1, wherein the tubular membrane is non-permeable to a material with a molecular weight of at least 50 kDa.

3. The filter of claim 1, wherein the tubular membrane comprises a membrane selected from the group consisting of cation exchange membrane (CEM), anion exchange membrane (AEM), alkali anion exchange membrane (AAEM), proton exchange membrane (PEM), charge mosaic membrane (CMM), and bipolar membrane (BPM).

4. The filter of claim 1, wherein the tubular membrane comprises a material selected from the group consisting of an organic polymer, an inorganic polymer, and any combination thereof.

5. The filter of claim 1, wherein the tubular membrane comprises a material selected from the group consisting of a nylon, cellulose, cellulose ester, fluorinated polymer, and any combination thereof.

6. The filter of claim 1, wherein the tubular housing is non-permeable to at least one fluid, at least one contaminant, and at least one purification nanomaterial.

7. The filter of claim 1, wherein the tubular housing comprises a material selected from the group consisting of a glass, quartz, ceramic, silica, alloy, metal alloy, stainless steel, stainless steel alloy, aluminum, aluminum alloy, aluminum oxide, copper, copper alloy, titanium, titanium alloy, brass, plastic, and any combination thereof.

8. The filter of claim 1, wherein the filter further comprises a regeneration unit fluidly connected to the purification nanomaterial inlet and the purification nanomaterial outlet,
wherein the regeneration unit regenerates the purification nanomaterial.

9. A fluid purification system comprising the filter of claim 1.

10. The filter of claim 1, wherein the purification nanomaterial has at least one dimension less than 5 nm.

11. The filter of claim 1, wherein the purification nanomaterial has at least one dimension less than 1 nm.

12. The filter of claim 1, wherein the purification nanomaterial is a 2D nanomaterial.

13. A filter, comprising:
a tubular housing having a proximal end, a distal end and a housing lumen therethrough;
a tubular membrane having a proximal end, a distal end and a membrane lumen therethrough, wherein the tubular membrane is positioned within the housing lumen and is permeable to at least one contaminant within a contaminated fluid sample, and non-permeable to at least one purification material comprising a microorganism;
a contaminated fluid sample inlet fluidly connected to the proximal end of the membrane, and a contaminated fluid sample outlet fluidly connected to the distal end of the membrane, thereby creating a sample flow-path from the sample inlet through the membrane lumen to the sample outlet; and
a purification nanomaterial inlet fluidly connected to a distal region of the housing lumen, and a purification nanomaterial outlet fluidly connected to a proximal region of the housing lumen, thereby creating a purification nanomaterial flow-path from the purification material inlet through the housing lumen to the purification material outlet;
wherein the direction of the sample flow-path is in the opposite direction of the purification material flow-path.

* * * * *